US008211919B2

(12) United States Patent
Sawada et al.

(10) Patent No.: US 8,211,919 B2
(45) Date of Patent: Jul. 3, 2012

(54) AMIDE DERIVATIVES AS ROCK INHIBITORS

(75) Inventors: Kouzo Sawada, Tokyo (JP); Tatsuya Zenkoh, Tokyo (JP); Takeshi Terasawa, Tokyo (JP); Yoshimasa Imamura, Tokyo (JP); Hiroki Fukudome, Tokyo (JP); Satoru Kuroda, Hyogo (JP); Jun Maeda, Tokyo (JP); Junko Watanabe, Tokyo (JP); Hiroshi Inami, Tokyo (JP); Nobuaki Takeshita, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 1103 days.

(21) Appl. No.: 12/065,043

(22) PCT Filed: Aug. 29, 2006

(86) PCT No.: PCT/JP2006/317412

§ 371 (c)(1),
(2), (4) Date: Feb. 27, 2008

(87) PCT Pub. No.: WO2007/026920

PCT Pub. Date: Mar. 8, 2007

(65) Prior Publication Data

US 2009/0105231 A1 Apr. 23, 2009

Related U.S. Application Data

(60) Provisional application No. 60/713,391, filed on Sep. 2, 2005.

(51) Int. Cl.

| | |
|---|---|
| ***A61K 31/44*** | (2006.01) |
| ***A61K 31/47*** | (2006.01) |
| ***A61K 31/505*** | (2006.01) |
| ***A61K 31/54*** | (2006.01) |
| ***C07D 239/02*** | (2006.01) |
| ***C07D 413/00*** | (2006.01) |
| ***C07D 499/48*** | (2006.01) |

(52) U.S. Cl. ..................... 514/346; 514/227.8; 514/307; 514/357; 514/275; 546/146; 546/300; 546/332; 544/58.2; 544/331

(58) Field of Classification Search .................. 546/300, 546/146, 332; 514/346, 357, 227.8, 275, 514/307; 544/58.2, 331
See application file for complete search history.

(56) References Cited

U.S. PATENT DOCUMENTS

| | | | | |
|---|---|---|---|---|
| 4,317,827 | A | 3/1982 | Lesher et al. | |
| 4,376,775 | A * | 3/1983 | Lesher et al. | 514/346 |
| 2002/0032148 | A1 | 3/2002 | Uehata et al. | |
| 2003/0125351 | A1 | 7/2003 | Azuma et al. | |
| 2005/0020623 | A1 | 1/2005 | Yamada et al. | |
| 2005/0085642 | A1 | 4/2005 | Kuwabara et al. | |
| 2005/0096310 | A1 | 5/2005 | Yamada et al. | |
| 2005/0182040 | A1 | 8/2005 | Imazaki et al. | |
| 2006/0167043 | A1 | 7/2006 | Iwakubo et al. | |
| 2006/0247266 | A1 | 11/2006 | Yamada et al. | |
| 2007/0129404 | A1 | 6/2007 | Hagihara et al. | |

FOREIGN PATENT DOCUMENTS

| | | |
|---|---|---|
| EP | 0956865 | 11/1999 |
| EP | 1 034 793 | 9/2000 |
| EP | 1 256 574 | 11/2002 |
| EP | 1 500 643 | 1/2005 |
| EP | 1 541 559 | 6/2005 |
| EP | 1 550 660 | 7/2005 |
| EP | 1 632 492 | 3/2006 |
| EP | 1 679 308 | 7/2006 |
| EP | 1 829 876 | 9/2007 |
| FR | 2483233 | 4/1981 |
| FR | 2530246 | 1/1984 |
| WO | 98/06433 | 2/1998 |
| WO | 00/09162 | 2/2000 |
| WO | 00/78351 | 12/2000 |
| WO | 01/17562 | 3/2001 |
| WO | 02/076976 | 10/2002 |
| WO | 02/100833 | 12/2002 |
| WO | 03/082808 | 10/2003 |
| WO | 2004/009555 | 1/2004 |
| WO | 2004/024717 | 3/2004 |
| WO | 2004/108724 | 12/2004 |
| WO | 2005/003101 | 1/2005 |
| WO | 2005/035501 | 4/2005 |
| WO | 2005/035503 | 4/2005 |
| WO | 2005/035506 | 4/2005 |
| WO | 2005/058891 | 6/2005 |
| WO | 2005/074642 | 8/2005 |
| WO | 2005/074643 | 8/2005 |
| WO | 2005/080934 | 9/2005 |
| WO | 2005/082367 | 9/2005 |

(Continued)

OTHER PUBLICATIONS

B.F.Cain, et al. "Journal of Medicinal Chemistry", vol. 12, No. 2, Mar. 1969, American Chemical Society, pp. 199-206, XP-001074169.

Database Chemcasts, Chemical Abstracts Service, Columbus, Ohio, US; order Nos. MWP 00950, MWP 00952 & Jan. 18, 2005, Interchim, Montlucon, 03103, France, XP-002417017.

Nagatoshi Nishiwaki, et al, "Novel Synthesis of Bihetaryl Compounds", Synthesis, No. 12, 2004, pp. 1996-2000, compounds 3,3c, XP002415508.

Steven M. Bromidge, et al, "Biarylcarbamoylindolines Are Novel and Selective 5-HT2C Receptor Inverse Agonists: Identification of 5-Methyl-1-[[2-[(2-methyl-3-pyridyl)oxy]-5-pyridyl]carbamoyl]-6-trifluoromethylindoline (SB-243213) as a Potential Antidepressant/Anxiolytic Agent", Journal of Medicinal Chemistry, vol. 43, 2000, pp. 1123-1134.

(Continued)

*Primary Examiner* — James O. Wilson
*Assistant Examiner* — Ebenezer O Sackey
(74) *Attorney, Agent, or Firm* — Oblon, Spivak, McClelland, Maier & Neustadt, L.L.P.

(57) ABSTRACT

This invention relates to novel amide derivatives and salts thereof. More particularly, it relates to novel amide derivatives and salts thereof which act as a ROCK inhibitor, to a pharmaceutical composition comprising the same and to a method of using the same therapeutically in the treatment and/or prevention of ROCK-related disease.

7 Claims, No Drawings

FOREIGN PATENT DOCUMENTS

| | | |
|---|---|---|
| WO | 2005/082890 | 9/2005 |
| WO | 2005/097790 | 10/2005 |
| WO | 2005/100342 | 10/2005 |
| WO | 2005/103050 | 11/2005 |
| WO | 2005/105780 | 11/2005 |
| WO | 2005/108397 | 11/2005 |
| WO | 2006/018662 | 2/2006 |
| WO | 2006/044753 | 4/2006 |
| WO | 2006/051311 | 5/2006 |
| WO | 2006/057270 | 6/2006 |
| WO | 2006/058120 | 6/2006 |
| WO | 2006/072792 | 7/2006 |
| WO | 2006/102645 | 9/2006 |

OTHER PUBLICATIONS

Heilbron I M et al., "Arylpyridines. Part IV. 3- and 4-pyridyldiphenyls" Journal of the Chemical Society, Chemical Society. Letchworth , GB, No. Part II, 1940, pp. 1279-1284, ISSN: 0368-1769, XP001027791.

Marie Lamothe, et al., "Differentiation between Partial Agonists and Neutral 5-HT1B Antagonists by Chemical Modulation of 3-[3-(N,N-Dimethylamino)propyl]-4-hydroxy-N-[4-(pyridin-4-yl)phenyl]benzamide (GR-55562)", Journal of Medical Chemistry 1997, vol. 40, pp. 3542-3550.

B.F. Cain, et al., "Potential Antitumor Agents. IX. Bisquaternary Salts", Journal of Medicinal Chemistry American Chemical Society, Washington, US, 1968, pp. 963-966.

S. Jegham, et al., "Use of Chiral Glycerol 2,3-Carbonate in the Synthesis of 3-Aryl-2-oxazolidinones", Tetrahedrom Letters, vol. 39, 1998, pp. 4453-4454.

Fred S. Tanaka, "A regiospecific Photoreaction for Synthesis of 3-Phenylpyridines"; Synthetic Comm., vol. 13, No. 11, 1983, pp. 951-958, XP009077271.

L. Doub, et al., "Some Phenylthiourea Derivatives and their Antituberculous Activity", Journal of the American Chemical Society, vol. 80, May 5, 1958, pp. 2205-2213.

.G.J. Atwell , et al., "Potential Antitumor Agents. VI. Bisquaternary Salts", Journal of Medicinal Chemistry, American Chemical Society. Washington, US, vol. 11, No. 2, Mar. 1968, pp. 295-300.

Japan J. Pharmacol. 79, Suppl I, 211 (1999).

Koichiro Kuwahara, et al., "The effects of the selective ROCK inhibitor, Y27632, on ET-1-induced hypertrophic response in neonatal rat cardiac myocytes—possible involvement of Rho/ROCK pathway in cardiac muscle cell hypertrophy", Febs Letters 452,(1999), pp. 314-318.

Naoki Sawada et al, "Inhibition of Rho-Associated Kinase Results in Suppression of Neointimal Formation of Balloon-Injured Arteries", Journal of the American Heart Association, Circulation 101, (2000), pp. 2030-2033.

Chu Kataoka, et al., "Important Role of Rho-kinase in the Pathogenesis of Cardiovascular Inflammation and Remodeling Induced by Long-Term Blockade of Nitric Oxide Important Role of Rho-kinase in the Pathogenesis of Cardiovascular Synthesis in Rats", Journal of the American Heart Association, Feb. 2002, 39(2), pp. 245-250.

Fumio Imamura, et al.,"Y-27632, an Inhibitor of Rho-associated Protein Kinase, Suppresses Tumor Cell Invasion via Regulation of Focal Adhesion and Focal Adhesion Kinase", Jpn. J. Cancer Res. 91, Aug. 2000, pp. 811-816.

Kazuyuki Itoh, et al., "An essential part for Rho-associated kinase in the transcellular invasion of tumor cells", Nature Medicine, 1999, vol. 5, No. 2, pp. 221-225.

Masahide Nakajima, et al.,"WF-536, Inhibits Metastatic Invasion by Enhancing the Host Cell Barrier and Inhibiting Tumour Cell Motility", Clinical and Experimental Pharmacology and Physiology (2003), 30, pp. 457-463.

Guoyan Wang et al., "RhoA/Rock signaling suppresses hypertrophic chondrocyte differentiation", The Journal of Biological Chemistry, vol. 279, No. 13, Mar. 26, 2004, pp. 13205-13214.

S. Tatsumi, et al., Involvement of Rho-Kinase in Inflammatory and Neuropathic Pain Through Phosphorylation of Myristoylated Alanine-Rich C-Kinase Substrate (MARCKS), Neuroscience 131, (2005), pp. 491-498.

* cited by examiner

AMIDE DERIVATIVES AS ROCK INHIBITORS

CROSS REFERENCES TO RELATED APPLICATIONS

This application is a 371 of International Application No. PCT/JP2006/317412, filed on Aug. 29, 2006, and claims priority to U.S. Provisional Patent Application No. 60/713,391, filed on Sep. 2, 2005.

TECHNICAL FIELD

This invention relates to novel amide derivatives and salts thereof which are useful as a ROCK inhibitor.

BACKGROUND ART

Rho kinases (ROCK) are serine/threonine kinases that function in downstream of Rho which is a low molecular GTP-binding protein, and two ROCK isoforms, ROCK I and ROCK II, have been identified. The enzymes are involved in a variety of biological events such as cytoskeltal control, cell growth, cell migration, apoptosis, inflammation etc. To date, it has been reported that the enzymes are involved in pathology of circulatory system disease, tumor infiltration, osteogenesis etc (see, e.g., Satoh H. et al, Jpn. J. Pharmacol. 79, Suppl I, 211 (1999), Kuwahara K. et al, FEBS Lett 452, 314-318 (1999), Sawada N. et al, Circulation 101, 2030-2033 (2000), Kataoka C. et al, Hypertension. 2002 February; 39(2): 245-50, Imamura F. et al, Jpn. J. Cancer Res. 200; 91: 811-16, Itoh K. et al, Nat. Med. 1999; 5: 221-5, Nakajima M. et al, Clin. exp. Pharmacol. Physiol. 2003 July; 30(7): 457-63), and recently the involvement of the enzymes in chondrocyte differentiation and neurogenic, pains etc has been investigated (see, e.g., Guoyan W. et al, J. Biol. Chem. 2004; 279(13), 13205-13214, Tatsumi S, Neuroscience. 2005; 131 (2) 491-498). With elucidation of such many functions of ROCK in the body, many compounds which can inhibit the functions of the enzymes (ROCK inhibitors) has been studied extensively (see, e.g., WO98/06433, WO00/09162, WO00/78351, WO01/17562, WO02/076976, EP1256574, WO02/100833, WO03/082808, WO2004/009555, WO2004/024717, WO2004/108724, WO2005/003101, WO2005/035501, WO2005/035503, WO2005/035506, WO2005/058891, WO2005/074642, WO2005/074643, WO2005/080934, WO2005/082367, WO2005/082890, WO2005/097790, WO2005/100342, WO2005/103050, WO2005/105780, WO2005/108397, WO2006/044753, WO2006/051311, WO2006/057270, WO2006/058120, WO2006/072792 etc), and it is commonly thought that these ROCK inhibitors have a therapeutic effect on hypertension, atherosclerosis, stroke, angina, arterial obstruction, peripheral arterial disease, peripheral circulation disorder, erectile dysfunction, acute and chronic pain, dementia, Alzheimer's disease, Parkinson's disease, neuronal degeneration, asthma, amyotrophic lateral sclerosis, spinal cord injury, rheumatoid arthritis, osteoarthritis, osteoporosis, psoriasis, multiple sclerosis, diabetes, urinary organ diseases such as overactive bladder (OAB) and benign prostatic hypertrophy (BPH), metastasis, cancer, glaucoma, ocular hypertension, retinopathy, auto immune disease, virus infection, myocardial protection etc.

SUMMARY OF THE INVENTION

This invention relates to novel amide derivatives and salts thereof.

More particularly, it relates to novel amide derivatives and salts thereof which act as a ROCK inhibitor, to a pharmaceutical composition comprising the same and to a method of using the same therapeutically in the treatment and/or prevention of ROCK-related disease.

One object of this invention is to provide new and useful amide derivatives and salts thereof which act as a ROCK inhibitor.

A further object of this invention is to provide a pharmaceutical composition comprising, as an active ingredient, said amide derivatives and salts thereof.

Still further object of this invention is to provide a therapeutical method for the treatment and/or prevention of ROCK-related diseases in a patient in need of such disease, using said amide derivatives and salts thereof.

The object amide derivatives of this invention are new and can be represented by the following general formula [I]:

[I]

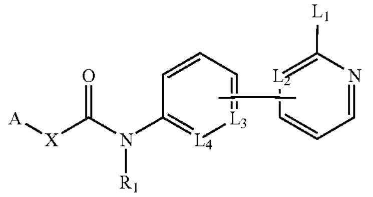

wherein

A is lower alkyl, optionally substituted aryl, optionally substituted cycloalkyl or optionally substituted heterocyclic group;

$L_1$ is —H or —$NH_2$;

$L_2$ is $CR_{14}$ or N;

$L_3$ is CH or N;

$L_4$ is $CR_2$ or N;

$R_1$ is —H and $R_2$ is —H or lower alkyl, or $R_1$ and $R_2$ are taken together to form lower alkylene;

$R_{14}$ is —H or halogen;

X is bond, —$CHR_3$—, —$NR_4$—, —$CHR_5$—$X_1$— or —$X_2$—$CHR_6$—;

$R_3$ is —H, optionally substituted lower alkyl, —OH, —$NH_2$, optionally substituted heterocyclic group;

$R_4$ is —H or optionally substituted lower alkyl;

$X_1$ is —NH—, —$CHR_7$—, —$CHR_{15}$—$X_3$— or —O—;

$R_5$ is —H, optionally substituted lower alkyl, —OH, —$NH_2$, —C(O)$NH_2$, —C(O)$OR_8$, —NHC(O)$OR_9$ or optionally substituted aryl;

$R_7$ is —H, optionally substituted lower alkyl, optionally substituted heterocyclic group, —OH or —$NR_{10}R_{16}$;

$R_8$ and $R_9$ are each independently —H or optionally substituted lower alkyl;

$R_{10}$ and $R_{16}$ are each independently —H or optionally substituted lower alkyl;

$R_{15}$ is —H, optionally substituted lower alkyl or —NHC(O)$OR_{17}$;

$R_{17}$ is —H or optionally substituted lower alkyl;

$X_3$ is —NH— or —$CHR_{18}$;

$R_{18}$ is —H or —$NH_2$;

$X_2$ is —$(CH_2)_n$—$NR_{11}$— or —O—;

$R_6$ is —H or optionally substituted lower alkyl;

n is 0 or 1;

$R_{11}$ is —H, optionally substituted lower alkyl, optionally substituted lower alkanoyl, or —$SO_2R_{12}$;

$R_{12}$ is —H or optionally substituted lower alkyl.

DETAILED DESCRIPTION OF THE PRESENT INVENTION

In the above and subsequent description of the present specification, suitable examples of the various definition to be included within the scope of the invention are explained in detail in the following.

The term "lower" in the specification means as straight or branched carbon chain having 1 to 6 carbon atoms (occasionally abbreviated as $C_1$-$C_6$) unless otherwise indicated.

The "lower alkyl" used in the compound of the present invention may include straight-chain or branched-chain alkyl having 1 to 6 carbon atoms, such as methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and the like. Among them, those having 1 to 4 carbon atoms are preferred, and methyl, ethyl, propyl, isopropyl and tert-butyl are particularly preferred.

The "aryl" used in the compound of the present invention may include mono-, di- or tri-cyclic aromatic hydrocarbon group having 6 to 14 carbon atoms such as phenyl, naphthyl, indenyl and the like, and di- or tri-cyclic aryl which is hydrogenated in one ring such as tetrahydronaphthyl, dihydroindenyl etc. Among them, those having 6 to 10 carbon atoms are preferred, and phenyl, naphthyl and dihydro-indenyl are more preferred.

The "cycloalkyl" used in the compound of the present invention may include 3 to 8-membered saturated hydrocarbon group such as cyclopropyl, cyclobutyl, cyclopentyl, cyclohexyl, cycloheptyl and the like. Among them, cyclohexyl is more preferred.

The "heterocyclic group" used in the compound of the present invention may include 5 to 8-membered monocyclic group containing 1 to 4 hetero atoms selected from the group consisting of oxygen, nitrogen and sulfur atom, and bicyclic heterocyclic group in which 5 to 6-membered monocyclic heterocyclic ring is fused with benzene ring, cycloalkane ring or other monocyclic heterocyclic ring, and example of them includes heteroaryl group such as pyrrolyl, imidazolyl, pyrazolyl, pyridyl, pyrazinyl, pyrimidinyl, pyridazinyl, triazolyl, thienyl, thiopyranyl, furyl, pyranyl, dioxolanyl, thiazolyl, isothiazolyl, thiadiazolyl, thiazinyl, oxazolyl, isoxazolyl, oxadiazolyl, furazanyl, dioxazolyl, oxazinyl, oxadiazinyl, dioxazinyl and the like, saturated heterocyclic group such as pyrrolidinyl, piperidinyl, piperazinyl, morpholinyl, thiomorpholinyl and the like, and fused heterocyclic group such as indolyl, isoindolyl, indazolyl, indolinyl, isoindolinyl, quinolyl, quinazolinyl, quinoxalinyl, isoquinolyl, 3,4-dihydro-isoquinolyl, tetrahydroisoquinolyl, octahydro-isoquinolyl, benzimidazolyl, benzothienyl, benzothiazolyl, benzofuranyl, benzofurazanyl, imidazopyridyl, imidazopyrazinyl, pyridopyridyl, phthalazinyl, naphthyridinyl, indolizinyl, purinyl, quinolizinyl, cinnolinyl, isochromanyl, chromanyl and the like. Preferred one is 5 to 6-membered monocyclic heterocyclic group, or bicyclic heterocyclic group in which 5 to 6-membered monocyclic heterocyclic ring is fused with benzene ring or cyclohexane ring, having 1 or 2 hetero atoms selected from nitrogen atom, oxygen atom and sulfur atom, such as pyrrolyl, pyridyl, furyl, indolyl, indolinyl, thienyl, thiazolyl, benzofuranyl, benzothiazolyl, benzothienyl, quinolyl, 3,4-dihydro-isoquinolyl, tetrahydroisoquinolyl, and octahydro-isoquinolyl.

The term "taken together to form lower alkylene" means that $R_1$ and $R_2$ are taken together to form lower alkylene and form a part of N-containing heterocyclic ring which is fused with neighboring benzene ring. Preferably, $R_1$ and $R_2$ are taken together to form ethylene or propylene, and more preferably $R_1$ and $R_2$ are taken together to form ethylene, and they form a part of pyrroline ring which is fused with neighboring benzene ring to form indoline.

The "lower alkanoyl" used in the compound of the present invention may include formyl, acetyl, propionyl, butyryl, isobutyryl, valeryl, isovaleryl, pivaloyl, hexanoyl, 3,3-dimethylbutyryl, etc.

The "halogen" used in the compound of the present invention may include fluoro, chloro, bromo and iodo, and the like.

The substituent(s) of the "substituted" group used in the compound of the present invention may be any substituent which is generally used in the art as a substituent for the group, and the "substituted" group may have one or more substituents which are same or different each other.

The substituent for "substituted aryl", "substituted cycloalkyl" and "substituted heterocyclic group" may include, but is not limited to, hydroxy, halogen such as fluoro, chloro, bromo and iodo, lower alkyl, halo(lower) alkyl such as chloromethyl, dichloromethyl, trichloromethyl, fluoromethyl, difluoromethyl, trifluoromethyl, bromomethyl, dibromomethyl, tribromomethyl, chloroethyl, dichloroethyl, trichloroethyl, fluoroethyl, difluoroethyl, trifluoroethyl, etc, lower alkoxy such as methoxy, ethoxy, propoxy, isopropoxy, butoxy, isobutoxy, sec-butoxy, tert-butoxy, pentyloxy, tert-pentyloxy, neopentyloxy, hexyloxy, isohexyloxy, etc, carboxy, cyano, amino, nitro, and the like.

The substituent for "substituted lower alkyl" and "substituted lower alkanoyl" may include, but is not limited to, hydroxy, halogen such as fluoro, chloro, bromo and iodo, carboxy, cyano, amino, nitro, and the like.

The preferred embodiment of the present invention is shown as follow.

When X is bond, $-CHR_3-$ or $-NR_4-$ as mentioned above, A is preferably lower alkyl, or mono- or di-cyclic aryl, cycloalkyl, heteroaryl or fused heterocyclic ring, each of which may be optionally substituted, and more preferably, A is phenyl, naphthyl, dihydro-indenyl, cyclohexyl, thienyl, furyl, pyrrolyl, pyridyl, indolyl, indolinyl, benzofuranyl, benzothiazolyl, quinolyl, 3,4-dihydro-isoquinolyl, tetrahydroisoquinolyl and octahydro-isoquinolyl, each of which may be optionally substituted and most preferably unsubstituted. When X is $-CHR_5-X_1-$ or $-X_2-CHR_6-$ as mentioned above, A is preferably aryl, cycloalkyl or monocyclic heterocyclic group each of which may be optionally substituted, and more preferably, A is optionally substituted phenyl, cyclohexyl or thienyl, and most preferably, A is phenyl, cyclohexyl or thienyl. The substituent used in the group A is preferably hydroxy, halogen, lower alkyl, lower alkoxy, carboxy, cyano, amino, or nitro.

$L_1$, $L_2$, $L_3$ and $L_4$ are defined as above, and more preferably, $L_1$ is $-H$ or $NH_2$, $L_2$ is CH or N, $L_3$ is CH, and $L_4$ is $CR_2$.

$R_1$ and $R_2$ are defined as above, and preferably, each independently $-H$ or taken together to form ethylene and consequently form a part of pyrroline ring.

$R_3$ is preferably $-H$, lower alkyl, $-OH$ or $-NH_2$, and more preferably $R_3$ is $-H$.

$R_4$ is preferably $-H$ or lower alkyl, and more preferably, $R_4$ is $-H$.

$X_1$ is defined as above, and more preferably, $X_1$ is $-NH-$ or $-CHR_7-$ wherein $R_7$ is $-H$, or pyrrolidinyl, piperidinyl, piperazinyl, morpholinyl or thiomorpholinyl, each of which may be optionally substituted, or —OH, —$NR_{10}R_{16}$, and most preferably, $R_7$ is —H, morpholinyl, —OH or —$NR_{10}R_{16}$ wherein $R_{10}$ and $R_{16}$ are each independently —H or optionally substituted lower alkyl, and more preferably $R_{10}$ and $R_{16}$ are each independently —H or lower alkyl.

$R_5$ is defined as above, and more preferably, $R_5$ is —H, lower alkyl, lower alkyl substituted with hydroxy or carboxy, —OH, —$NH_2$, —C(O)$NH_2$, —C(O)$OR_8$ or —NHC(O)$OR_9$ wherein $R_8$ and $R_9$ are, each independently, —H or lower alkyl.

$X_2$ is preferably —$(CH_2)_n$—$NR_{11}$— or —O— wherein n is 0 and $R_{11}$, is defined as above, and more preferably, $X_2$ is —$(CH_2)_n$—$NR_{11}$— or —O— wherein n is 0 and $R_{11}$ is —H, lower alkyl, lower alkyl substituted with hydroxy or carboxy, lower alkanoyl, lower alkanoyl substituted with hydroxy or amino, or —$SO_2R_{12}$ wherein $R_{12}$ is —H or lower alkyl.

$R_6$ is defined as above.

Suitable pharmaceutically acceptable salts of the object compound [I] are conventional non-toxic salts and include, for example, a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., trimethylamine salt, triethylamine salt, pyridine salt, picoline salt, ethanolamine salt, triethanolamine salt, dicyclohexylamine salt, N,N'-dibenzylethylenediamine salt, etc.); an inorganic acid addition salt (e.g., hydrochloride, hydrobromide, sulfate, hydrogensulfate, phosphate, etc.); an organic carboxylic or sulfonic acid addition salt (e.g., formate, acetate, trifluoroacetate, maleate, tartrate, citrate, fumarate, methanesulfonate, benzenesulfonate, toluenesulfonate, etc.); and a salt with a basic or acidic amino acid (e.g., arginine, aspartic acid, glutamic acid, etc.).

The compound of the present invention or a salt thereof can be prepared by referring to the present specification and general methods known to the person skilled in the art. Representative reaction processes used for synthesizing the compound of the present invention are shown as follow, but the reaction process used for synthesizing the compound of the present invention is not limited to the following exemplary processes.

Process 1

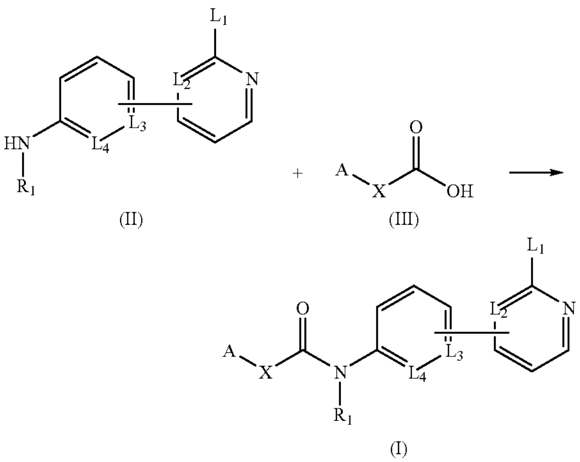

(II) (III) (I)

In the above formula, each of $R_1$, $L_1$, $L_2$, $L_3$, $L_4$, X and A represents the same meaning as defined above. Process 1 is the process for preparing Compound (I), wherein Compound (I) is synthesized by amidation of Compound (II) and (III).

Compound (II) and (III) may be purchased if it is commercial, or synthesized according to general methods obvious to the person skilled in the organic chemistry from commercial compounds.

Process 1 is the process for preparing the Compound (I) from amine Compound (II) and carboxylic acid Compound (III) in solvent.

This process can be carried out by general condensing method, for example, by using condensing agent.

In the case where condensing agent is used, the condensing agent employable in this process is not particularly limited so long as it accelerates, forming amide bond and may include dicyclohexylcarbodiimide (DCC), diisopropyl-carbodiimide (DIPCI), 1-(3-dimethylaminopropyl)-3-ethylcarbodiimide hydrochloride (WSCD), and N-[(dimethylamino) (3H-[1,2,3]triazolo[4,5-b]pyridin-3-yloxy)methylene]-N-methylmethanaminium hexafluorophosphate, (O-(7-azabenzotriazol-1-yl)-1,1,3,3-tetramethyluronium hexafluorophosphate) (HATU), benzotriazole-1-yl-oxy-tris-pyrrolidino-phosphonium hexafluorophosphate (PyBOP), bromo-tris-pyrrolidino-phosphonium hexafluorophosphate (PyBROP).

In the case, base is generally used. The base employable in this process is not particularly limited so long as it accelerates this process and may include organic amines such as triethylamine, tributylamine, diisopropylethylamine (DIEA).

The solvent employable in this process is not particularly limited so long as it is inactive in this reaction and may include amides such as dimethylformamide and dimethylacetamide; halogenated hydrocarbons such as methylene chloride, chloroform.

The temperature at that time varies depending on the starting material, the solvent, or the like, but it is usually ambient temperature.

The reaction time after the adding base varies depending on the starting material, the solvent, or the like, but it is usually from 1 hr to 30 hrs.

After the reaction, the mixture is partitioned between water and organic solvent insoluble with water such as ethyl acetate, chloroform, or the like, and organic layer is separated. The organic layer is washed by water, hydrochloric acid, saturated sodium hydrogencarbonate solution, brine, or the like, dried over anhydrous magnesium sulfate or sodium sulfate, and evaporated in vacuo. The target compound is purified by the conventional method such as silica gel column chromatography, or the like.

Process 2

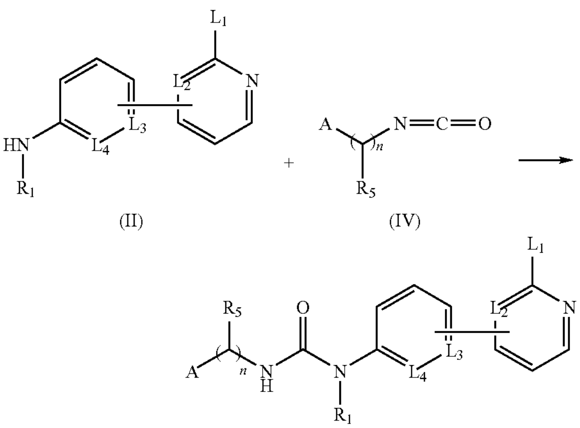

(II) (IV) (Ib)

In the above formula, each of $R_1$, $R_5$, $L_1$, $L_2$, $L_3$, $L_4$ and A represents the same meaning as defined above, and n is 0 or 1.

Process 2 is the process for preparing Compound (Ib), wherein Compound (Ib) is synthesized by reaction of Compound (II) and (IV).

Compound (II) and (IV) may be purchased if it is commercial, or synthesized according to general methods obvious to the person skilled in the organic chemistry from commercial compounds.

Process 2 is the process for preparing the Compound (Ib) from amine Compound (II) and isocyanate Compound (IV) insolvent.

In this process, the Compound (IV) is added to the Compound (II) in the solvent, and after adding, the solution is stirred at, preferably, ambient temperature.

The solvent employable in dissolution of Compound (IV) is not particularly limited so long as it is inactive, and may include dioxane, chloroform, dimethylformamide, dichloromethane etc.

The reaction time varies depending on the starting material, the solvent, or the like, but it is usually from 1 hr to 30 hrs.

After the reaction, the mixture is partitioned between water and organic solvent insoluble with water such as ethyl acetate, chloroform, or the like, and organic layer is separated. The organic layer is washed by water, hydrochloric acid, saturated sodium hydrogencarbonate solution, brine, or the like, dried over anhydrous magnesium sulfate or sodium sulfate, and evaporated in vacuo. The target compound is purified by the conventional method such as silica gel column chromatography, or the like.

Process 3

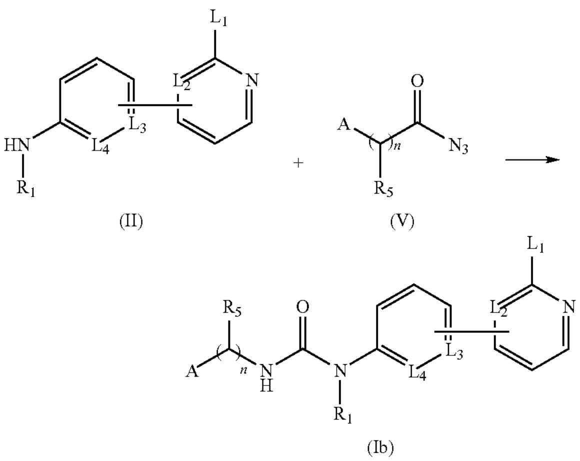

In the above formula, each of $R_1$, $R_5$, $L_1$, $L_2$, $L_3$, $L_4$, A and n represents the same meaning as defined above. Process 3 is the process for preparing Compound (Ib), wherein Compound (Ib) is synthesized by reaction of Compound (II) and (V).

Compound (II) and (V) may be purchased if it is commercial, or synthesized according to general methods obvious to the person skilled in the organic chemistry from commercial compounds.

Process 3 is the process for preparing the Compound (Ib) from amine Compound (II) and azide Compound (V) in solvent.

In this process, first, azide Compound (V) is dissolved in solvent, and stirred under elevated temperature e.g., about 70° C. to 90° C.

The solvent employable in dissolution of Compound (V) is not particularly limited so long as it is inactive, and may include dioxane, chloroform, dimethylformamide, dichloromethane etc.

Then, amine Compound (II) are added to the solution under cooling e.g., about −10° C. to 20° C. to, and after adding, the temperature is preferably raised to ambient temperature to react two compound.

The reaction time varies depending on the starting material, the solvent, or the like, but it is usually from 1 hr to 30 hrs.

After the reaction, the mixture is partitioned between water and organic solvent insoluble with water such as ethyl acetate, chloroform, or the like, and organic layer is separated. The organic layer is washed by water, hydrochloric acid, saturated sodium hydrogencarbonate solution, brine, or the like, dried over anhydrous magnesium sulfate or sodium sulfate, and evaporated in vacuo. The target compound is purified by the conventional method such as silica gel column chromatography, or the like.

Process 4

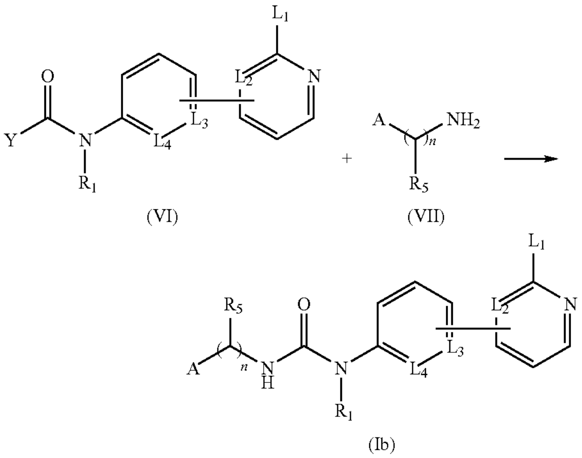

In the above formula, each of $R_1$, $R_5$, $L_1$, $L_2$, $L_3$, $L_4$, A and n represents the same meaning as defined above, and Y is any leaving group. Process 4 is the process for preparing Compound (Ib), wherein Compound (Ib) is synthesized by reaction of Compound (VI) and (VII).

Compound (VI) and (VII) may be purchased if it is commercial, or synthesized according to general methods obvious to the person skilled in the organic chemistry from commercial compounds. Alternatively, Compound (VI) may be synthesized according to other preparation processes described in the present specification.

Process 4 is the process for preparing the Compound (Ib) from carbamate Compound (VI) and amine Compound (VII) in solvent by using general method.

In the case, base is generally used. The base employable in this process is not particularly limited so long as it accelerates this process and may include organic amines such as triethylamine, tributylamine, diisopropylethylamine (DIEA).

The solvent employable in this process is not particularly limited so long as it is inactive in this reaction and may include amides such as dimethylformamide and dimethylacetamide; halogenated hydrocarbons such as dichloromethane, chloroform.

The temperature at that time varies depending on the starting material, the solvent, or the like, but it is usually ambient temperature.

The reaction time after the adding base varies depending on the starting material, the solvent, or the like, but it is usually from 1 hr to 30 hrs.

After the reaction, the mixture is partitioned between water and organic solvent insoluble with water such as ethyl acetate, chloroform, or the like, and organic layer is separated. The organic layer is washed by water, hydrochloric acid, saturated sodium hydrogencarbonate solution, brine, or the like, dried over anhydrous magnesium sulfate or sodium sulfate, and evaporated in vacuo. The target compound is purified by the conventional method such as silica gel column chromatography, or the like.

Process 5

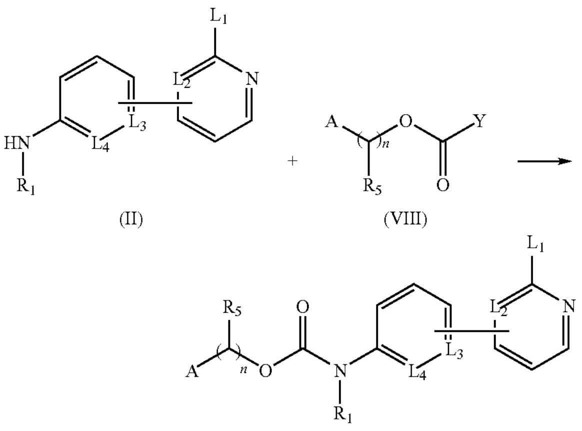

(II) (VIII) (Ic)

In the above formula, each of $R_1$, $R_5$, $L_1$, $L_2$, $L_3$, $L_4$, A, n and Y represents the same meaning as defined above. Process 5 is the process for preparing Compound (Ic), wherein Compound (Ic) is synthesized by carbamation of Compound (II) and (VIII).

Compound (II) and (VIII) may be purchased if it is commercial, or synthesized according to general methods obvious to the person skilled in the organic chemistry from commercial compounds.

Process 5 is the process for preparing the Compound (Ic) from amine Compound (II) and carbonyl Compound (VIII) in solvent. Preferably, Compound (VIII) is added to Compound (II) in solvent dropwise.

In the case, base is generally used. The base employable in this process is not particularly limited so long as it accelerates this process and may include, for example, pyridine.

The solvent employable in this process is not particularly limited so long as it is inactive in this reaction and may include dichloromethane, dimethylformamide, dimethylacetamide, chloroform etc.

The temperature at that time varies depending on the starting material, the solvent, or the like, but it is preferably ambient temperature.

The reaction time after the adding base varies depending on the starting material, the solvent, or the like, but it is usually from 1 hr to 30 hrs.

After the reaction, the mixture is partitioned between water and organic solvent insoluble with water such as ethyl acetate, chloroform, or the like, and organic layer is separated. The organic layer is washed by water, hydrochloric acid, saturated sodium hydrogencarbonate solution, brine, or the like, dried over anhydrous magnesium sulfate or sodium sulfate, and evaporated in vacuo. The target compound is purified by the conventional method such as silica gel column chromatography, or the like.

Process 6

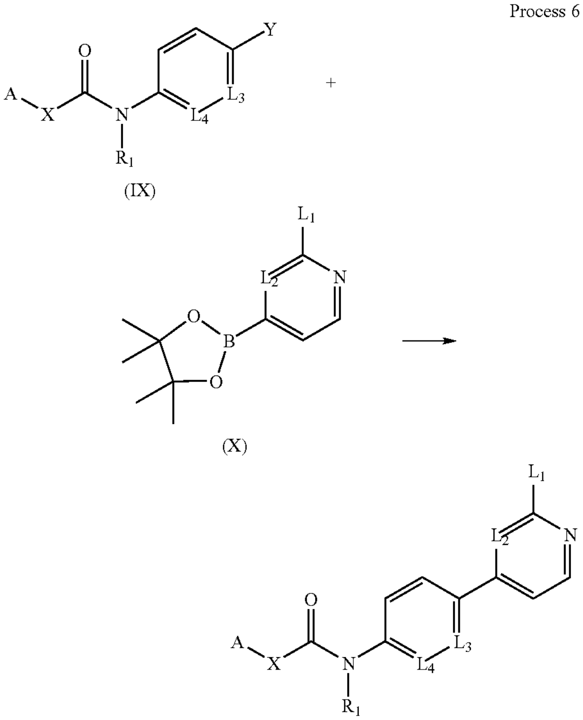

(IX) (X) (Id)

In the above formula, each of $R_1$, $L_1$, $L_2$, $L_3$, $L_4$, X, Y and A represents the same meaning as defined above. Process 6 is the process for preparing Compound (Id), wherein Compound (Id) is synthesized by reaction of Compound (IX) and (X).

Compound (IX) may be purchased if it is commercial, or synthesized according to general methods obvious to the person skilled in the organic chemistry from commercial compounds.

Process 6 is the process for preparing the Compound (Id) from Compound (IX) and boronic ester (X) in solvent.

In this process, first, Compound (IX) and boronic ester (X) are dissolved in solvent.

The solvent employable in dissolution of Compound (IX) is not particularly limited so long as it is inactive, and may include 1,4-dioxane, 1,2-dimethoxyethane etc.

Then, inorganic base and palladium catalyst are added to the solution under nitrogen atmosphere, and after adding, the temperature is preferably raised to 80° C. to 150° C.

In the case where inorganic base is used, the inorganic base employable in this process is not particularly limited so long as it accelerates forming C—C bond formation and may include sodium carbonare, potassium carbonate, cesium carbonate, potassium phosphate, sodium acetate, potassium acetate, sodium hydroxide, potassium hydroxide etc.

In the case where palladium catalyst is used, the palladium catalyst employable in this process is not particularly limited so long as it accelerates forming C—C bond formation and may include [1,1'-bis(diphenylphosphino)ferrocene]dichloropalladium(II), complex with dichloromethane, dichlorobis(tricyclohexyl phosphine)palladium(II), dichlorobis(tri-o-tolylphosphine) palladium(II), dichlorobis (triphenylphosphine) palladium(II), palladium (II) acetate, tetrakis(triphenylphosphine) palladium (0), tris(dibenzylideneacetone)dipalladium(0)-chloroform adduct etc.

The reaction time varies depending on the starting material, the solvent, or the like, but it is usually from 1 hr to 30 hrs.

After the reaction, the mixture is partitioned between water and organic solvent insoluble with water such as ethyl acetate, chloroform, or the like, and organic layer is separated. The organic layer is washed by water, hydrochloric acid, saturated sodium hydrogencarbonate solution, brine, or the like, dried over anhydrous magnesium sulfate or sodium sulfate, and evaporated in vacuo. The target compound is purified by the conventional method such as silica gel column chromatography, or the like.

Process 7

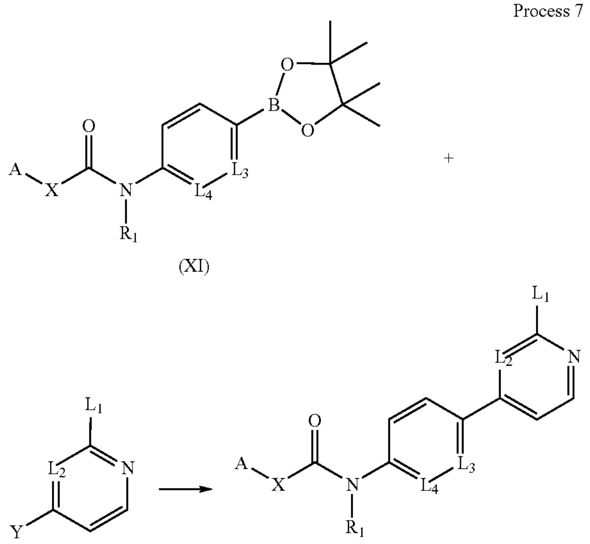

(XI) (XII) (Ie)

In the above formula, each of $R_1$, $L_1$, $L_2$, $L_3$, $L_4$, X, Y and A represents the same meaning as defined above. Process 7 is the process for preparing Compound (Ie), wherein Compound (Ie) is synthesized by reaction of Compound (XI) and (XII).

Compound (XI) may be purchased if it is commercial, or synthesized according to general methods obvious to the person skilled in the organic chemistry from commercial compounds.

Process 7 is the process for preparing the Compound (Ie) from boronic ester Compound (XI) and Compound (XII) in solvent.

In this process, first, boronic ester Compound (XI) and Compound (XII) are dissolved in solvent.

The solvent employable in dissolution of Compound (XI) is not particularly limited so long as it is inactive, and may include 1,4-dioxane, 1,2-dimethoxyethane etc.

Then, inorganic base and palladium catalyst are added to the solution under nitrogen atmosphere, and after adding, the temperature is preferably raised to 80° C. to 150° C.

In the case where inorganic base is used, the inorganic base employable in this process is not particularly limited so long as it accelerates forming C—C bond formation and may include sodium carbonate, potassium carbonate, cesium carbonate, potassium phosphate, sodium acetate, potassium acetate, sodium hydroxide, potassium hydroxide etc.

In the case where palladium catalyst is used, the palladium catalyst employable in this process is not particularly limited so long as it accelerates forming C—C bond formation and may include [1,1'-bis(diphenylphosphino)ferrocene]dichloropalladium(II), complex with dichloromethane, dichlorobis (tricyclohexyl phosphine)palladium(II), dichlorobis(tri-o-tolylphosphine) palladium(II), dichlorobis (triphenylphosphine) palladium(II), palladium (II) acetate, tetrakis(triphenylphosphine) palladium (0), tris(dibenzylideneacetone)dipalladium(0)-chloroform adduct etc.

The reaction time varies depending on the starting material, the solvent, or the like, but it is usually from 1 hr to 30 hrs.

After the reaction, the mixture is partitioned between water and organic solvent insoluble with water such as ethyl acetate, chloroform, or the like, and organic layer is separated. The organic layer is washed by water, hydrochloric acid, saturated sodium hydrogencarbonate solution, brine, or the like, dried over anhydrous magnesium sulfate or sodium sulfate, and evaporated in vacuo. The target compound is purified by the conventional method such as silica gel column chromatography, or the like.

The compounds obtained by the above processes can be isolated and purified by a conventional method such as pulverization, recrystallization, column chromatography, reprecipitation, or the like, and converted to the desired salt in conventional manners, if necessary.

It is to be noted that the compound [I] may include one or more stereoisomers due to asymmetric carbon atoms, and all of such isomers and mixture thereof are included within the scope of this invention.

It is further to be noted that isomerization or rearrangement of the object compound [I] may occur due to the effect of the light acid, base or the like, and the compound obtained as the result of said isomerization or rearrangement is also included within the scope of the present invention.

It is also to be noted that the solvating form of the compound [I] (e.g. hydrate, etc.) and any form of the crystal of the compound [I] are included within the scope of the present invention.

It is also to be noted that pharmaceutical acceptable prodrugs of the compound [I] are included within the scope of the present invention. Pharmaceutical acceptable prodrug means compound having functional groups which can be converted to —COOH, —$NH_2$, —OH etc in physiological condition to form the compound [I] of the present invention.

The compounds of the present invention or a salt thereof can inhibit an activity of any Rho kinase such as ROCK I and ROCK II. Therefore, the compounds of the present invention are useful for the treatment and/or prevention of a variety of ROCK-related diseases. ROCK-related disease which can be treated and/or prevented by using the compound of the present invention includes, but is not limited to, hypertension, atherosclerosis, stroke, angina, arterial obstruction, peripheral arterial disease, peripheral circulation disorder, erectile dysfunction, acute and chronic pain, dementia, Alzheimer's disease, Parkinson's disease, neuronal degeneration, asthma, amyotrophic lateral sclerosis, spinal cord injury, rheumatoid arthritis, osteoarthritis, osteoporosis, psoriasis, multiple sclerosis, diabetes, urinary organ diseases such as overactive bladder (OAB) and benign prostatic hypertrophy (BPH), metastasis, cancer, glaucoma, ocular hypertension, retinopathy, auto immune disease, virus infection, myocardial protection. Because the compounds of the present invention or a salt thereof have pain alleviation and cartilage protection effect, preferably, ROCK-related disease which can be treated and/or prevented by using the compound of the present invention are osteoarthritis, rheumatoid arthritis and osteoporosis, and more preferably, osteoarthritis.

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral, external including topical, internal, intravenous, intramuscular, inhalant, nasal, intraarticular, intraspinal, transtracheal or transocular administration. The pharmaceutical preparations may be solid, semi-solid or solutions such as capsules, tablets, pellets, dragees, powders, granules, suppositories, ointments, creams, lotions, inhalants, injections, cataplasms, gels, tapes, eyedrops, solution, syrups, aerosols, suspension, emulsion, or the like. If desired, there may be included in these preparations, auxiliary substances, stabilizing agents, wetting or emulsifying agents, buffers and other commonly used additives.

While the dosage of the compound [I] will vary depending upon the age and condition of a patient, an average single dose of about 0.1 mg, 1 mg, 10 mg, 50 mg, 100 mg, 250 mg, 500 mg and 1000 mg of the compound [I] may be effective for treating ROCK-related diseases. In general, amounts between 0.1 mg/body and about 1,000 mg/body may be administered per day.

During the preparation of the above-mentioned pharmaceutical administration forms, the compound (I) or a salt thereof can also be combined together with other substances.

The following Preparations and Examples are given for the purpose of illustrating this invention.

Preparation 1

To a suspension of 4-(4-pyridinyl)aniline (4.50 g) in dichloromethane (135 mL) and pyridine (32.1 mL) was added portionwise 4-nitrophenyl chloroformate (6.40 g) at ambient temperature and the mixture was stirred at the same temperature for 4 hours. 4-Nitrophenyl chloroformate (1.60 g) was added to the mixture and the mixture was stirred at ambient temperature for 2 hours. The resulting mixture was concentrated in vacuo and water (80 mL) was added to the residue. The precipitated solid was collected by filtration. The solid was triturated with ethyl acetate (40 mL) to give 4-nitrophenyl[4-(4-pyridinyl)phenyl]carbamate (7.58 g) as a yellow solid.

1H-NMR (DMSO-d6): δ7.59 (2H, d, J=9.3 Hz), 7.71 (2H, d, J=8.6 Hz), 7.91 (2H, d, J=7.5 Hz), 7.93 (2H, d, J=8.6 Hz), 8.33 (2H, d, J=9.3 Hz), 8.70 (2H, d, J=7.5 Hz), 10.70 (1H, s)

MS (ESI, m/z): 336 (M+H)

Preparation 2

The following compound was obtained in a similar manner to that of following Example 4.

tert-butyl(2S)-phenyl[({[4-(4-pyridinyl)phenyl]amino}carbonyl)amino]acetate

1H-NMR ($CDCl_3$): δ1.41 (9H, s), 5.51 (1H, d, J=7.2 Hz), 6.26 (1H, d, J=7.2 Hz), 7.17 (1H, s), 7.29-7.45 (9H, m), 7.50 (2H, d, J=8.5 Hz), 8.59 (2H, d, J=5.7 Hz)

MS (ESI, m/z): 404 (M+H)

Preparation 3

The following compound was obtained in a similar manner to that of following Example 4.

tert-butyl(2R)-phenyl[({[4-(4-pyridinyl)phenyl]amino}carbonyl)amino]acetate

1H-NMR ($CDCl_3$): δ1.41 (9H, s), 5.51 (1H, d, J=7.2 Hz), 6.26 (1H, d, J=7.2 Hz), 7.17 (1H, s), 7.29-7.45 (9H, m), 7.50 (2H, d, J=8.5 Hz), 8.59 (2H, d, J=5.7 Hz)

MS (ESI, m/z): 404 (M+H)

Preparation 4

To a solution of 1H-indole-3-carboxylic acid (500 mg) in tetrahydrofuran (10 mL) were added triethylamine (0.519 mL) and diphenylphosphoryl azide (0.802 mL) at ambient temperature. The mixture was stirred at 60° C. for 2 hours. Ethyl acetate (10 mL) was added to the mixture at room temperature, and then the organic layer was washed with saturated sodium bicarbonate aqueous solution×2, water and brine, dried over magnesium sulfate, and concentrated in vacuo. The residual solid was recrystallized from ethyl acetate (2 mL). The crystals were washed with n-hexane/chloroform (3:1, 1 mL). The crystals were recrystallized from ethyl acetate again to afford 1H-indole-3-carbonyl azide (192 mg) as white crystals.

1H-NMR ($CDCl_3$): δ7.25 (2H, m), 7.52 (1H, m), 8.05 (1H, m), 8.20 (1H, s), 12.2 (1H, s)

Preparation 5

The following compound was obtained in a similar manner to that of Preparation 4.

1-benzofuran-2-carbonyl azide

1H-NMR (DMSO-d6): δ7.41 (1H, t, J=7.9 Hz), 7.58 (1H, t, J=7.9 Hz), 7.77 (1H, d, J=7.9 Hz), 7.86 (1H, d, J=7.9 Hz), 7.91 (1H, s)

Preparation 6

To a solution of anilinoacetic acid (6.0 g) in acetone/$H_2O$ (1:1, 72 mL) were added triethylamine (18.3 mL) and di-tert-butyl dicarbonate (26.0 g) at ambient temperature and the mixture was stirred at ambient temperature overnight. Acetone was evaporated in vacuo and the residual solution was washed with diethyl ether (40 mL). The aqueous solution was acidified to pH=3 with 1N hydrochloric acid and the mixture was extracted with chloroform (70 mL×3). The combined organic layer was washed with brine and dried over magnesium sulfate. The solvent was evaporated in vacuo and the residue was purified by silica gel column chromatography (250 g, 10% methanol in chloroform) to afford [(tert-butoxycarbonyl)(phenyl)amino]acetic acid (8.78 g) as a brown oil.

1H-NMR (DMSO-d6): δ1.38 (9H, s), 4.20 (2H, s), 7.21 (1H, m), 7.26 (2H, m), 7.32 (2H, m)

Preparation 7

[4-(4-Pyridinyl)phenyl]amine (5.35 g) and [(tert-butoxycarbonyl)(phenyl)amino]acetic acid (7.90 g) were dissolved in N,N-dimethylformamide (250 mL), then N,N-diisopropylethylamine (12.0 mL) and N-[(dimethylamino) (3H-[1,2,3]triazolo[4,5-b]pyridin-3-yloxy)methylene]-N-methylmethanaminium hexafluorophosphate (13.1 g) were added to the mixture at ambient temperature. After stirring at ambient temperature overnight, water (250 mL) was added to the resulting mixture and the mixture was extracted with ethyl acetate (500 mL). The organic layer was washed with brine and dried over magnesium sulfate. The solvent was evaporated in vacuo and the residue was purified by silica gel column chromatography (250 g, n-hexane/ethyl acetate (1:1) then 2% methanol in chloroform). The combined fraction was concentrated in vacuo. The residue was crystallized from 5% ethyl acetate in n-hexane (100 mL). The crystals were collected by filtration and washed with 5% ethyl acetate in n-hexane (20 mL) to afford tert-butyl (2-oxo-2-{[4-(4-pyridinyl)phenyl]amino}ethyl)phenylcarbamate.

1H-NMR (DMSO-d6): δ1.37 (9H, s), 4.37 (2H, s), 7.19 (1H, m), 7.35 (4H, d, J=4.4 Hz), 7.70 (2H, dd, J=1.7, 4.6 Hz), 7.76 (2H, d, J=8.8 Hz), 7.82 (2H, d, J=8.8 Hz), 8.60 (2H, dd, J=1.7, 4.6 Hz), 10.30 (1H, s)

MS (ESI, m/z): 404 (M+H)

Preparation 8 tert-Butyl(2-oxo-2-{[4-(4-pyridinyl)phenyl]amino}ethyl) phenylcarbamate (1.30 g) was dissolved in 50% trifluoroacetic acid in dichloromethane (26 mL) and the mixture was stirred at ambient temperature for 2 hours. The solvent was evaporated in vacuo and the residue was crystallized from n-hexane-ethyl acetate (1:1, 15 mL). The crystals were collected by filtration and washed with n-hexane/ethyl acetate (1:1, 5 mL) to afford 2-anilino-N-[4-(4-pyridinyl)phenyl]acetamide bis(trifluoroacetate) (1.46 g) as yellow crystals.

1H-NMR (DMSO-d6): δ3.93 (2H, s), 6.60 (3H, m), 7.11 (2H, m), 7.87 (2H, d, J=8.9 Hz), 8.06 (2H, d, J=8.9 Hz), 8.33 (2H, d, J=6.9 Hz), 8.89 (2H, d, J=6.9 Hz), 10.40 (1H, s)

MS (ESI, m/z): 304 (M+H)

Preparation 9

To a mixture of 2-anilino-N-[4-(4-pyridinyl)phenyl]acetamide bis(trifluoroacetate) (11.0 g) in methanol (160 ml) was added 1N sodium hydroxide aqueous solution (51.7 mL) at ambient temperature. After stirring at ambient temperature for 2 hours, methanol was evaporated in vacuo. Water (20 mL) was added to the resulting mixture and the residual solid was collected by filtration. The crystals were washed with water (30 mL) to afford 2-anilino-N-[4-(4-pyridinyl)phenyl] acetamide (5.16 g) as colorless crystals.

$^1$H NMR (DMSO-d6): δ3.90 (2H, d, J=6.0 Hz), 6.02 (1H, t, J=6.0 Hz), 6.60 (3H, m), 7.10 (2H, t, J=7.4 Hz), 7.68 (2H, dd, J=1.7, 4.6 Hz), 7.79 (4H, m), 8.59 (2H, d, J=6.0 Hz), 10.20 (1H, s)

MS (ESI m/z): 304 (M+H)

Preparation 10

The following compound was obtained in a similar manner to that of following Example 27.

2-oxo-2-[(2-oxo-2-{[4-(4-pyridinyl)phenyl] amino}ethyl) (phenyl)amino]ethyl Acetate 1H-NMR (DMSO-d6): δ2.02 (3H, s), 4.45 (4H, s), 7.53 (5H, m), 7.69 (2H, d, J=6.2 Hz), 7.72 (2H, d, J=8.8 Hz), 7.80 (2H, d, J=8.8 Hz), 8.59 (2H, d, J=6.2 Hz), 10.28 (1H, s)

MS (ESI, m/z): 404 (M+H)

Preparation 11

To a mixture of 2-anilino-N-[4-(4-pyridinyl)phenyl]acetamide (50.0 mg) and [(tert-butoxycarbonyl)amino]acetic acid (86.6 mg) in N,N-dimethylformamide (1.0 mL) were added diisopropylethylamine (0.189 mL) and N-[(dimethylamino)(3H-[1,2,3]triazolo[4,5-b]pyridin-3-yloxy)methylene]-N-methylmethanaminium hexafluorophosphate (207 mg) at ambient temperature and the mixture was stirred at the same temperature for 24 hours. Water (3.0 mL) was added to the mixture and the resulting mixture was extracted with ethyl acetate (6.0 mL). The organic layer was washed with brine, dried over magnesium sulfate and concentrated in vacuo. The residue was purified by preparative thin-layer chromatography (10% methanol in chloroform) to afford tert-butyl{2-oxo-2-[(2-oxo-2-{[4-(4-pyridinyl)phenyl]amino}ethyl) (phenyl)amino]ethyl}carbamate (36.5 mg) as yellow crystals.

1H-NMR (DMSO-d6): δ1.38 (9H, s), 3.50 (2H, m), 4.46 (2H, s), 6.84 (1H, m), 7.41 (1H, m), 7.49 (4H, m), 7.68 (2H, d, J=6.0 Hz), 7.73 (2H, d, J=8.8 Hz), 7.81 (2H, d, J=8.8 Hz), 8.59 (2H, d, J=6.0 Hz), 10.26 (1H, s)

MS (ESI, m/z): 461 (M+H)

Preparation 12

To a solution of ethyl anilinoacetate (700 mg) in N,N-dimethylformamide (7.0 mL) were added benzyl bromoacetate (1.85 mL) and 2-tert-butylimino-2-diethylamino-1,3-dimethyl-perhydro-1,3,2-diazaphosphorine (2.14 g) at ambient temperature and the mixture was stirred at 60° C. for 3 days. Water (10 mL) was added to the mixture at ambient temperature and the resulting mixture was extracted with ethyl acetate (20 mL). The organic layer was washed with brine and dried over magnesium sulfate. The solvent was evaporated in vacuo and the residue was purified by silica gel column chromatography (250 g, 10% ethyl acetate in n-hexane then 20% ethyl acetate in n-hexane) to afford benzylethyl 2,2'-(phenylimino)diacetate (1.51 g) as a brown oil.

1H-NMR ($CDCl_3$): δ1.26 (3H, t, J=7.1 Hz), 4.14 (2H, s), 4.19 (2H, s), 4.20 (2H, q, J=7.1 Hz), 6.61 (2H, d, J=8.3 Hz), 6.79 (1H, t, J=8.3 Hz), 7.21 (2H, t, J=8.3 Hz), 7.34 (5H, m)

Preparation 13

Benzyl ethyl 2,2'-(phenylimino)diacetate (1.0 g) was dissolved in methanol (15 mL) and 10% palladium on carbon (100 mg) was added to the mixture. The mixture was stirred at ambient temperature for 3 hours under hydrogen atmosphere (3 atms) and filtered through bed of celite. The filtrate was concentrated in vacuo to afford [(2-ethoxy-2-oxoethyl)(phenyl)amino]acetic acid (0.698 g) as a brown oil.

1H-NMR (DMSO-d6): δ1.19 (3H, t, J=7.1 Hz), 4.08 (2H, s), 4.11 (2H, q, J=7.1 Hz), 4.17 (2H, s), 6.51 (2H, d, J=8.4 Hz), 6.67 (1H, t, J=8.4 Hz), 7.16 (2H, t, J=8.4 Hz)

Preparation 14

The following compound was obtained in a similar manner to that of Preparation 7.

ethyl[(2-oxo-2-{[4-(4-pyridinyl)phenyl]amino}ethyl) (phenyl)amino]acetate

1H-NMR (DMSO-d6): δ1.26 (3H, t, J=7.1 Hz), 4.21 (2H, s), 4.22 (2H, q, J=7.1 Hz), 4.39 (2H, s), 6.57 (2H, d, J=8.1 Hz), 6.72 (1H, t, J=8.1 Hz), 7.21 (2H, t, J=8.1 Hz), 7.68 (2H, d, J=6.2 Hz), 7.74 (2H, d, J=8.8 Hz), 7.81 (2H, d, J=8.8 Hz), 8.59 (2H, d, J=6.2 Hz), 10.34 (1H, s)

Preparation 15

To a suspension of phenylboronic acid (1.46 g) and 4A molecular sieves (4.5 g) in dichloromethane (40 mL) were added triethylamine (1.66 mL), methyl-(2S)-2-amino-3-tert-butoxypropanoate hydrochloride (1.26 g) and copper (II) acetate (1.19 g), then the mixture was stirred at ambient temperature for 5 days. The reaction was quenched with 7N ammonia in methanol (15 mL) and the mixture was filtered through a bed of celite. The filtrate was concentrated in vacuo and the residue was purified by silica gel column chromatography (eluent; n-hexane/ethyl acetate (2:1)) to afford methyl-(2S)-2-phenylamino-3-tert-butoxypropanoate (500 mg) as a colorless syrup.

1H-NMR ($CDCl_3$): δ1.17 (9H, s), 3.68 (1H, dd, J=4.2, 8.8 Hz), 3.73 (3H, s), 3.78 (1H, dd, J=3.9, 8.8 Hz), 4.19 (1H, dd, J=3.9, 4.2 Hz), 4.43-4.54 (1H, br), 6.63 (2H, d, J=8.0 Hz), 6.74 (1H, t, J=8.0 Hz), 7.17 (2H, t, J=8.0 Hz)

MS (ESI, m/z): 252 (M+H)

Preparation 16

To a solution of methyl (2S)-2-phenylamino-3-tert-butoxypropanoate (230 mg) in methanol (2.30 mL) was added 1N sodium hydroxide aqueous solution (2.75 mL) and the mixture was stirred at ambient temperature for 2 hours. The resulting solution was acidified with 1N HCl (2.7 mL) to pH=4 and diluted with water (2.7 mL). The mixture was stirred at 0° C. for 20 minutes and the precipitate was collected by filtration followed by washing with water (2.7 mL) to give (2S)-2-phenylamino-3-tert-butoxypropanoic acid (100 mg) as an off-white solid.

1H-NMR (DMSO-d6): δ1.13 (9H, s), 3.25-3.42 (2H, br), 3.61 (1H, dd, J=5.1, 8.7 Hz), 3.64 (1H dd, J=4.5, 8.7 Hz), 4.05

(1H, dd, J=4.9, 5.1 Hz), 6.56 (1H, t, J=7.3 Hz), 6.63 (2H, d, J=8.0 Hz), 7.06 (2H, dd, J=7.3, 8.0 Hz)

MS (ESI, m/z): 238 (M+H)

Preparation 17

The following compound was obtained in a similar manner to that of Preparation 7.

(2S)-2-anilino-3-tert-butoxy-N-[4-(4-pyridinyl)phenyl]propanamide

1H-NMR ($CDCl_3$): δ1.24 (9H, s), 3.74 (1H, dd, J=5.0, 9.0 Hz), 3.88 (1H, dd, J=4.9, 9.0 Hz), 3.96 (1H, ddd, J=3.8, 4.9, 5.0 Hz), 4.72 (1H, d, J=3.8 Hz), 6.73 (2H, d, J=7.8 Hz), 6.85 (1H, t, J=7.3 Hz), 7.24 (2H, dd, J=7.3, 7.8 Hz), 7.48 (2H, d, J=6.0 Hz), 7.61 (2H, d, J=9.0 Hz), 7.67 (2H, d, J=9.0 Hz), 8.63 (2H, d, J=6.0 Hz), 8.95 (1H, s)

MS (ESI, m/z): 390 (M+H)

Preparation 18

To a suspension of ethyl (2S)-2-aminopropanoate hydrochloride (1.0 g) and potassium carbonate (1.8 g) in N,N-dimethylformamide (20 ml) was added (bromomethyl)benzene (1.1 g) at ambient temperature. The reaction mixture was stirred at ambient temperature for 7 hours. The resulting mixture was diluted with ethyl acetate and washed successively with water and brine. The organic layer was dried over anhydrous magnesium sulfate, filtered and concentrated in vacuo. The residue was purified by silica gel column chromatography eluting with 20% ethyl acetate/n-hexane to provide a ethyl (2S)-2-(benzylamino) propanoate.

1H-NMR ($CDCl_3$): δ1.33-1.27 (6H, m), 3.37 (1H, q, J=7.0 Hz), 3.67 (1H, d, J=12.5 Hz), 3.80 (1H, d, J=12.5 Hz), 4.19 (2H, q, J=7.0 Hz), 7.33-7.32 (5H, m)

Preparation 19

To a solution of ethyl (2S)-2-(benzylamino)propanoate (200 mg) and triethylamine (107 mg) in N,N-dimethylformamide (4.0 ml) was added di-tert-butyldicarbonate (232 mg) at ambient temperature. The reaction mixture was stirred at ambient temperature for 5 hours. The solution was diluted with ethyl acetate and washed successively with water and brine. The organic layer was dried over anhydrous magnesium sulfate, filtered and concentrated in vacuo to give a ethyl (2S)-2-[benzyl(tert-butoxycarbonyl)amino]propanoate.

1H-NMR ($CDCl_3$): δ1.24 (3H, t, J=7.0 Hz), 1.53-1.34 (12H, m), 3.93-3.91 (1H, m), 4.15-4.09 (2H, m), 4.62-4.49 (2H, m), 7.32-7.29 (5H, m)

Preparation 20

The following compound was obtained in a similar manner to that of Preparation 16.

(2S)-2-[benzyl(tert-butoxycarbonyl)amino]propanoic Acid

1H-NMR (DMSO-d6): δ1.39-1.19 (12H, m), 4.04-4.02 (1H, m), 4.44-4.42 (2H, m), 7.35-7.30 (5H, m)

Preparation 21

The following compound was obtained in a similar manner to that of Preparation 7.

tert-butyl benzyl((1S)-1-methyl-2-oxo-2-{[4-(4-pyridinyl)phenyl]amino}ethyl)carbamate 1H-NMR (DMSO-d6): δ1.33-1.30 (12H, m), 4.60-4.42 (3H, m), 7.31-7.23 (6H, m), 7.82-7.69 (6H, m), 7.60 (2H, d, J=5.0 Hz).

MS (ESI, m/z): 432 (M+H)

Preparation 22

The following compound was obtained in a similar manner to that of Preparation 15.

ethyl-(2S)-2-anilinopropanoate

1H-NMR ($CDCl_3$): δ1.25 (3H, t, J=7.0 Hz), 1.47 (3H, d, J=6.5 Hz), 4.22-4.13 (3H, m), 6.61 (2H, d, J=7.5 Hz), 6.74 (1H, dd, J=7.5, 7.5 Hz), 7.17 (2H, dd, J=7.5, 7.5 Hz)

Preparation 23

The following compound was obtained in a similar manner to that of Preparation 16.

(2S)-2-anilinopropanoic Acid

1H-NMR (DMSO-d6): δ1.36 (3H, d, J=7.0 Hz), 3.92 (1H, q, J=7.0 Hz), 6.57-6.52 (3H, m), 7.06 (2H, dd, J=7.5, 7.5 Hz)

Preparation 24

The following compound was obtained in a similar manner to that of Preparation 15.

methyl-(2R)-2-anilinopropanoate

1H-NMR ($CDCl_3$): δ1.48 (3H, d, J=7.0 Hz), 3.73 (3H, s), 4.19-4.12 (1H, m), 6.61 (2H, d, J=7.5 Hz), 6.74 (1H, dd, J=7.5, 7.5 Hz), 7.18 (2H, dd, J=7.5, 7.5 Hz)

Preparation 25

The following compound was obtained in a similar manner to that of Preparation 16.

(2R)-2-anilinopropanoic Acid

1H-NMR (DMSO-d6): δ1.36 (3H, d, J=7.0 Hz), 3.92 (1H, r, J=7.0 Hz), 6.57-6.52 (3H, m), 7.06 (2H, dd, J=8.0, 8.0 Hz)

Preparation 26

The following compound was obtained in a similar manner to that of Preparation 15.

methyl (2R)-2-anilino-3-tert-butoxypropanoate

1H-NMR ($CDCl_3$): δ1.17 (9H, s), 3.68 (1H, dd, J=4.2, 8.8 Hz), 3.73 (3H, s), 3.78 (1H, dd, J=3.9, 8.8 Hz), 4.19 (1H, ddd, J=3.9, 4.2, 9.0 Hz), 4.48 (1H, d, J=9.0 Hz), 6.63 (2H, d, J=8.0 Hz), 6.74 (1H, t, J=8.0 Hz), 7.17 (2H, t, J=8.0 Hz)

MS (ESI, m/z): 252 (M+H)

Preparation 27

The following compound was obtained in a similar manner to that of Preparation 16.

(2R)-2-anilino-3-tert-butoxypropanoic Acid

1H-NMR (DMSO-d6): δ1.13 (9H, s), 3.25-3.42 (2H, br), 3.61 (1H, dd, J=5.1, 8.7 Hz), 3.64 (1H, dd, J=4.5, 8.7 Hz), 4.05 (1H, dd, J=4.9, 5.1 Hz), 6.56 (1H, t, J=7.3 Hz), 6.63 (2H, d, J=8.0 Hz), 7.06 (2H, dd, J=7.3, 8.0 Hz)

MS (ESI, m/z): 238 (M+H)

Preparation 28

The following compound was obtained in a similar manner to that of Preparation 7.

(2R)-2-anilino-3-tert-butoxy-N-[4-(4-pyridinyl)phenyl]propanamide

1H-NMR ($CDCl_3$): δ1.25 (9H, s), 3.74 (1H, dd, J=5.0, 9.0 Hz), 3.88 (1H, dd, J=4.9, 9.0 Hz), 3.96 (1H, ddd, J=3.8, 4.9, 5.0 Hz), 4.72 (1H, d, J=3.8 Hz), 6.74 (2H, d, J=7.8 Hz), 6.85 (1H, t, J=7.3 Hz), 7.24 (2H, dd, J=7.3, 7.8 Hz), 7.48 (2H, d, J=6.0 Hz), 7.61 (2H, d, J=9.0 Hz), 7.67 (2H, d, J=9.0 Hz), 8.63 (2H, d, J=6.0 Hz), 8.95 (1H, s)

MS (ESI, m/z): 390 (M+H)

Preparation 29

The following compound was obtained in a similar manner to that of Preparation 7.

tert-butyl 2-({[4-(4-pyridinyl)phenyl]amino}carbonyl)-1-indolinecarboxylate

1H-NMR ($CDCl_3$): δ1.59 (9H, s), 3.40-3.66 (2H, br), 5.02-6.00 (1H, m), 7.03 (1H, t, J=7.4 Hz), 7.18-7.27 (2H, m), 7.47 (2H, d, J=5.9 Hz), 7.58-7.68 (5H, m), 8.63 (2H, d, J=5.9 Hz)

MS (ESI, m/z): 416 (M+H)

Preparation 30

To a solution of 5-bromoindoline (13.86 g) and triethylamine (8.50 g) in dichloromethane (100 mL) was added dropwise phenylacetyl chloride (11.9 g) at 5° C. and the mixture was stirred at ambient temperature for 16 hours. The mixture was poured into water and extracted with ethyl acetate. The separated organic layer was washed with brine, dried over magnesium sulfate and evaporated in vacuo. The residue was purified by column chromatography on silica gel eluting with hexane/ethyl acetate (1:1) to give 5-bromo-1-(phenylacetyl)indoline (16.01 g) as a white powder.

1H-NMR (DMSO-d6): δ3.17 (2H, t, J=6.8 Hz), 3.84 (2H, s), 4.18 (2H, t, J=6.8 Hz), 7.2-7.35 (6H, m), 7.42 (1H, s), 7.98 (1H, d, J=6.9 Hz)

ESI-MS (m/z): 340, 338 (M+Na)

Preparation 31

To a solution of 5-bromoindoline (5.0 g), 2-pyridinylacetic acid hydrochloride (4.82 g) and benzotriazol-1-yl-oxytripyrrolidinophosphonium hexafluorophosphate (PyBOP) (15.8 g) in N,N-dimethylformamide (100 mL) was added dropwise diisoprpylethylamine (6.53 g) at ambient temperature and the mixture was stirred at the same temperature for 20 hours. The mixture was poured into a mixture of ethyl acetate and water and the separated organic layer was washed with water and brine, dried over magnesium sulfate, and evaporated in vacuo. The residue was purified by column chromatography on silica gel eluting with ethyl acetate to give 5-bromo-1-(2-pyridinylacetyl)indoline (5.23 g) as a light-brown powder.

1H-NMR (DMSO-d6): δ3.16 (2H, t, J=6.8 Hz), 4.01 (2H, s), 4.22 (2H, t, J=6.8 Hz), 7.25-7.45 (4H, m), 7.7-7.8 (1H, m), 7.98 (1H, d, J=8.7 Hz), 8.45-8.5 (1H, m)

ESI-MS (m/z): 319, 317 (M+Na)

Preparation 32

To a solution of 1-acetyl-5-bromoindoline (12.01 g) and 4-pyridinylboronic acid (9.22 g) in 1,2-dimethoxyethane (500 mL) were added [1,1'-bis-(diphenylphosphino)ferrocene]dichloropalladium(II), complex with dichloromethane (1.23 g) and potassium phosphate (31.9 g) at ambient temperature and the mixture was stirred at 100° C. for 20 hours. The mixture was evaporated in vacuo to remove 1,2-dimethoxyethane and the residue was dissolved in a mixture of ethyl acetate (600 mL) and water (300 mL). The separated organic layer was washed with brine, dried over magnesium sulfate, and evaporated in vacuo. The residue was purified by column chromatography on silica gel eluting with ethyl acetate to give 1-acetyl-5-(4-pyridinyl)indoline (4.42 g) as a white powder.

1H-NMR (DMSO-d6): δ2.19 (3H, s), 3.22 (6.8H, t), 4.16 (6.8H, t), 7.6-7.75 (4H, m), 8.14 (1H, d, J=6.9 Hz), 8.58 (2H, d, J=6.0 Hz)

ESI-MS (m/z): 239 (M+H)

Preparation 33

To a suspension of 1-acetyl-5-(4-pyridinyl)indoline (715 mg) in ethanol (20 mL) was added 1N sodium hydroxide aqueous solution (1.8 mL) and the mixture was refluxed for 16 hours. The mixture was extracted with ethyl acetate and the separated organic layer was washed with brine, dried over magnesium sulfate, and evaporated in vacuo. The residue was purified by column chromatography on silica gel eluting with ethyl acetate to give 5-(4-pyridinyl)indoline (240 mg) as an yellow powder.

1H-NMR (DMSO-d6): δ2.99 (2H, t, J=6.8 Hz), 3.50 (2H, t, J=6.8 Hz), 5.93 (1H, brs), 6.57 (1H, d, J=8.1 Hz), 7.42 (1H, d, J=8.1 Hz), 7.51 (1H, s), 7.55-7.6 (2H, m), 8.45-8.5 (2H, m)

Preparation 34

The following compound was obtained in a similar manner to that of Preparation 1.

4-nitrophenyl 5-(4-pyridinyl)-1-indolinecarboxylate

1H-NMR (DMSO-d6): 3.27-3.37 (2H, m), 4.28-4.40 (2H, m), 7.61 (2H, d, J=8.7 Hz), 7.89 (1H, d, J=8.1 Hz), 7.99 (1H, d, J=8.1 Hz), 8.05 (1H, s), 8.32 (2H, d, J=6.4 Hz), 8.35 (2H, d, J=8.7 Hz), 8.88 (2H, d, J=6.4 Hz)

MS (ESI, m/z): 362 (M+H)

Preparation 35

The following compound was obtained in a similar manner to that of Preparation 7.

tert-butyl{2-oxo-2-[5-(4-pyridinyl)-2,3-dihydro-1H-indol-1-yl]ethyl}phenylcarbamate 1H-NMR ($CDCl_3$): δ1.44 (9H, s), 3.25-3.36 (2H, m), 4.08-4.19 (2H, m), 4.47 (2H, s), 7.21 (1H, dd, J=7.1, 7.1 Hz), 7.30-7.55 (8H, m), 8.35 (1H, d, J=8.3 Hz), 8.61 (2H, d, J=5.4 Hz)

MS (ESI, m/z): 430 (M+H)

Preparation 36

To a solution of 4-bromoaniline (1.1 g), (2S)-2-[(tert-butoxycarbonyl)amino]-3-phenylpropanoic acid (1.87 g) and diisopropylethylamine (1.82 g) in N,N-dimethylformamide (30 mL) was added (O-(7-azabenzotriazol-1-yl)-1,1,3,3-tetramethyluronium hexafluorophosphate) (HATU) (2.68 g) and the mixture was stirred for 24 hours. Water was added and the mixture was extracted with ethyl acetate. The separated organic layer was washed with brine, dried over magnesium sulfate, and evaporated in vacuo. The residue was purified by column chromatography on silica gel to afford tert-butyl {(1S)-1-benzyl-2-[(4-bromophenyl)amino]-2-oxoethyl}carbamate (2.62 g).

MS (ESI, m/z) 420 (M+H)

Preparation 37

To a suspension of tert-butyl {(1S)-1-benzyl-2-[(4-bromophenyl)amino]-2-oxoethyl}carbamate (1.0 g), 4-(4,4,5,5-tetramethyl-1,3,2-dioxaborolan-2-yl)pyridine (587 mg) and potassium phosphate (1.52 g) in dimethoxyethane (30 mL) was added 1,1'-bis(diphenylphosphino)ferrocene palladium (II) chloride (58 mg) and the mixture was stirred at 120° C. for 4 hours. Water was added and the mixture was extracted with chloroform. The separated organic layer was washed with brine, dried over magnesium sulfate, and evaporated in vacuo. The residue was purified by column chromatography on silica gel to afford tert-butyl[(1S)-1-benzyl-2-oxo-2-{[4-(4-pyridinyl)phenyl]amino}ethyl]carbamate (830 mg).

1H-NMR (DMSO-d6) δ 1.33 (9H, s), 2.8-3.1 (2H, m), 4.3-4.45 (1H, m), 7.1-7.3 (5H, m), 7.31 (2H, d, J=8.8 Hz), 7.68 (2H, d, J=8.8 Hz), 7.76 (2H, d, J=6.8 Hz), 8.90 (2H, d, J=6.8 Hz)

MS (ESI, m/z) 418 (M+H)

Preparation 38

The following compound was obtained in a similar manner to that of Preparation 36.

tert-butyl[(1R)-1-benzyl-2-oxo-2-{[4-(4-pyridinyl) phenyl]amino}ethyl]carbamate

1H-NMR (DMSO-d6): δ1.33 (9H, s), 2.74-3.10 (2H, m), 4.16-4.45 (1H, m), 7.11-7.40 (6H, m), 7.64-7.87 (6H, m), 8.56-8.64 (2H, m), 10.04-10.31 (1H, br)

MS (ESI, m/z): 418 (M+H)

Preparation 39

The following compound was obtained in a similar manner to that of Preparation 36.

tert-butyl[(1S)-1-benzyl-2-oxo-2-{[4-(4-pyridinyl) phenyl]amino}ethyl]methylcarbamate 1H-NMR (DMSO-d6): δ1.20-1.36 (9H, m), 2.61-2.87 (5H, m), 4.70-5.18 (1H, m), 7.12-7.40 (5H, m), 7.64-7.89 (6H, m), 8.57-8.64 (2H, m), 9.95-10.31 (1H, br)

MS (ESI, m/z): 432 (M+H)

Preparation 40

To a solution of ethyl (2E)-2-cyano-3-phenylacrylate (1.2 g) in ethanol (30 mL) was added 10% Palladium hydroxide (0.3 g) and the mixture was hydrogenated at 3 atms. for 2 hours. After removing the catalysts by filtration on celite pad, the filtrate was evaporated in vacuo. The residue was dissolved in 1N HCl (2 mL) and washed with chloroform. The separated aqueous layer was adjusted to pH=7 by addition of saturated sodium bicarbonate solution and extracted with ethyl acetate. The separated organic layer was washed with brine, dried over magnesium sulfate, and evaporated in vacuo. The residue was purified by column chromatography on silica gel to afford ethyl 3-amino-2-benzylpropanoate (388 mg).

1H-NMR (DMSO-d6): δ1.06 (3H, t, J=7.2 Hz), 2.56-2.89 (5H, m), 2.95-3.65 (2H, br), 3.98 (2H, q, J=7.2 Hz), 7.07-7.33 (5H, m)

MS (ESI, m/z): 208 (M+H)

Preparation 41

To a solution of ethyl 3-amino-2-benzylpropanoate (380 mg) in tetrahydrofuran (20 mL) were added di-tert-butyl dicarbonate (408 mg) and triethylamine and the mixture was stirred at ambient temperature for 2 hours. Water was added and the mixture was extracted with ethyl acetate. The separated organic layer was washed with brine, dried over magnesium sulfate, and evaporated in vacuo. The residue was purified by column chromatography on silica gel to afford ethyl 2-benzyl-3-[(tert-butoxycarbonyl)amino]propanoate (566 mg) as an oil.

1H-NMR (DMSO-d6): δ1.06 (3H, t, J=7.2 Hz), 1.37 (9H, s), 2.69-2.88 (3H, m), 3.01-3.24 (2H, m), 3.96 (2H, q, J=7.2 Hz), 6.94-7.06 (1H, m), 7.10-7.33 (5H, m)

MS (ESI, m/z): 330 (M+Na)

Preparation 42

To a solution of ethyl 2-benzyl-3-[(tert-butoxycarbonyl) amino]propanoate (310 mg) in tetrahydrofuran (15 mL) were added 1N sodium hydroxide aqueous solution (6.0 mL) and the mixture was stirred at 60° C. for 5 hours. The mixture was cooled and adjusted to pH=2 by addition of 1N HCl. The mixture was extracted with ethyl acetate and the separated organic layer was washed with brine, dried over magnesium sulfate, and evaporated in vacuo. The residue was purified by column chromatography on silica gel to afford 2-benzyl-3-[(tert-butoxycarbonyl)amino]propanoic acid (228 mg) as an crude oil.

Preparation 43

The following compound was obtained in a similar manner to that of Preparation 36.

tert-butyl(2-benzyl-3-oxo-3-{[4-(4-pyridinyl)phenyl] amino}propyl)carbamate

1H-NMR (DMSO-d6): δ1.35 (9H, s), 2.67-3.30 (5H, m), 6.91-7.04 (1H, m), 7.11-7.34 (5H, m), 7.60-7.82 (6H, m), 8.54-8.64 (2H, m), 9.96-10.10 (1H, br)

MS (ESI, m/z): 432 (M+H)

Preparation 44

The following compound was obtained in a similar manner to that of Preparation 36.

tert-butyl[(1S)-1-benzyl-2-(5-bromo-2,3-dihydro-1H-indol-1-yl)-2-oxoethyl]carbamate 1H-NMR (DMSO-d6): δ1.32 (9H, s), 2.74-3.24 (4H, m), 3.80-4.10 (1H, m), 4.13-4.32 (1H, m), 4.35-4.55 (1H, m), 7.12-7.50 (8H, m), 8.01 (1H, d, J, =8.5 Hz)

MS (ESI, m/z): 468 (M+Na)

Preparation 45

The following compound was obtained in a similar manner to that of Preparation 37.

tert-butyl{(1S)-1-benzyl-2-oxo-2-[5-(4-pyridinyl)-2, 3-dihydro-1H-indol-1-yl]ethyl}carbamate 1H-NMR (DMSO-d6): δ1.33 (9H, s), 2.76-3.30 (4H, m), 3.80-4.10 (1H, m), 4.15-4.38 (1H, m), 4.39-4.60 (1H, m), 7.12-7.50 (5H, m), 7.61-7.74 (4H, m), 8.12-8.26 (1H, m), 8.55-8.63 (2H, m)

MS (ESI, m/z): 444 (M+H)

Preparation 46

The following compound was obtained in a similar manner to that of Preparation 36.

tert-butyl{(1S)-3-[(4-bromophenyl)amino]-3-oxo-1-phenylpropyl}carbamate

1H-NMR (DMSO-d6): δ1.33 (9H, s), 2.72 (2H, d, J=7.5 Hz), 4.84-5.12 (1H, m), 7.14-7.37 (5H, m), 7.40-7.59 (4H, m), 9.94-10.05 (1H, br)

MS (ESI, m/z): 442 (M+Na)

Preparation 47

The following compound was obtained in a similar manner to that of Preparation 37.

tert-butyl[(1S)-3-oxo-1-phenyl-3-{[4-(4-pyridinyl) phenyl]amino}propyl]carbamate 1H-NMR (DMSO-d6): δ1.34 (9H, s), 2.76 (2H, d, J=7.5 Hz), 4.86-5.14 (1H, m), 7.16-7.40 (5H, m), 7.48-7.59 (1H, m), 7.63-7.82 (6H, m), 8.55-8.63 (2H, m), 10.03-10.11 (1H, br)

MS (ESI, m/z): 418 (M+H)

Preparation 48

The following compound was obtained in a similar manner to that of Preparation 36.

tert-butyl{(1R)-3-[(4-bromophenyl)amino]-3-oxo-1-phenylpropyl}carbamate

1H-NMR (DMSO-d6): δ1.33 (9H, s), 2.72 (2H, d, J=7.5 Hz), 4.84-5.11 (1H, m), 7.14-7.38 (5H, m), 7.40-7.60 (4H, m), 9.94-10.04 (1H, br)

MS (ESI, m/z): 442 (M+Na)

Preparation 49

The following compound was obtained in a similar manner to that of Preparation 37.

tert-butyl[(1R)-3-oxo-1-phenyl-3-{[4-(4-pyridinyl) phenyl]amino}propyl]carbamate 1H-NMR (DMSO-d6): δ1.34 (9H, s), 2.76 (2H, d, J=7.5 Hz), 4.86-5.14 (1H, m), 7.14-7.40 (5H, m), 7.47-7.60 (1H, m), 7.62-7.82 (6H, m), 8.55-8.63 (2H, m), 10.02-10.12 (1H, br)

MS (ESI, m/z): 418 (M+H)

Preparation 50

The following compound was obtained in a similar manner to that of Preparation 1.

4-nitrophenyl 2,4'-bipyridin-5-ylcarbamate no purification, no data

Preparation 51

The following compound was obtained in a similar manner to that of Preparation 36.

N-alpha-(tert-butoxycarbonyl)-2-fluoro-N-[4-(4-pyridinyl)phenyl]-D-phenylalaninamide 1H-NMR (DMSO-d6): δ1.33 (9H, s), 2.85-2.95 (1H, m), 3.0-3.1 (1H, m), 4.4-4.5 (1H, m), 7.1-7.35 (5H, m), 7.65-7.8 (6H, m), 8.55-8.6 (2H, m), 10.16 (1H, brs)

MS (ESI, m/z): 436 (M+H)

Preparation 52

The following compound was obtained in a similar manner to that of Preparation 36.

N-alpha-(tert-butoxycarbonyl)-3-fluoro-N-[4-(4-pyridinyl)phenyl]-D-phenylalaninamide 1H-NMR (DMSO-d6): δ1.32 (9H, s), 2.85-2.95 (1H, m), 3.0-3.1 (1H, m), 4.3-4.4 (1H, m), 7.0-7.35 (5H, m), 7.65-7.85 (6H, m), 8.55-8.6 (2H, m), 10.25 (1H, brs)

MS (ESI, m/z): 436 (M+H)

Preparation 53

The following compound was obtained in a similar manner to that of Preparation 36.

N-alpha-(tert-butoxycarbonyl)-4-fluoro-N-[4-(4-pyridinyl)phenyl]-D-phenylalaninamide 1H-NMR (DMSO-d6): δ1.32 (9H, s), 2.8-2.9 (1H, m), 2.95-3.05 (1H, m), 4.25-4.35 (1H, m), 7.15-7.45 (3H, m), 7.3-7.4 (2H, m), 7.65-7.85 (6H, m), 8.55-8.6 (2H, m), 10.25 (1H, brs)

MS (ESI, m/z): 436 (M+H)

Preparation 54

The following compound was obtained in a similar manner to that of Preparation 36.

N-alpha-(tert-butoxycarbonyl)-4-fluoro-N-[4-(4-pyridinyl)phenyl]-L-phenylalaninamide 1H-NMR (DMSO-d6): δ1.32 (9H, s), 2.8-2.9 (1H, m), 2.95-3.05 (NH, m), 4.25-4.35 (1H, m), 7.15-7.45 (3H, m), 7.3-7.4 (2H, m), 7.65-7.85 (6H, m), 8.55-8.6 (2H, m), 10.25 (1H, brs)

MS (ESI, m/z): 436 (M+H)

Preparation 55

The following compound was obtained in a similar manner to that of Preparation 36.

N-alpha-(tert-butoxycarbonyl)-2-chloro-N-[4-(4-pyridinyl)phenyl]-D-phenylalaninamide 1H-NMR (DMSO-d6): δ1.33 (9H, s), 2.95-3.05 (1H, m), 3.1-3.2 (1H, m), 4.4-4.5 (1H, m), 7.2-7.45 (5H, m), 7.65-7.8 (6H, m), 8.55-8.65 (2H, m), 10.14 (1H, brs)

MS (ESI, m/z): 462 (M+H)

Preparation 56

The following compound was obtained in a similar manner to that of Preparation 36.

N-alpha-(tert-butoxycarbonyl)-4-chloro-N-[4-(4-pyridinyl)phenyl]-D-phenylalaninamide 1H-NMR (DMSO-d6): δ1.33 (9H, s), 2.8-2.9 (1H, m), 2.95-3.05 (1H, m), 4.3-4.4 (1H, m), 7.15-7.4 (5H, m), 7.74 (2H, d, J=8.7 Hz), 7.81 (2H d, J=8.7 Hz), 7.65-7.7 (2H, m), 8.55-8.65 (2H, m), 10.26 (1H, brs)

MS (ESI, m/z): 462 (M+H)

Preparation 57

The following compound was obtained in a similar manner to that of Preparation 36.

N-alpha-(tert-butoxycarbonyl)-4-trifluoromethyl-N-[4-(4-pyridinyl)phenyl]-D-phenylalaninamide 1H-NMR (DMSO-d6): δ1.30 (9H, s), 2.9-3.0 (1H, m), 3.05-3.15 (1H, m), 4.35-4.45 (1H, m), 7.24 (1H, d, J=8.5 Hz), 7.55-7.7 (6H, m), 7.75 (2H, d, J=8.7 Hz), 7.81 (2H d, J=8.7 Hz), 8.6-8.65 (2H, m), 10.31 (1H, brs)

MS (ESI, m/z): 486 (M+H)

Preparation 58

The following compound was obtained in a similar manner to that of Preparation 36.

N-alpha-(tert-butoxycarbonyl)-4-methoxy-N-[4-(4-pyridinyl)phenyl]-L-phenylalaninamide 1H-NMR (DMSO-d6): δ 1.33 (9H, s), 2.65-2.75 (1H, m), 2.85-2.95 (1H, m), 3.71 (3H, s), 4.35-4.45 (1H, m), 7.0-7.3 (5H, m), 7.65-7.8 (6H, m), 8.6-8.65 (2H, m), 10.22 (1H, brs)

MS (ESI, m/z): 448 (M+H)

Preparation 59

The following compound was obtained in a similar manner to that of Preparation 36.

tert-butyl[(1R)-2-oxo-2-[[4-(4-pyridinyl)phenyl] amino]-1-(2-thienylmethyl)ethyl]carbamate 1H-NMR (DMSO-d6): δ1.37 (9H, s), 2.98-3.06 (1H, m), 3.2-3.27 (1H, m), 4.3-4.4 (1H, m), 6.95 (2H, d, J=4.4 Hz), 7.22 (1H, d, J=8.2 Hz), 7.35 (1H, d, J=4.6 Hz), 7.65-7.7 (2H, m), 7.75 (2H, d, J=8.9 Hz), 7.80 (2H, d, J=8.9 Hz), 8.59-8.62 (2H, m), 10.30 (1H, brs)

MS (ESI, m/z): 424 (M+H)

Preparation 60

The following compound was obtained in a similar manner to that of Preparation 36.

tert-butyl[(1S)-2-oxo-2-[[4-(4-pyridinyl)phenyl] amino]-1-(2-thienylmethyl)ethyl]carbamate 1H-NMR (DMSO-d6): δ1.37 (9H, s), 2.98-3.06 (1H, m), 3.2-3.27 (1H, m), 4.3-4.4 (1H, m), 6.95 (2H, d, J=4.4 Hz), 7.22 (1H, d, J=8.2 Hz), 7.35 (1H, d, J=4.6 Hz), 7.65-7.7 (2H, m), 7.75 (2H, d, J=8.9 Hz), 7.80 (2H, d, J=8.9 Hz), 8.59-8.62 (2H, m), 10.30 (1H, brs)

MS (ESI, m/z): 424 (M+H)

Preparation 61

The following compound was obtained in a similar manner to that of Preparation 36.

tert-butyl[(1S)-2-oxo-2-[[4-(4-pyridinyl)phenyl] amino]-1-(thiazol-4-ylmethyl)ethyl]carbamate 1H-NMR (DMSO-d6): δ1.35 (9H, s), 3.05-3.13 (1H, m), 3.17-3.23 (1H, m), 4.46-4.53 (1H, m), 7.13 (1H, d, J=8.1 Hz), 7.39 (1H, s), 7.67-7.7 (2H, m), 7.75 (2H, d, J=8.8 Hz), 7.79 (2H, d, J=8.8 Hz), 8.59-8.62 (2H, m), 10.26 (1H, brs)

MS (ESI, m/z): 425 (M+H)

Preparation 62

The following compound was obtained in a similar manner to that of Preparation 36.

tert-butyl[(1R)-2-oxo-2-[[4-(4-pyridinyl)phenyl] amino]-1-(thiazol-4-ylmethyl)ethyl]carbamate 1H-NMR (DMSO-d6): δ1.35 (9H, s), 3.05-3.13 (1H, m), 3.17-3.23 (1H, m), 4.46-4.53 (1H, m), 7.13 (1H, d, J=8.1 Hz), 7.39 (1H, s), 7.67-7.7 (2H, m), 7.75 (2H, d, J=8.8 Hz), 7.79 (2H, d, J=8.8 Hz), 8.59-8.62 (2H, m), 10.26 (1H, brs)

MS (ESI, m/z): 425 (M+H)

Preparation 63

The following compound was obtained in a similar manner to that of Preparation 36.

N-alpha-(tert-butoxycarbonyl)-N-alpha-methyl-N-[4-(4-pyridinyl)phenyl]-D-phenylalaninamide 1H-NMR (DMSO-d6): δ1.31 (9H, s), 2.6-2.7 (1H, m), 2.89 (3H, s), 3.2-3.3 (1H, m), 7.2-7.35 (4H, m), 7.65-7.7 (2H, m), 7.75-7.85 (4H, m), 8.55-8.65 (2H, m), 10.22 (1H, brs)

MS (ESI, m/z): 432 (M+H)

Preparation 64

The following compound was obtained in a similar manner to that of Preparation 36.

tert-butyl(3R)-3-[[4-(4-pyridinyl)phenyl]carbamoyl]-3,4-dihydroisoquinoline-2 (1H)-carboxylate 1H-NMR (DMSO-d6): δ 1.31 (9H, s), 3.02 (1H, q, J=7.4 Hz), 3.25 (1H, dd, J=5.8, 15.2 Hz), 4.36-4.90 (3H, m), 7.24 (4H, br), 7.62-7.84 (6H, m), 8.60 (2H, d, J=6.0 Hz), 10.24 (1H, s)

MS (ESI, m/z): 430 (M+H)

Preparation 65

The following compound was obtained in a similar manner to that of Preparation 36.

tert-butyl(3S)-3-[[4-(4-pyridinyl)phenyl]carbamoyl]-3,4-dihydroisoquinoline-2 (1H)-carboxylate 1H-NMR (DMSO-d6): δ 1.31 (9H, s), 3.02 (1H, q, J=7.4 Hz), 3.25 (1H, dd, J=5.8, 15.2 Hz), 4.36-4.90 (3H, m), 7.24 (4H, br), 7.62-7.84 (6H, m), 8.60 (2H, d, J=6.0 Hz), 10.24 (1H, s)

MS (ESI, m/z): 430 (M+H)

Preparation 66

The following compound was obtained in a similar manner to that of Preparation 36.

N-alpha-(tert-butoxycarbonyl)-N-[4-(4-pyridinyl) phenyl]-D-tryptophanamide

1H-NMR (DMSO-d6): δ 1.34 (9H, s), 2.96-3.05 (1H, m), 3.1-3.18 (1H, m), 4.36-4.46 (1H, m), 6.94-7.02 (2H, m), 7.03-7.08 (1H, m), 7.18 (1H, s), 7.32 (1H, d, J=8.0 Hz), 7.64-7.71 (3H, m), 7.76 (2H, d, J=9.0 Hz), 7.95 (2H, d, J=9.0 Hz), 8.59-8.62 (2H, m), 10.24 (1H, s)

MS (ESI, m/z): 457 (M+H)

Preparation 67

The following compound was obtained in a similar manner to that of Preparation 36.

tert-butyl {(1R)-1-(1-benzothien-3-ylmethyl)-2-oxo-2-[[4-(4-pyridinyl)phenyl]amino]ethyl}carbamate 1H-NMR (DMSO-d6): δ 1.33 (9H, s), 3.1-3.2 (1H, m), 3.23-3.3 (1H, m), 4.48-4.58 (1H, m), 7.23 (1H, d, J=8.1 Hz), 7.34-7.45 (2H, m), 7.51 (1H, s), 7.66-7.68 (2H, m), 7.76 (2H, d, J=8.8 Hz), 7.80 (2H, d, J=8.8 Hz), 7.95-8.02 (2H, m), 8.59-8.62 (2H, m), 10.31 (1H, s)

MS (ESI, m/z): 474 (M+H)

Preparation 68

The following compound was obtained in a similar manner to that of Preparation 36.

tert-butyl{(1R)-2-oxo-1-phenyl-2-[[4-(4-pyridinyl) phenyl]amino]ethyl}carbamate

1H-NMR (DMSO-d6): δ 1.40 (9H, s), 5.39 (1H, d, J=8.1 Hz), 7.28-7.34 (1H, m), 7.37 (2H, t, J=7.1 Hz), 7.52 (2H, d, J=7.1 Hz), 7.58 (1H, d, J=8.2 Hz), 7.67 (2H, dd, J=1.6, 4.5 Hz), 7.74 (2H, d, J=8.8 Hz), 7.79 (2H, d, J=8.9 Hz), 8.60 (2H, dd, J=1.6, 4.5 Hz), 10.46 (1H, s)

MS (ESI, m/z): 404 (M+H)

Preparation 69

The following compound was obtained in a similar manner to that of Preparation 36.

tert-butyl{(1S)-2-oxo-1-phenyl-2-[[4-(4-pyridinyl) phenyl]amino]ethyl}carbamate

1H-NMR (DMSO-d6): δ 1.40 (9H, s), 5.39 (1H, d, J=8.1 Hz), 7.28-7.34 (1H, m), 7.37 (2H, t, J=7.1 Hz), 7.52 (2H, d, J=7.1 Hz), 7.58 (1H, d, J=8.2 Hz), 7.67 (2H, dd, J=1.6, 4.5 Hz), 7.74 (2H, d, J=8.8 Hz), 7.79 (2H, d, J=8.9 Hz), 8.60 (2H, dd, J=1.6, 4.5 Hz), 10.46 (1H, s)

MS (ESI, m/z): 404 (M+H)

Preparation 70

The following compound was obtained in a similar manner to that of Preparation 36.

tert-butyl{(1S)-1-(2-chlorophenyl)-2-oxo-2-[[4-(4-pyridinyl)phenyl]amino]ethyl}carbamate 1H-NMR (DMSO-d6): δ 1.41 (9H, s), 5.66 (1H, d, J=8.2 Hz), 7.33-7.38 (2H, m), 7.40-7.45 (1H, m), 7.46-7.52 (1H, m), 7.69 (2H, dd, J=1.6, 4.6 Hz), 7.76-7.83 (5H, m), 8.60 (2H, dd, J=1.6, 4.6 Hz), 10.46 (1H, s)

MS (ESI, m/z): 460 (M+H)

Preparation 71

The following compound was obtained in a similar manner to that of Preparation 36.

tert-butyl{1-(2-fluorophenyl)-2-oxo-2-[[4-(4-pyridinyl)phenyl]amino]ethyl}carbamate 1H-NMR (DMSO-d6): δ 1.40 (9H, s), 5.61 (1H, d, J=8.2 Hz), 7.21 (2H, q, J=7.7 Hz), 7.34-7.42 (1H, m), 7.42-7.50 (1H, m), 7.66-7.73 (3H, m), 7.78 (4H, dd, J=9.0, 16.1 Hz), 8.60 (2H, dd, J=1.7, 4.6 Hz), 10.43 (1H, s)

MS (ESI, m/z): 444 (M+Na)

Preparation 72

The following compound was obtained in a similar manner to that of Preparation 36.

tert-butyl {(1S)-2-oxo-2-[[4-(4-pyridinyl)phenyl]amino]-1-[2-(trifluoromethyl)phenyl]ethyl}carbamate 1H-NMR (DMSO-d6): δ 1.39 (9H, s), 5.69 (1H, d, J=7.7 Hz), 7.51-7.56 (1H, m), 7.66-7.75 (5H, m), 7.76-7.82 (4H, m), 8.08 (1H, d, J=7.8 Hz), 8.60 (2H, dd, J=1.6, 4.5 Hz), 10.44 (1H, s)

MS (ESI, m/z): 472 (M+H)

Preparation 73

The following compound was obtained in a similar manner to that of Preparation 36.

tert-butyl{1-(2-methoxyphenyl)-2-oxo-2-[[4-(4-pyridinyl)phenyl]amino]ethyl}carbamate 1H-NMR (DMSO-d6): δ 1.40 (9H, s), 3.83 (3H, s), 5.61 (1H, d, J=8.4 Hz), 6.94 (1H, td, J=0.9, 7.5 Hz), 7.02 (1H, d, J=8.2 Hz), 7.30 (1H, t, J=7.6 Hz), 7.34 (1H, dd, J=1.6, 7.6 Hz), 7.38 (1H, d, J=8.3 Hz), 7.68 (2H, dd, J=1.5, 4.5 Hz), 7.78 (4H, t, J=9.9 Hz), 8.59 (2H, dd, J=1.6, 4.6 Hz), 10.15 (1H, s)

MS (ESI, m/z): 456 (M+Na)

Preparation 74

The following compound was obtained in a similar manner to that of Preparation 36.

tert-butyl{(1S)-1-(4-fluorophenyl)-2-oxo-2-[[4-(4-pyridinyl)phenyl]amino]ethyl}carbamate 1H-NMR (DMSO-d6): δ 1.40 (9H, s), 5.39 (1H, d, J=8.0 Hz), 7.20 (2H, t, J=8.8 Hz), 7.52-7.58 (3H, m), 7.67 (2H, dd, J=1.6, 4.6 Hz), 7.73 (2H, d, J=8.8 Hz), 7.79 (2H, d, J=8.8 Hz), 8.60 (2H, dd, J=1.6, 4.6 Hz), 10.46 (1H, s)

MS (ESI, m/z): 444 (M+Na)

Preparation 75

The following compound was obtained in a similar manner to that of Preparation 36.

tert-butyl{1-(2-furyl)-2-oxo-2-[[4-(4-pyridinyl)phenyl]amino]ethyl}carbamate

1H-NMR (DMSO-d6): δ 8.60 (2H, dd, J=1.5, 4.5 Hz), 7.81 (2H, d, J=8.9 Hz), 7.75 (2H, d, J=8.9 Hz), 7.69 (2H, dd, J=1.6, 4.5 Hz), 7.65 (1H, m), 6.43 (1H, dd, J=1.9, 3.1 Hz), 6.40 (1H, s), 5.45 (1H, d, J=8.3 Hz), 1.40 (9H, s)

MS (ESI, m/z): 394 (M+H)

Preparation 76

The following compound was obtained in a similar manner to that of Preparation 36.

tert-butyl {(1S)-2-oxo-2-[[4-(4-pyridinyl)phenyl]amino]-1-(2-thienyl)ethyl}carbamate 1H-NMR (DMSO-d6): δ 1.40 (9H, s), 5.60 (1H, d, J=8.0 Hz), 7.00 (1H, dd, J=8.0, 3.6 Hz), 7.12-7.15 (1H, m), 7.48 (1H, d, J=4.2 Hz), 7.61 (1H, d, J=7.5 Hz), 7.67-7.7 (2H, m), 7.74 (1H, d, J=8.7 Hz), 7.81 (2H, d, J=8.7 Hz), 8.32 (1H, s), 8.59-8.62 (2H, m), 10.52 (1H, brs)

MS (ESI, m/z): 410 (M+H)

Preparation 77

The following compound was obtained in a similar manner to that of Preparation 36.

N-(4-bromophenyl)-N-alpha-(tert-butoxycarbonyl)-D-phenylalaninamide

1H-NMR (DMSO-d6): δ 1.32 (9H, s), 2.84 (1H, dd, J=10.1, 13.6 Hz), 2.98 (1H, dd, J=4.6, 13.7 Hz), 4.26-4.36 (1H, m), 7.18 (2H, m), 7.25-7.35 (4H, m), 7.49 (2H, d, J=8.8 Hz), 7.57 (2H, d, J=8.8 Hz), 10.17 (1H, s)

MS (ESI, m/z): 441 (M+Na)

Preparation 78

The following compound was obtained in a similar manner to that of Example 53.

N-(4-bromophenyl)-D-phenylalaninamide

1H-NMR (DMSO-d6): δ 2.74 (1H, dd, J=8.0, 13.4 Hz), 3.02 (1H, dd, J=5.5, 13.4 Hz), 3.58 (1H, dd, J=5.5, 8.0 Hz), 7.16-7.21 (1H, m), 7.23-7.30 (4H, m), 7.48 (2H, d, J=8.9 Hz), 7.61 (2H, d, J=8.9 Hz)

MS (ESI, m/z): 319 (M+H)

Preparation 79

To a solution of N-(4-bromophenyl)-D-phenylalaninamide (500 mg) in N,N-dimethylformamide (5 mL) were added 1,1'-oxybis(2-bromoethane) (545 mg) and diisopropylethylamine (607 mg) and the mixture was stirred at 50° C. for 6 hours. After being cooled to 5° C., the mixture was poured into water and extracted with ethyl acetate. The organic layer was washed with water and brine, dried over magnesium sulfate, and evaporated in vacuo. The residue was purified by column chromatography on silica gel eluting with hexane/ethyl acetate (1:1) to afford (2R)—N-(4-bromophenyl)-2-morpholin-4-yl-3-phenylpropanamide (430 mg) as a powder.

1H-NMR (DMSO-d6): δ 2.56-2.69 (4H, m), 2.88 (1H, dd, J=5.0, 13.2 Hz), 3.07 (1H, dd, J=9.6, 13.2 Hz), 3.45 (1H, dd, J=5.1, 9.6 Hz), 3.52-3.62 (4H, m), 7.13-7.18 (1H, m), 7.20-7.25 (4H, m), 7.45 (2H, d, J=9.0 Hz), 7.51 (2H, d, J=9.0 Hz), 9.93 (1H, s)

MS (ESI, m/z): 391 (M+H)

Preparation 80

The following compound was obtained in a similar manner to that of Example 53.

N-(4-bromophenyl)-L-phenylalaninamide

1H-NMR (DMSO-d6): δ 2.74 (1H, dd, J=8.0, 13.4 Hz), 3.02 (1H, dd, J=5.5, 13.4 Hz), 3.58 (1H, dd, J=5.5, 8.0 Hz), 7.16-7.21 (1H, m), 7.23-7.30 (4H, m), 7.48 (2H, d, J=8.9 Hz), 7.61 (2H, d, J=8.9 Hz)

MS (ESI, m/z): 319 (M+H)

Preparation 81

The following compound was obtained in a similar manner to that of Preparation 79.

(2S)—N-(4-bromophenyl)-2-morpholin-4-yl-3-phenylpropanamide

1H-NMR (DMSO-d6): δ 2.56-2.69 (4H, m), 2.88 (1H, dd, J=5.0, 13.2 Hz), 3.07 (1H, dd, J=9.6, 13. Hz), 3.45 (1H, dd, J=5.1, 9.6 Hz), 3.52-3.62 (4H, m), 7.13-7.18 (1H, m), 7.20-7.25 (4H, m), 7.45 (2H, d, J=9.0 Hz), 7.51 (2H, d, J=9.0 Hz), 9.93 (1H, s)

MS (ESI, m/z): 391 (M+H)

Preparation 82

The following compound was obtained in a similar manner to that of Preparation 36.

N-(4-bromophenyl)-2-hydroxy-3-phenylpropanamide

1H-NMR (DMSO-d6): δ 2.8-2.86 (1H, m), 3.0-3.06 (1H, m), 4.2-4.26 (1H, m), 5.87 (1H, brs), 7.15-7.3 (6H, m), 7.45-7.5 (2H, m), 7.65-7.7 (2H, m), 9.85 (1H, brs)

MS (ESI, m/z): 342 (M+H)

Preparation 83

To a solution of N-(4-bromophenyl)-2-hydroxy-3-phenylpropanamide (1.5 g) in dichloromethane (60 mL) and tetrahydrofuran (30 mL) were added diisopropylethylamine (908 mg) and 4-dimethylaminopyridine (114 mg), followed by dropwise addition of methanesulfonyl chloride (805 mg) at 5° C. and the mixture was stirred at ambient temperature for 20 hours. The mixture was poured into water and concentrated in vacuo. The residue was extracted with ethyl acetate, washed with brine, dried over magnesium sulfate, and evaporated in vacuo to afford crude 1-benzyl-2-[(4-bromophenyl)amino]-2-oxoethyl methanesulfonate. The crude methanesulfonate was dissolved in N,N-dimethylformamide (30 mL) and 4-piperidinol (1.19 g) was added. The mixture was stirred at 80° C. for 5 hours and poured into water. The mixture was extracted with ethyl acetate, washed with water and brine, dried over magnesium sulfate, and evaporated in vacuo. The residue was purified by column chromatography on silica gel eluting with ethyl acetate to afford N-(4-bromophenyl)-2-(4-hydroxypiperidin-1-yl)-3-phenylpropanamide (894 mg) as a powder.

1H-NMR (DMSO-d6): δ1.3-1.4 (2H, m), 1.64-1.74 (2H, m), 2.26-2.4 (2H, m), 2.78-2.92 (2H, m), 3.01-3.1 (1H, m), 3.36-3.46 (2H, m), 4.52 (1H, d, J=3.9 Hz), 7.1-7.26 (5H, m), 7.44 (2H, d, J=8.8 Hz), 7.52 (2H, d, J=8.8 Hz), 9.86 (1H, brs)

MS (ESI, m/z): 403 (M+H)

Preparation 84

To a solution of ethyl bromo(phenyl)acetate (5.0 g) in ethanol (20 mL) was added 4-piperidinol (5.05 g) and the mixture was stirred at 60° C. for 4 hours. The mixture was poured into dilute sodium bicarbonate aqueous solution and extracted with ethyl acetate. The organic layer was washed with water and brine, dried over magnesium sulfate, and evaporated in vacuo. The residue was purified by column chromatography on silica gel eluting with hexane/ethylacetate (3:7) to afford ethyl (4-hydroxypiperidin-1-yl)(phenyl) acetate (5.21 g) as a yellow oil.

1H-NMR ($CDCl_3$): δ 1.21 (3H, t, J=7.1 Hz), 1.4-1.45 (1H, m), 1.56-1.7 (2H, m), 1.82-1.96 (2H, m), 2.66-2.86 (2H, m), 3.65-3.78 (1H, m), 4.0-4.08 (1H, m), 4.1-4.24 (2H, m), 7.3-7.37 (3H, m), 7.41-7.46 (2H, m)

MS (ESI, m/z): 264 (M+H)

Preparation 85

A suspension of ethyl (4-hydroxypiperidin-1-yl)(phenyl) acetate (5.2 g) in 6N hydrochloric acid (80 mL) was refluxed for 14 hours and the mixture was evaporated in vacuo. The residue was triturated with methanol and collected by filtration and dried in vacuo to afford (4-hydroxypiperidin-1-yl) (phenyl)acetic acid hydrochloride (4.65 g) as a powder.

1H-NMR (DMSO-d6): δ 1.6-1.8 (2H, m), 1.85-2.05 (2H, m), 2.7-3.9 (4H, m), 4.8-5.2 (1H, m), 5.27 (1H, brs), 7.45-7.6 (5H, m)

MS (ESI, m/z): 236 (M+H)

Preparation 86

To a mixture of N-(4-bromophenyl)-D-phenylalaninamide (600 mg) and tetrahydro-4H-pyran-4-one (230 mg) in 1,2-dichloroethane (30 mL) were added acetic acid (135 mg) and sodium triacetoxyborohydride (503 mg) and the mixture was stirred at ambient temperature for 5 hours. The mixture was poured into saturated sodium bicarbonate aqueous solution and extracted with ethyl acetate. The organic layer was washed with brine, dried over magnesium sulfate and evaporated in vacuo. The residue was purified by column chromatography on silica gel eluting with chloroform/methanol (100:1) to afford N-(4-bromophenyl)-N-alpha-(tetrahydro-2H-pyran-4-yl)-D-phenylalaninamide (323 mg) as a powder.

1H-NMR (DMSO-d6): δ 1.05-1.31 (2H, m), 1.58-1.74 (2H, m), 2.0-2.07 (1H, m), 2.76-2.84 (2H, m), 3.14-3.25 (1H, m), 3.5-3.59 (1H, m), 3.7-3.77 (1H, m), 7.15-7.22 (1H, m), 7.22-7.28 (4H, m), 7.44-7.48 (2H, m), 7.52-7.55 (2H m), 9.95 (1H, brs)

MS (ESI, m/z): 403 (M+H)

Preparation 87

The following compound was obtained in a similar manner to that of Preparation 36.

tert-butyl[(1S)-1-benzyl-2-(3,4'-bipyridin-6-ylamino)-2-oxoethyl]carbamate

1H-NMR (DMSO-d6): δ 1.32 (9H, s), 2.6-3.2 (2H, m), 4.4-4.6 (1H, m), 7.1-7.4 (7H, m), 7.7-7.8 (2H, m), 8.15-8.3 (1H, m), 7.6-7.7 (2H, m), 8.84 (1H, s), 10.90 (1H, s)

MS (ESI, m/z): no data

Preparation 88

The following compound was obtained in a similar manner to that of Preparation 36.

tert-butyl[(1R)-1-benzyl-2-(3,4'-bipyridin-6-ylamino)-2-oxoethyl]carbamate

1H-NMR (DMSO-d6): δ 1.32 (9H, s), 2.77-2.88 (2H, m), 2.97-3.06 (1H, m), 4.03-4.12 (1H, m), 7.06 (1H, d, J=8.3 Hz), 7.16-7.3 (5H, m), 7.39 (1H, d, J=8.3 Hz), 7.78 (1H, d, J=4.4 Hz), 8.19-8.28 (1H, m), 8.65 (1H, d, J=4.4 Hz), 10.89 (1H, brs)

MS (ESI, m/z): 419 (M+H)

Preparation 89

The following compound was obtained in a similar manner to that of Preparation 36.

tert-butyl[(1S)-1-benzyl-2-(2,4'-bipyridin-5-ylamino)-2-oxoethyl]carbamate

1H-NMR (DMSO-d6): δ 1.33 (9H, s), 2.78-3.13 (2H, m), 4.15-4.47 (1H, m), 7.13-7.41 (6H, m), 8.01 (2H, dd, J=1.5, 4.6 Hz), 8.11 (1H, d, J=8.6 Hz), 8.24 (1H, dd, J=2.5, 8.6 Hz), 8.67 (2H, dd, J=1.5, 4.6 Hz), 8.86 (1H, d, J=2.5 Hz), 10.35-10.55 (1H, m)

MS (ESI, m/z): 419 (M+H)

Preparation 90

The following compound was obtained in a similar manner to that of Preparation 36.

tert-butyl[(1R)-1-benzyl-2-(2,4'-bipyridin-5-ylamino)-2-oxoethyl]carbamate

1H-NMR (DMSO-d6): δ 1.33 (9H, s), 2.82-2.94 (1H, m), 3.0-3.06 (1H, m), 4.34-4.4 (1H, m), 7.18-7.36 (5H, m), 7.95 (1H, s), 8.01 (2H, dd, J=5.0, 1.7 Hz), 8.11 (1H, d, J=8.7 Hz), 8.23 (1H, dd, J=8.7, 2.5 Hz), 8.67 (2H, dd, 5.0, 1.7 Hz), 8.86 (1H, d, J=2.4 Hz), 10.48 (1H, brs)

MS (ESI, m/z): 419 (M+H)

Preparation 91

To a stirred suspension of (4-nitrophenyl)boronic acid (1.6 g), 4-chloro-3fluoropyridine (1.11 g), and tetrakis (triphenylphosphine) palladium (462 mg) in 1,2-dimethoxyethane (25 mL) was added 0.8M potassium carbonate aqueous solution (25 mL) and the mixture was refluxed under nitrogen for 20 hours. After cooling, 1,2-dimethoxyethane was removed in vacuo. To the residue was added ethyl acetate, washed with water, dried over magnesium sulfate, and concentrated to afford 3-fluoro-4-(4-nitrophenyl)pyridine (2.23 g) as a brown solid.

1H-NMR (DMSO-d6): δ7.52-7.64 (2H, m), 7.73 (1H, dd, J=5.0, 2.6 Hz), 7.97 (2H, dd, J=8.8, 1.3 Hz), 8.39 (2H, dd, 8.8, 1.3 Hz), 8.59 (1H, d, J=5.0 Hz), 8.76 (1H, d, J=2.6 Hz)

MS (ESI, m/z): 189 (M+H)

Preparation 92

To a refluxing mixture of 3-fluoro-4-(4-nitrophenyl)pyridine (2.23 g), trichloroiron (130 mg) and activated carbon (1.12 g, 50 wt % of the starting material) in ethanol (74 mL) was added dropwise hydrazine hydrate (1.6 g), and the mixture was stirred for 3 hours. The insoluble materials were removed by filtration in hot and washed with ethanol. Most of ethanol was removed in vacuo, and to the residue was added water. Resulting solid was collected by filtration, and purified by column chromatography on silica gel eluting with hexane/ethyl acetate (1:2) to afford 4-(3-fluoropyridin-4-yl)aniline (1.36 g) a pale orange solid.

1H-NMR (DMSO-d6): δ5.59 (2H, brs), 6.67 (2H, dd, J=8.6, 1.6 Hz), 7.42 (2H, dd, J=8.6, 1.6 Hz), 7.53 (1H, dd, 7.4, 5.1 Hz), 8.36 (1H, dd, J=3.4, 1.1 Hz), 8.51 (1H, d, J=3.4 Hz)

MS (ESI, m/z): 189 (M+H)

Preparation 93

The following compound was obtained in a similar manner to that of Preparation 36.

N-alpha-(tert-butoxycarbonyl)-N-[4-(3-fluoropyridin-4-yl)phenyl]-D-phenylalaninamide 1H-NMR (DMSO-d6): δ 1.33 (9H, s), 2.82-3.04 (2H, m), 4.32-4.4 (1H, m), 7.16-7.38 (6H, m), 7.6-7.66 (1H, m), 7.67 (2H, d, J=8.7 Hz), 7.76 (2H, d, J=8.7 Hz), 8.48 (1H, d, J=5.8 Hz), 8.63 (1H, d, J=2.8 Hz), 10.29 (1H, brs)

MS (ESI, m/z): 458 (M+Na)

Preparation 94

To a solution of 3-methyl-4-nitrophenol (1.5 g) in pyridine (15 mL) was added dropwise trifluoromethanesulfonic anhydride (3.32 g) at ambient temperature and the mixture was stirred for 1 hour. The mixture was poured into water and extracted with ethyl acetate. The organic layer was washed with 1N hydrochloric acid and brine, dried over magnesium sulfate, and evaporated in vacuo. The residue was purified by column chromatography on silica gel eluting with hexane/ethyl acetate (9:1) to afford 3-methyl-4-nitrophenyl trifluoromethanesulfonate (1.91 g) as a yellow oil.

1H-NMR (DMSO-d6): δ2.57 (3H, s), 7.64 (1H, d, J=9.0, 2.7 Hz), 7.78 (1H, d, J=2.7 Hz), 8.18 (1H, d, J=9.0 Hz)

MS (ESI, m/z): no data

Preparation 95

The following compound was obtained in a similar manner to that of Preparation 37.

4-(3-methyl-4-nitrophenyl)pyridine

1H-NMR (DMSO-d6): δ 2.62 (3H, s), 7.81 (2H, dd, J=1.8, 4.5 Hz), 7.89 (1H, dd, J=2.0, 8.4 Hz), 7.98 (1H, d, J=2.0 Hz), 8.12 (1H, d, J=8.4 Hz), 8.71 (2H, dd, J=1.8, 4.5 Hz)

MS (ESI, m/z): 215 (M+H)

Preparation 96

The following compound was obtained in a similar manner to that of Preparation 92.

2-methyl-4-pyridin-4-ylaniline

1H-NMR (DMSO-d6): δ 2.13 (3H, s), 5.28 (2H, s), 6.70 (1H, d, J=8.4 Hz), 7.38-7.48 (2H, m), 7.56 (2H, dd, J=1.6, 4.6 Hz), 8.47 (2H, dd, J=1.6, 4.6 Hz)

MS (ESI, m/z): 185 (M+H)

Preparation 97

To a solution of 4-(4-nitrophenyl)pyrimidin-2-amine (1.17 g) in dichloromethane (30 mL) were added di-tert-butyl dicarbonate (3.19 g) and 4-dimethylaminopyridine (66 mg) at ambient temperature and the mixture was stirred for 20 hours. Water (10 mL) was added and the organic layer was washed with brine, dried over magnesium sulfate, and evaporated in vacuo. The residue was purified by column chromatography on silica gel eluting with chloroform/methanol (20:1) to afford di-tert-butyl [4-(4-nitrophenyl)pyrimidin-2-yl]imidodicarbonate (1.72 g) as a powder.

1H-NMR (DMSO-d6): δ 1.41 (18H, s), 8.22 (1H, d, J=5.3 Hz), 8.40-8.47 (4H, m), 9.04 (1H, d, J=5.3 Hz)

MS (ESI, m/z): 439 (M+Na)

Preparation 98

The following compound was obtained in a similar manner to that of Preparation 92.

di-tert-butyl[4-(4-aminophenyl)pyrimidin-2-yl]imidodicarbonate

1H-NMR (DMSO-d6): δ 1.39 (18H, s), 5.91 (2H, s), 6.65 (2H, d, J=8.6 Hz), 7.74 (1H, d, J=5.5 Hz), 7.91 (2H, d, J=8.6 Hz), 8.63 (1H, d, J=5.5 Hz)

MS (ESI, m/z): no data

Preparation 99

The following compound was obtained in a similar manner to that of Preparation 36.

N-(4-{2-[bis(tert-butoxycarbonyl)amino]pyrimidin-4-yl}phenyl)-N-alpha-(tert-butoxycarbonyl)-D-phenylalaninamide 1H-NMR (DMSO-d6): δ1.33-1.4 (27H, m), 2.86 (1H, dd, J=13.5, 9.9 Hz), 3.01 (1H, dd, J=13.5, 4.6 Hz), 4.33-4.39 (1H, m), 7.18-7.21 (2H, m), 7.27-7.34 (4H, m), 7.78 (2H, d J=8.9 Hz), 7.98 (1H, d, J=5.4 Hz), 8.18 (2H, d, J=8.8 Hz), 8.84 (1H, d, J=5.4 Hz), 10.31 (1H, brs)

MS (ESI, m/z): 656 (M+Na)

Preparation 100

The following compound was obtained in a similar manner to that of Preparation 36.

N-(4-{2-[bis(tert-butoxycarbonyl)amino]pyrimidin-4-yl}phenyl)-Nalpha-(tert-butoxycarbonyl)-D-phenylalaninamide 1H-NMR (DMSO-d6): δ 1.32-1.40 (27H, m), 2.81-2.87 (1H, m), 2.98-3.02 (1H, m), 4.30-4.35 (1H, m), 7.09-7.14 (2H, m), 7.21 (1H, d, J=8.1 Hz), 7.36 (2H, dd, J=5.8, 8.2 Hz), 7.78 (2H, d, J=8.8 Hz), 7.98 (1H, d, J=5.4 Hz), 8.18 (2H, d, J=8.9 Hz), 8.84 (1H, d, J=5.4 Hz)

MS (ESI, m/z): 674 (M+Na)

Preparation 101

The following compound was obtained in a similar manner to that of Preparation 36.

N-(4-{2-[bis(tert-butoxycarbonyl)amino]pyrimidin-4-yl}phenyl)-N-alpha-(tert-butoxycarbonyl)-4-chloro-D-phenylalaninamide 1H-NMR (DMSO-d6): δ 1.33-1.40 (27H, m), 2.85 (1H, dd, J=10.4, 13.4 Hz) 3.02 (1H, d, J=4.6, 13.4 Hz), 4.31-4.37 (1H, m), 7.23 (1H, d, J=8.2 Hz) 7.36 (4H, s), 7.79 (2H, d, J=8.8 Hz), 7.98 (1H, d, J=5.3 Hz), 8.19 (2H, d, J=8.8 Hz), 8.85 (1H, d, J=5.3 Hz), 10.38 (1H, br)

MS (ESI, m/z): 691 (M+Na)

Preparation 102

The following compound was obtained in a similar manner to that of Preparation 36.

N-(4-{2-[bis(tert-butoxycarbonyl)amino]pyrimidin-4-yl}phenyl)-N-alpha-(tert-butoxycarbonyl)-O-methyl-D-tyrosinamide 1H-NMR (DMSO-d6): δ 1.33-1.40 (27H, m), 2.79 (1H, dd, J=10.2, 13.6 Hz), 2.95 (1H, dd, J=4.5, 13.6 Hz), 3.71 (3H, s), 4.27-4.32 (1H, m), 6.85 (2H, d, J=8.5 Hz), 7.14 (1H, d, J=7.9 Hz), 7.24 (2H, d, J=8.5 Hz), 7.79 (2H, d, J=8.9 Hz), 7.98 (1H, d, J=5.4 Hz), 8.18 (2H, d, J=8.8 Hz), 8.84 (1H, d, J=5.3 Hz), 10.34 (1H, br)

MS (ESI, m/z): 686 (M+Na)

Preparation 103

The following compound was obtained in a similar manner to that of Preparation 36.

di-tert-butyl[4-(4-{[(2R)-2-morpholin-4-yl-3-phenylpropanoyl]amino}phenyl)pyrimidin-2-yl]imidodicarbonate 1H-NMR (DMSO-d6): δ 1.39 (18H, s), 2.63-2.67 (4H, m), 2.90 (1H, dd, J=5.0, 13.2 Hz), 3.10 (1H, dd, J=9.6, 13.2 Hz), 3.52 (1H, dd, J=5.0, 9.6 Hz), 3.56-3.59 (4H, m), 7.13-7.19 (1H, m), 7.24-7.25 (4H, m), 7.74 (2H, d, J=8.9 Hz), 7.97 (1H, d, J=5.3 Hz), 8.14 (2H, d, J=8.8 Hz), 8.84 (1H, d, J=5.4 Hz), 10.13 (1H, br) MS (ESI, m/z): 604 (M+H)

Preparation 104

The following compound was obtained in a similar manner to that of Preparation 36.

N-alpha-(tert-butoxycarbonyl)-4-cyano-N-[4-(4-pyridinyl)phenyl]-D-phenylalaninamide 1H-NMR (DMSO-d6): δ 1.20-1.36 (9H, m), 2.88-2.99 (1H, m) 3.05-3.15 (1H, m), 4.34-4.44 (1H, m), 7.26 (1H, d, J=8.5 Hz), 7.54 (2H, d, J=8.0 Hz), 7.67-7.84 (8H, m), 8.59-8.62 (2H, m), 10.28 (1H, s)

MS (ESI, m/z): 443 (M+H)

Preparation 105

The following compound was obtained in a similar manner to that of Preparation 36.

N-alpha-(tert-butoxycarbonyl)-O-tert-butyl-N-[4-(4-pyridinyl)phenyl]-D-tyrosinamide 1H-NMR (DMSO-d6): δ 1.23 (9H, s), 1.33 (9H, s), 2.78-2.98 (2H, m), 4.29-4.38 (1H, m), 6.86 (2H, d, J=8.2 Hz), 7.16 (1H, d, J=8.2 Hz), 7.21 (2H, d, J=8.2 Hz), 7.67-7.74 (4H, m), 7.77-7.81 (2H, m), 8.59-8.62 (2H, m), 10.17 (1H, s)

MS (ESI, m/z): 490 (M+H)

Preparation 106

The following compound was obtained in a similar manner to that of Preparation 36.

N-alpha-(tert-butoxycarbonyl)-4-nitro-N-[4-(4-pyridinyl)phenyl]-D-phenylalaninamide 1H-NMR (DMSO-d6): δ 1.20-1.35 (9H, m), 2.94-3.23 (2H, m), 4.26-4.48 (1H, m), 7.29 (1H, d, J=8.5 Hz), 7.64 (2H, d, J=8.5 Hz), 7.68-7.71 (2H, m), 7.76 (2H, d, J=8.8 Hz), 7.82 (2H, d, J=8.8 Hz), 8.19 (2H, d, J=8.6 Hz), 8.59-8.62 (2H, m), 10.41 (1H, s)

MS (ESI, m/z): 463 (M+H)

Preparation 107

The following compound was obtained in a similar manner to that of Preparation 36.

tert-butyl[(1R)-1-benzyl-2-(5-bromo-2,3-dihydro-1H-indol-1-yl)-2-oxoethyl]carbamate 1H-NMR (DMSO-d6): δ1.31 (9H, s), 2.8-2.88 (1H, m), 2.96-3.06 (2H, m), 3.1-3.2 (1H, m), 3.9-3.99 (1H, m), 4.18-4.26 (1H, m), 4.4-4.48 (1H, m), 7.17-7.45 (7H, m), 8.01 (1H, d, J=8.6 Hz)

MS (ESI, m/z): 467 (M+Na)

Preparation 108

The following compound was obtained in a similar manner to that of Preparation 37.

tert-butyl[(1R)-1-benzyl-2-oxo-2-(5-pyridin-4-yl-2,3-dihydro-1H-indol-1-yl)ethyl]carbamate 1H-NMR (DMSO-d6): δ 1.33 (9H, s), 2.81-3.30 (4H, m), 3.82-4.04 (1H, m), 4.22-4.33 (1H, m), 4.44-4.54 (1H, m), 7.16-7.37 (5H, m), 7.45 (1H, d, J=7.8 Hz), 7.64-7.73 (4H, m), 8.15-8.26 (1H, m), 8.56-8.63 (2H, m)

MS (ESI, m/z): 444 (M+H)

Preparation 109

To a solution of tert-butyl[(1S)-1-benzyl-2-(5-bromo-2,3-dihydro-1H-indol-1-yl)-2-oxoethyl]carbamate (1.55 g) and 4,4,4',4',5,5,5',5'-octamethyl-2,2'-bi-1,3,2-dioxaborolane (972 mg) in 1,4-dioxane (6 mL) were added potassium acetate (1.03 g) and dichlorobis(triphenylphosphine) palladium (244 mg) and the mixture was refluxed for 3 hours under nitrogen. The mixture was poured into water and extracted with ethyl acetate. The organic layer was washed with brine, dried over magnesium sulfate, and evaporated in vacuo. The residue was purified by column chromatography on silica gel to afford tert-butyl{(1S)-1-benzyl-2-oxo-2-[5-(4,4,5,5-tetramethyl-1,3,2-dioxaborolan-2-yl)-2,3-dihydro-1H-indol-1-yl]ethyl}carbamate (1.44 g) as a powder.

1H-NMR (DMSO-d6): δ 1.18-1.32 (21H, m), 2.75-2.91 (1H, m), 2.95-3.22 (3H, m), 3.79-4.01 (1H, m), 4.12-4.23 (1H, m), 4.35-4.52 (1H, m), 7.13-7.51 (7H, m), 7.97-8.05 (1H, m)

MS (ESI, m/z): 493 (M+H)

Preparation 110

To a solution of tert-butyl {(1S)-1-benzyl-2-oxo-2-[5-(4,4,5,5-tetramethyl-1,3,2-dioxaborolan-2-yl)-2,3-dihydro-1H-indol-1-yl]ethyl}carbamate (672 mg) and 4-chloro-2-pyrimidinamine (265 mg) in 1,4-dioxane (10 mL) were added 2M sodium carbonate aqueous solution (2.0 mL) and tetrakis (triphenylphosphine) palladium (16 mg) and the mixture was refluxed for 3 hours under nitrogen. The mixture was poured into water and extracted with ethyl acetate. The organic layer was washed with brine, dried over magnesium sulfate, and evaporated in vacuo. The residue was purified by column chromatography on silica gel to afford tert-butyl{(1S)-2-[5-(2-aminopyrimidine-4-yl)-2,3-dihydro-1H-indol-1-yl ]-1-benzyl-2-oxoethyl}carbamate (507 mg) as a powder.

1H-NMR (DMSO-d6): δ 1.33 (9H, s), 2.75-2.91 (1H, m), 2.95-3.22 (3H, m), 3.79-4.01 (1H, m), 4.12-4.23 (1H, m), 4.35-4.52 (1H, m), 6.60 (2H, brs), 7.00-7.40 (6H, m), 7.90-7.96 (2H, m), 7.97-8.05 (1H, m), 8.23-8.28 (1H, m)

MS (ESI, m/z): 460 (M+H)

Preparation 111

The following compound was obtained in a similar manner to that of Preparation 110.

tert-butyl {(1R)-1-benzyl-2-oxo-2-[5-(4,4,5,5-tetramethyl-1,3,2-dioxaborolan-2-yl)-2,3-dihydro-1H-indol-1-yl]ethyl}carbamate 1H-NMR (DMSO-d6): δ 1.18-1.32 (21H, m), 2.75-2.91 (1H, m), 2.95-3.22 (3H, m), 3.79-4.01 (1H, m), 4.12-4.23 (1H, m), 4.35-4.52 (1H, m), 7.13-7.51 (7H, m), 7.97-8.05 (1H, m)

MS (ESI, m/z): 493 (M+H)

Preparation 112

The following compound was obtained in a similar manner to that of Preparation 109.

tert-butyl {(1R)-2-[5-(2-aminopyrimidin-4-yl)-2,3-dihydro-1H-indol-1-yl]-1-benzyl-2-oxoethyl}carbamate 1H-NMR (DMSO-d6): δ 1.33 (9H, s), 2.75-2.91 (1H, m), 2.95-3.22 (3H, m), 3.79-4.01 (1H, m), 4.12-4.23 (1H, m), 4.35-4.52 (1H, m), 6.60 (2H, brs), 7.00-7.40 (6H, m), 7.90-7.96 (2H, m), 7.97-8.05 (1H, m), 8.23-8.28 (1H, m)

MS (ESI, m/z): 460 (M+H))

Preparation 113

The following compound was obtained in a similar manner to that of Preparation 36.

di-tert-butyl {4-[4-({(2S)-2-[(tert-butoxycarbonyl)amino]-2-phenylacetyl}amino)phenyl]pyrimidin-2-yl}imido dicarbonate 1H-NMR (DMSO-d6): δ 1.39-1.40 (27H, m), 5.38 (1H, d, J=8.1 Hz), 7.29-7.38 (4H, m), 7.50-7.52 (2H, m), 7.61 (1H, d, J=7.8 Hz), 7.77 (2H, d, J=8.9 Hz), 7.97 (1H, d, J=5.3 Hz), 8.17 (2H, d, J=8.9 Hz), 8.84 (1H, d, J=5.3 Hz), 10.55 (1H, br)

MS (ESI, m/z): no data

Preparation 114

The following compound was obtained in a similar manner to that of Preparation 36.

di-tert-butyl {4-[4-({(2R)-2-[(tert-butoxycarbonyl)amino]-2-phenylacetyl}amino)phenyl]pyrimidin-2-yl}imido dicarbonate 1H-NMR (DMSO-d6): δ 1.39-1.40 (27H, m), 5.38 (1H, d, J=8.1 Hz), 7.29-7.38 (4H, m), 7.50-7.52 (2H, m), 7.61 (1H, d, J=7.8 Hz), 7.77 (2H, d, J=8.9 Hz), 7.97 (1H, d, J=5.3 Hz), 8.17 (H, d, J=8.9 Hz), 8.84 (1H, d, J=5.3 Hz), 10.55 (1H, br)

MS (ESI, m/z): 642 (M+Na)

Preparation 115

The following compound was obtained in a similar manner to that of Preparation 36.

di-tert-butyl[4-(4-{[(2S)-2-[(tert-butoxycarbonyl)amino]-2-(2-thienyl)acetyl]amino}phenyl)pyrimidin-2-yl]imido dicarbonate 1H-NMR (DMSO-d6) δ 1.39 (18H, s), 2.63-2.67 (4H, m), 2.90 (1H, dd, J=5.0, 13.2 Hz), 3.10 (1H, dd, J=9.6, 13.2 Hz), 3.52 (1H, dd, J=5.0, 9.6 Hz), 3.56-3.59 (4H, m), 7.13-7.19 (1H, m), 7.74 (2H, d, J=8.9 Hz), 7.97 (1H, d, J=5.3 Hz), 8.14 (2H, d, J=8.8 Hz), 8.84 (1H, d, J=5.4 Hz), 10.13 (1H, br)

MS (ESI, m/z): 604 (M+H)

Preparation 116

The following compound was obtained in a similar manner to that of Preparation 36.

di-tert-butyl[4-(4-{[(2S)-2-[(tert-butoxycarbonyl)amino]-2-(2-thienyl)acetyl]amino}phenyl)pyrimidin-2-yl]imido dicarbonate 1H-NMR (DMSO-d6): δ 1.37-1.40 (27H, m), 3.09-3.15 (1H, m), 3.212-3.27 (1H, m), 4.33-4.39 (1H, m), 6.95 (2H, s), 7.25 (1H, d, J=8.1 Hz), 7.34 (1H, dd, J=1.3, 4.7 Hz), 7.79 (2H, d, J=8.9 Hz), 7.98 (1H, d, J=5.4 Hz), 8.18 (2H, d, J=8.8 Hz), 8.84 (1H, d, J=5.3 Hz), 10.42 (1H, br)

MS (ESI, m/z): no data

Preparation 117

The following compound was obtained in a similar manner to that of Preparation 1.

di-tert-butyl[4-(4-{[(4-nitrophenoxy)carbonyl]amino}phenyl)pyrimidin-2-yl]imidodicarbonate 1H-NMR (DMSO-d6): δ 1.41 (18H, s), 7.59 (2H, dd, J=9.0, 2.1 Hz), 7.70 (2H, d, J=8.8 Hz), 8.00 (1H, d, J=5.4 Hz), 8.21 (2H, d, J=8.8 Hz), 8.86 (1H, d, J=5.4 Hz), 10.83 (1H, brs)

MS (ESI, m/z): no data

Preparation 118

The following compound was obtained in a similar manner to that of Example 4.

di-tert-butyl {4-[4-({[(1S)-2-hydroxy-1-phenylethyl]carbamoyl}amino)phenyl]pyrimidin-2-yl}imidodicarbonate 1H-NMR (DMSO-d6): δ 1.39 (18H, s), 3.57-3.70 (2H, m), 4.74-4.79 (1H, m), 5.03 (1H, t, J=5.3 Hz), 6.88 (1H, d, J=7.8 Hz), 7.22-7.27 (1H, m), 7.33-7.34 (4H, m), 7.55 (2H, d, J=8.8 Hz), 7.92 (1H, d, J=5.5 Hz), 8.08 (2H, d, J=8.9 Hz), 8.78 (1H, d, J=5.4 Hz), 9.04 (1H, br)

MS (ESI, m/z): 572 (M+Na)

Preparation 119

A mixture of 1-(1-acetyl-2,3-dihydro-1H-indol-5-yl)ethanone (6.0 g) and N,N-dimethylformamide dimethylacetal (14.2 g) was refluxed at 110° C. for 4 hours and evaporated in vacuo. The residue was triturated with diisopropylether, collected by filtration, and dried in vacuo to afford crude (2E)-1-(1-acetyl-2,3-dihydro-1H-indol-5-yl)-3-(dimethylamino)prop-2-en-1-one (7.4 g). To a solution of crude product in methanol (100 mL) were added guanidine hydrochloride (3.56 g) and potassium tert-butoxide (3.86 g) and the mixture was stirred at 100° C. for 3 hours.

After cooling to ambient temperature, the resultant precipitates were collected by filtration, washed with methanol, and dried in vacuo to afford 4-(1-acetyl-2,3-dihydro-1H-indol-5-yl)pyrimidin-2-amine (2.71 g) as a gray powder.

1H-NMR (DMSO-d6): δ 2.18 (3H, s), 3.20 (2H, d, J=8.8 Hz), 4.15 (2H, d, J=8.8 Hz), 6.55 (2H, brs), 7.06 (1H, d, J=5.3 Hz), 7.90 (1H, d, J=5.3 Hz), 7.96 (1H, s), 8.09 (1H, d, J=8.7 Hz)

MS (ESI, m/z): 255 (M+H)

Preparation 120

To a solution of 4-(1-acetyl-2,3-dihydro-1H-indol-5-yl)pyrimidin-2-amine (1.27 g) in ethanol (60 mL) and 1,4-dioxane (40 mL) was added sodium hydroxide (pellet) (2.8 g) and the mixture was refluxed for 6 hours. The resultant solution was cooled to ambient temperature and neutralized by addition of 1N hydrochloric acid. The mixture was evaporated in vacuo and the residue was extracted with chloroform. The organic layer was washed with brine, dried over magnesium sulfate and evaporated in vacuo to afford crude 4-(2,3-dihydro-1H-indol-5-yl)pyrimidin-2-amine (1.03 g) as a powder.

1H-NMR (DMSO-d6): δ 2.97 (2H, d, J=8.6 Hz), 3.51 (2H, d, J=8.6 Hz), 6.03 (1H, brs), 6.36 (2H, brs), 6.51 (1H, d, J=8.2 Hz), 6.92 (1H, d, J=5.3 Hz), 7.71 (1H, d, J=8.2 Hz), 7.79 (1H, s), 8.13 (1H, d, J=5.3 Hz)

MS (ESI, m/z): 213 (M+H)

Preparation 121

The following compound was obtained in a similar manner to that of Preparation 36.

tert-butyl{(1S)-2-[5-(2-aminopyrimidin-4-yl)-2,3-dihydro-1H-indol-1-yl]-2-oxo-1-phenylethyl}carbamate 1H-NMR (DMSO-d6): δ 1.39 (9H, s), 3.06-3.28 (2H, m), 3.73-3.88 (1H, m), 4.34-4.43 (1H, m), 5.54 (1H, d, J=7.4 Hz), 6.58 (2H, s), 7.06 (1H, d, J=5.2 Hz), 7.30-7.58 (6H, m), 7.91-7.96 (2H, m), 8.16 (1H, d, J=8.3 Hz), 8.25 (1H, d, J=5.2 Hz)

MS (ESI, m/z): 446 (M+H)

Preparation 122

The following compound was obtained in a similar manner to that of Preparation 36.

tert-butyl{(1R)-2-[5-(2-aminopyrimidin-4-yl)-2,3-dihydro-1H-indol-1-yl]-2-oxo-1-phenylethyl}carbamate 1H-NMR (DMSO-d6): δ 1.39 (9H, s), 3.06-3.28 (2H, m), 3.73-3.88 (1H, m), 4.34-4.43 (1H, m), 5.54 (1H, d, J=7.4 Hz), 6.58 (2H, s), 7.06 (1H, d, J=5.2 Hz), 7.30-7.58 (6H, m), 7.91-7.96 (2H, m), 8.16 (1H, d, J=8.3 Hz), 8.25 (1H, d, J=5.2 Hz)

MS (ESI, m/z): 446 (M+H)

Preparation 123

The following compound was obtained in a similar manner to that of Preparation 36.

tert-butyl[(1S)-2-[5-(2-aminopyrimidin-4-yl)-2,3-dihydro-1H-indol-1-yl]-1-(4-fluorobenzyl)-2-oxoethyl]carbamate 1H-NMR (DMSO-d6): δ 1.32 (9H, s), 2.64-2.74 (1H, m), 2.91-3.00 (1H, m), 3.06-3.25 (2H, m), 3.73-3.83 (1H, m), 3.92-4.03 (1H, m), 4.24-4.37 (1H, m), 6.58 (2H, brs), 7.03-7.13 (3H, m), 7.26-7.35 (2H, m), 7.88-7.99 (2H, m), 8.13-8.21 (1H, m), 8.26 (1H, d, J=5.2 Hz)

MS (ESI, m/z): 478 (M+H)

Preparation 124

The following compound was obtained in a similar manner to that of Preparation 36.

tert-butyl[(1R)-1-benzyl-2-(6-bromo-3,4-dihydroquinolin-1(2H)-yl)-2-oxoethyl]carbamate 1H-NMR (DMSO-d6): δ 1.33 (9H, s), 1.62-1.86 (2H, m), 2.56-2.66 (2H, m), 2.72-2.86 (2H, m), 3.82-3.92 (1H, m), 4.76-4.82 (1H, m), 6.76-7.1 (2H, m), 7.1-7.26 (4H, m), 7.32 (1H, d, J=7.9 Hz), 7.36-7.4 (2H, m), 7.42-7.52 (1H, m)

MS (ESI, m/z): 481 (M+Na)

Example 1

To a suspension of [4-(4-pyridinyl)phenyl]amine (100 mg) in N,N-dimethylformamide (4 ml) was added (isocyanatomethyl)benzene (86 mg) and the mixture was stirred at ambient temperature for 2 hours. The mixture was partitioned between ethyl acetate and water. The organic layer was separated, washed with water and brine, dried over sodium sulfate, and evaporated in vacuo. The residue was triturated with ethyl acetate to give 1-benzyl-3-[4-(4-pyridinyl)phenyl]urea (135 mg) as a yellow powder.

1H-NMR (DMSO-d6): δ 4.30 (2H, d, J=6 Hz), 6.67 (1H, t, J=6 Hz), 7.20-7.40 (5H, m), 7.54 (2H, d, J=8 Hz), 7.64 (2H, d, J=6 Hz), 7.71 (2H, d, J=8 Hz), 8.55 (2H, d, J=6 Hz), 8.81 (1H, s)

Example 2

The following compound was obtained in a similar manner to that of Example 1.

1-(4-methoxybenzyl)-3-[4-(4-pyridinyl)phenyl]urea

1H-NMR (DMSO-d6) δ 3.73 (3H, s), 4.24 (2H, d, J=5.8 Hz), 6.63 (1H, t, J=5.8 Hz), 6.90 (2H, d, J=8.6 Hz), 7.24 (2H, d, J=8.6 Hz), 7.55 (2H, d, J=8.6 Hz), 7.66 (2H, dd, J=1.6, 4.6 Hz), 7.72 (2H, d, J=8.6 Hz), 8.57 (2H, dd, J=1.6, 4.6 Hz), 8.77 (1H, s).

MS (ESI, m/z) 334 (M+H)

Example 3

The following compound was obtained in a similar manner to that of Example 1.

1-[(1R)-1-phenylethyl]-3-[4-(4-pyridinyl)phenyl]urea

1H-NMR (DMSO-d6) δ 1.40 (3H, d, J=7.0 Hz), 4.84 (1H, quint, J=7.0 Hz), 7.13 (1H, d, J=7.9 Hz), 7.25 (1H, m), 7.36 (4H, m), 7.62 (2H, d, J=8.9 Hz), 7.99 (2H, d, J=8.9 Hz), 8.29 (2H, d, J=6.8 Hz), 8.82° (2H, d, J=6.8 Hz), 9.32 (1H, s).

MS (ESI, m/z) 318 (M+H)

Example 4

To a solution of 4-nitrophenyl[4-(4-pyridinyl)phenyl]carbamate (7.50 g) and N,N-diisopropylethylamine (5.84 mL) in dichloromethane (150 mL) was added (2S)-2-amino-2-phenylethanol (4.60 g) at ambient temperature and the mixture was stirred at the same temperature for 20 hours. The resulting mixture was concentrated in vacuo and then water (45 mL) and ethyl acetate (45 mL) was added to the residue. The precipitated solid was collected by filtration and washed with water (30 mL×5) to obtain yellow crystals. The crystals were triturated with ethyl acetate (30 mL) to give 1-[(1S)-2-hydroxy-1-phenylethyl]-3-[4-(4-pyridinyl)phenyl]urea (6.1 g) as a slightly yellow crystals.

1H-NMR (DMSO-d6): δ3.54-3.73 (2H, m), 4.73-4.82 (1H, m), 5.02 (1H, t, J=5.0 Hz), 6.80 (1H, d, J=7.8 Hz), 7.20-7.29 (1H, m), 7.30-7.38 (4H, m), 7.52 (2H, d, J=8.5 Hz), 7.65 (2H, d, J=5.4 Hz), 7.72 (2H, d, J=8.5 Hz), 8.56 (2H, d, J=5.4 Hz), 8.92 (1H, s)

MS (ESI, m/z): 334 (M+H)

Example 5

The following compound was obtained in a similar manner to that of Example 4.

1-[(1S)-1-phenylethyl]-3-[4-(4-pyridinyl)phenyl]urea

1H-NMR (DMSO-d6): δ1.39 (3H, d, J=6.8 Hz), 4.83 (1H, quint, J=6.8 Hz), 6.73 (1H, d, J=7.9 Hz), 7.24 (1H, m), 7.35

(4H, d, J=4.4 Hz), 7.51 (2H, d, J=8.7 Hz), 7.65 (2H, d, J=6.2 Hz), 7.71 (2H, d, J=8.7 Hz), 8.55 (2H, d, J=6.2 Hz), 8.65 (1H, s)

MS (ESI, m/z): 318 (M+H)

Example 6

The following compound was obtained in a similar manner to that of Example 4.

1-[(1R)-2-hydroxy-1-phenylethyl]-3-[4-(4-pyridinyl)phenyl]urea

1H-NMR (DMSO-d6): δ3.54-3.73 (2H, m), 4.73-4.83 (1H, m), 5.02 (1H, t, J=5.0 Hz), 6.80 (1H, d, J=7.8 Hz), 7.20-7.40 (5H, m), 7.52 (2H, d, J=8.5 Hz), 7.66 (2H, d, J=5.4 Hz), 7.73 (2H, d, J=8.5 Hz), 8.57 (2H, d, J=5.4 Hz), 8.90 (1H, s)

MS (ESI, m/z): 334 (M+H)

Example 7

The following compound was obtained in a similar manner to that of Example 4.

methyl (2R)-phenyl[({[4-(4-pyridinyl)phenyl]amino}carbonyl)amino]acetate

1H-NMR ($CDCl_3$): δ3.74 (3H, s), 5.28 (1H, s), 5.60 (1H, d, J=8.0 Hz), 7.23 (1H, s), 7.34-7.56 (9H, m), 7.71 (2H, d, J=8.2 Hz), 8.60 (2H, d, J=6.0 Hz)

MS (ESI, m/z): 362 (M+H)

Example 8

The following compound was obtained in a similar manner to that of Example 4.

methyl (2S)-phenyl[({[4-(4-pyridinyl)phenyl]amino}carbonyl)amino]acetate

1H-NMR ($CDCl_3$): δ3.74 (3H, s), 5.28 (1H, s), 5.60 (1H, d, J=8.0 Hz), 7.23 (1H, s), 7.34-7.56 (9H, m), 7.71 (2H, d, J=8.2 Hz), 8.60 (2H, d, J=6.0 Hz)

MS (ESI, m/z): 362 (M+H)

Example 9

The solution of tert-butyl (2S)-phenyl[({[4-(4-pyridinyl)phenyl]amino}carbonyl)amino]acetate (50.0 mg) in dichloromethane (1.0 mL) and trifluoroacetic acid (954 μL) was stand at ambient temperature for 2 hours. The resulting mixture was concentrated in vacuo and the residue was diluted with chloroform (2 mL), then concentrated. To the residue was added ethyl acetate (2.0 mL) and the precipitated solid was collected by filtration, then washed with ethyl acetate (2.0 mL) to give (2S)-phenyl[({[4-(4-pyridinyl)phenyl]amino}carbonyl)amino]acetic acid trifluoroacetate (39 mg) as off-white crystals.

1H-NMR (DMSO-d6): δ5.27 (1H, d, J=7.2 Hz), 7.24 (1H, d, J=7.2 Hz), 7.31-7.45 (5H, m), 7.59 (2H, d, J=8.7 Hz), 7.94 (2H, d, J=8.7 Hz), 8.17 (2H, d, J=6.5 Hz), 8.78 (2H, d, J=6.5 Hz), 9.18 (1H, s)

MS (ESI, m/z): 348 (M+H—$CF_3CO_2H$)

Example 10

The following compound was obtained in a similar manner to that of Example 9.

(2R)-phenyl[({[4-(4-pyridinyl)phenyl]amino}carbonyl)amino]acetic Acid Trifluoroacetate 1H-NMR (DMSO-d6): δ5.27 (1H, d, J=7.2 Hz), 7.24 (1H, d, J=7.2 Hz), 7.31-7.45 (5H, m), 7.59 (2H, d, J=8.7 Hz), 7.94 (2H, d, J=8.7 Hz), 8.17 (2H, d, J=6.5 Hz), 8.78 (2H, d, J=6.5 Hz), 9.18 (1H, s)

MS (ESI, m/z): 348 (M+H—$CF_3CO_2H$)

Example 11

The following compound was obtained in a similar manner to that of Example 4.

(2R)-2-phenyl-2-[({[4-(4-pyridinyl)phenyl]amino}carbonyl)amino]acetamide

1H-NMR (DMSO-d6): δ5.31 (1H, d, J=7.6 Hz), 7.10 (1H, d, J=7.6 Hz), 7.20-7.55 (8H, m), 7.65 (2H, d, J=5.1 Hz), 7.71 (2H, d, J=8.4 Hz), 7.83 (1H, s), 8.56 (2H, d, J=5.1 Hz), 9.08 (1H, s)

MS (ESI, m/z) 347 (M+H)

Example 12

The following compound was obtained in a similar manner to that of Example 4.

(2S)-2-phenyl-2-[({[4-(4-pyridinyl)phenyl]amino}carbonyl)amino]acetamide

1H-NMR (DMSO-d6): δ5.31 (1H, d, J=7.6 Hz), 7.10 (1H, d, J=7.6 Hz), 7.20-7.55 (8H, m), 7.65 (2H, d, J=5.1 Hz), 7.71 (2H, d, J=8.4 Hz), 7.83 (1H, s), 8.56 (2H, d, J=5.1 Hz), 9.08 (1H, s)

MS (ESI, m/z): 347 (M+H)

Example 13

The following compound was obtained in a similar manner to that of Example 4.

1-[(1S)-2,3-dihydro-1H-inden-1-yl]-3-[4-(4-pyridinyl)phenyl]urea

1H-NMR (DMSO-d6): δ1.81 (1H, m), 2.49 (1H, m), 2.81 (1H, m), 2.91 (1H, m), 5.19 (1H, q, J=7.7 Hz), 6.61 (1H, d, J=7.7 Hz), 7.26 (4H, m), 7.57 (2H, d, J=8.6 Hz), 7.67 (2H, d, J=5.5 Hz), 7.74 (2H, d, J=8.6 Hz), 8.57 (2H, d, J=5.5 Hz), 8.65 (1H, s)

MS (ESI, m/z): 330 (M+H)

Example 14

The following compound was obtained in a similar manner to that of Example 4.

1-[(1R)-2,3-dihydro-1H-inden-1-yl]-3-[4-(4-pyridinyl)phenyl]urea

1H-NMR (DMSO-d6): δ1.78 (1H, m), 2.45 (1H, m), 2.84 (1H, m), 2.93 (1H, m), 5.19 (1H, q, J=8.1 Hz), 6.61 (1H, d, J=8.1 Hz), 7.26 (4H, m), 7.57 (2H, d, J=8.6 Hz), 7.67 (2H, d, J=5.7 Hz), 7.74 (2H, d, J=8.6 Hz), 8.57 (2H, d, J=5.7 Hz), 8.65 (1H, s)

MS (ESI, m/z): 330 (M+H)

Example 15

The following compound was obtained in a similar manner to that of Example 4.

N-[4-(4-pyridinyl)phenyl]-3,4-dihydro-2(1H)-isoquinolinecarboxamide

1H-NMR (DMSO-d6): δ2.87 (2H, t, J=5.8 Hz), 3.72 (2H, t, J=5.8 Hz), 4.66 (2H, s), 7.20 (4H, s), 7.67 (4H, m), 7.74 (2H, d, J=8.8 Hz), 8.57 (2H, dd, J=1.6, 4.6 Hz), 8.81 (1H, s)

MS (ESI, m/z): 330 (M+H)

Example 16

The following compound was obtained in a similar manner to that of Example 4.

1-(cyclohexylmethyl)-3-[4-(4-pyridinyl)phenyl]urea

1H-NMR (DMSO-d6): δ0.92 (2H, m), 1.18 (3H, m), 1.39 (1H, m), 1.69 (5H, m), 2.95 (2H, t, J=5.7 Hz), 6.25 (1H, t, J=5.7 Hz), 7.52 (2H, d, J=8.8 Hz), 7.65 (2H, d, J=5.8 Hz), 7.71 (2H, d, J=8.8 Hz), 8.56 (2H, d, J=5.8 Hz), 8.62 (1H, s)

MS (ESI, m/z): 310 (M+H)

Example 17

The following compound was obtained in a similar manner to that of Example 4.

1-[(1S)-1-cyclohexylethyl]-3-[4-(4-pyridinyl)phenyl]urea

1H-NMR (DMSO-d6): δ0.90-1.35 (9H, m), 1.64 (5H, m), 3.55 (1H, m), 6.09 (1H, d, J=9.1 Hz), 7.51 (2H, d, J=8.4 Hz), 7.65 (2H, d, J=5.0 Hz), 7.71 (2H, d, J=8.4 Hz), 8.55 (3H, m)

MS (ESI, m/z): 324 (M+H)

Example 18

The following compound was obtained in a similar manner to that of Example 4.

1-[(1R)-1-cyclohexylethyl]-3-[4-(4-pyridinyl)phenyl]urea

1H-NMR (DMSO-d6): δ0.90-1.35 (9H, m), 1.70 (5H, m), 3.52 (1H, m), 6.09 (1H, d, J=8.4 Hz), 7.51 (2H, d, J=8.1 Hz), 7.65 (2H, d, J=3.5 Hz), 7.71 (2H, d, J=8.1 Hz), 8.55 (3H, m).

MS (ESI, m/z): 324 (M+H)

Example 19

The following compound was obtained in a similar manner to that of Example 4.

N-[4-(4-pyridinyl)phenyl]octahydro-2(1H)-isoquinoline carboxamide

1H-NMR (DMSO-d6): δ1.18-1.89 (12H, m), 4.37 (4H, m), 7.61 (2H, d, J=8.8 Hz), 7.66 (2H, dd, J=1.5, 4.5 Hz), 7.71 (2H, d, J=8.8 Hz), 8.57 (2H, dd, J=1.5, 4.5 Hz), 8.60 (0.82H, s), 8.66 (0.18H, s)

MS (ESI, m/z): 336 (M+H)

Example 20

A solution of 1H-indole-3-carbonyl azide (82.0 mg) in dioxane (1.5 mL) was stirred at 90° C. for 4 hours, then [4-(4-pyridinyl)phenyl]amine (50.0 mg) was added to the mixture at 0° C. The mixture was stirred at ambient temperature overnight and the solvent was evaporated in vacuo. The residue was dissolved in chloroform (3.0 mL) and the organic layer was washed successively with saturated sodium bicarbonate aqueous solution and brine. The solvent was evaporated in vacuo to afford 1-(1H-indol-3-yl)-3-[4-(4-pyridinyl)phenyl]urea (46.6 mg) as white crystals.

1H-NMR (DMSO-d6): δ7.02 (1H, t, J=7.4 Hz), 7.09 (1H, t, J=7.4 Hz), 7.35 (1H, d, J=7.7 Hz), 7.53 (2H, m), 7.66 (4H, m), 7.77 (2H, m), 8.58 (3H, s), 8.88 (1H, s), 10.77 (1H, s)

MS (ESI, m/z): 329 (M+H)

Example 21

The following compound was obtained in a similar manner to that of Example 20.

1-(1-benzofuran-2-yl)-3-[4-(4-pyridinyl)phenyl]urea

1H-NMR (DMSO-d6): δ6.51 (1H, s), 7.17 (2H, m), 7.47 (2H, m), 7.65 (2H, d, J=8.6 Hz), 7.70 (2H, d, J=5.8 Hz), 7.81 (2H, d, J=8.6 Hz), 8.60 (2H, d, J=5.8 Hz), 9.09 (1H, s), 9.83 (1H, s)

MS (ESI, m/z): 330 (M+H)

Example 22

The following compound was obtained in a similar manner to that of Example 4.

1-(1,3-benzothiazol-2-yl)-3-[4-(4-pyridinyl)phenyl]urea

1H-NMR (DMSO-d6): δ7.26 (1H, t, J=7.8 Hz), 7.40 (1H, t, J=7.8 Hz), 7.70 (6H, m), 7.83 (2H, d, J=8.8 Hz), 7.91 (1H, d, J=7.5 Hz), 8.61 (2H, dd, J=1.5, 4.4 Hz), 9.44 (1H, s)

MS (ESI, m/z): 347 (M+H)

Example 23

To a suspension of 4-(4-pyridinyl)aniline (50 mg) in dichloromethane (1.50 mL) and pyridine (356.4 μL) was added dropwise benzyloxycarbonyl chloride (75.5 μL) at ambient temperature and the mixture was stirred at the same temperature for 1 hour. The resulting mixture was concentrated in vacuo and water (10 mL) was added to the residue. The aqueous solution was extracted with ethyl acetate (15 mL) and the organic layer was washed successively with saturated sodium bicarbonate aqueous solution and brine, then dried and concentrated. The residual solid was triturated with diisopropylether (2.0 mL) to give benzyl [4-(4-pyridinyl)phenyl]carbamate (70.3 mg) as a yellow solid.

1H-NMR (DMSO-d6): δ5.18 (2H, s), 7.33-7.48 (5H, m), 7.63 (2H, d, J=8.7 Hz), 7.68 (2H, d, J=6.3 Hz), 7.78 (2H, d, J=8.7 Hz), 8.59 (2H, d, J=6.3 Hz)

MS (ESI, m/z): 305 (M+H)

Example 24

The following compound was obtained in a similar manner to that of Preparation 7.

3-phenyl-N-[4-(4-pyridinyl)phenyl]propanamide

1H-NMR (DMSO-d6): δ2.66 (2H, t, J=7.9 Hz), 2.93 (2H, t, J=7.9 Hz), 7.15-7.23 (1H, m), 7.24-7.33 (4H, m), 7.68 (2H, d, J=5.9 Hz), 7.74 (2H, d, J=8.8 Hz), 7.78 (2H, d, J=8.8 Hz), 8.59 (2H, d, J=5.9 Hz), 10.13 (1H, s)

MS (ESI, m/z): 303 (M+H)

Example 25

The following compound was obtained in a similar manner to that of Preparation 7.

2-phenoxy-N-[4-(4-pyridinyl)phenyl]acetamide

1H-NMR (DMSO-d6): δ4.74 (2H, s), 6.93-7.07 (3H, m), 7.27-7.39 (2H, m), 7.70 (2H, d, J=4.7 Hz), 7.77-7.88 (4H, m), 8.60 (2H, d, J=4.7 Hz), 10.30 (1H, s)

MS (ESI, m/z): 305 (M+H)

Example 26

To a mixture of 2-anilino-N-[4-(4-pyridinyl)phenyl]acetamide (5.03 g) in tetrahydrofuran (100.6 ml) was added 1N hydrochloric acid (16.5 mL) at ambient temperature and stirred at ambient temperature for 1 hour. Tetrahydrofuran (300 mL) was added to the mixture and the mixture was cooled with ice bath stirring for 20 minutes. The crystals were collected by filtration and washed with ethyl acetate (50 mL) to afford 2-anilino-N-[4-(4-pyridinyl)phenyl]acetamide hydrochloride (5.00 g) as yellow crystals.

1H-NMR (DMSO-d6): δ3.95 (2H, s), 6.60 (1H, t, J=7.1 Hz), 6.64 (2H, d, J=7.1 Hz), 7.11 (2H, t, J=7.1 Hz), 7.90 (2H, d, J=8.8 Hz), 8.06 (2H, d, J=8.8 Hz), 8.34 (2H, d, J=7.0 Hz), 8.88 (2H, d, J=7.0 Hz), 10.60 (1H, s)

MS (ESI, m/z): 304 (M+H)

Example 27

To a solution of 2-anilino-N-[4-(4-pyridinyl)phenyl]acetamide (50 mg) in N,N-dimethylformamide (1.0 mL) were added triethylamine (0.092 mL) and acetyl chloride (0.0352 mL) at ambient temperature and the mixture was stirred at ambient temperature overnight. Water (3 mL) was added to the mixture and the resulting mixture was extracted with ethyl acetate (5 mL). The organic layer was washed with brine and dried over magnesium sulfate. The solvent was evaporated in vacuo and the residue was purified by preparative thin-layer chromatography (10% methanol in chloroform) to afford 2-[acetyl(phenyl)amino]-N-[4-(4-pyridinyl)phenyl]acetamide (46.9 mg) as a white amorphous.

1H-NMR (DMSO-d6): δ1.84 (3H, s), 4.43 (2H, s), 7.38 (1H, m), 7.47 (4H, m), 7.69 (2H, d, J=6.2 Hz), 7.73 (2H, d, J=8.8 Hz), 7.80 (2H, d, J=8.8 Hz), 8.59 (2H, d, J=6.2 Hz), 10.25 (1H, s)

MS (ESI, m/z): 346 (M+H)

Example 28

To a mixture of ethyl[(2-oxo-2-{[4-(4-pyridinyl)phenyl]amino}ethyl)(phenyl)amino]acetate (40.8 mg) in methanol (0.60 mL) was added 1N sodium hydroxide aqueous solution (0.157 mL) at ambient temperature and the mixture was stirred at ambient temperature overnight. The mixture was neutralized with 1N hydrochloric acid and the precipitate was collected by filtration. The solid was washed with n-hexane/ethyl acetate (1:1, 1.0 mL) to afford [(2-oxo-2-{[4-(4-pyridinyl)phenyl]amino}ethyl) (phenyl)amino]acetic acid (24.8 mg) as white crystals.

1H-NMR (DMSO-d6): δ4.23 (2H, s), 4.33 (2H, s), 6.55 (2H, d, J=7.9 Hz), 6.72 (1H, t, J=7.9 Hz), 7.21 (2H, t, J=7.9 Hz), 7.68 (2H, d, J=6.0 Hz), 7.73 (2H, d, J=8.6 Hz), 7.80 (2H, d, J=8.6 Hz), 8.60 (2H, d, J=6.0 Hz), 10.67 (1H, s)

MS (ESI, m/z): 362 (M+H)

Example 29

To a suspension of N-[4-(4-pyridinyl)phenyl]-1-tert-butoxycarbonylindoline-2-carboxamide (100 mg) in ethyl acetate (0.60 mL) was added 4N hydrogen chloride-ethyl acetate (2.41 mL) and the mixture was stirred at ambient temperature for 1.5 hours. The resulting mixture was diluted with n-hexane (6.0 mL) and the solid was collected by filtration, and then washed with ethyl acetate/n-hexane (1:2, 1.0 mL) to give N-[4-(4-pyridinyl)phenyl]indoline-2-carboxamide (80 mg) as off-white crystals.

1H-NMR (DMSO-d6): δ3.21 (1H, dd, J=7.2, 16.3 Hz), 3.49 (1H, dd, J=10.1, 16.3 Hz), 4.67 (1H, dd, J=7.2, 10.1 Hz), 6.83 (1H, dd, J=7.3, 7.5 Hz), 6.85 (1H, d, J=7.8 Hz), 7.10 (1H, dd, J=7.5, 7.8 Hz), 7.16 (1H, d, J=7.3 Hz), 7.97 (2H, d, J=9.0 Hz), 8.11 (2H, d, J=9.0 Hz), 8.41 (2H, d, J=6.9 Hz), 8.92 (2H, d, J=6.9 Hz), 10.84 (1H, s)

MS (ESI, m/z): 316 (M+H-2HCl)

Example 30

The following compound was obtained in a similar manner to that of Example 29.

2-amino-N-(2-oxo-2-{[4-(4-pyridinyl)phenyl]amino}ethyl)-N-phenylacetamide

1H-NMR ($CDCl_3$): δ3.29 (2H, s), 4.46 (2H, s), 7.30 (2H, m), 7.43 (3H, m), 7.48 (2H, dd, J=4.6 Hz), 7.61 (2H, d, J=8.2 Hz), 7.68 (2H, d, J=8.2 Hz), 8.64 (2H, d, J=4.6 Hz), 8.69 (1H, s)

MS (ESI, m/z): 361 (M+H)

Example 31

To a solution of 2-anilino-N-[4-(4-pyridinyl)phenyl]acetamide (40.0 mg) in dichloromethane (0.80 mL) were added pyridine (0.0533 mL) and methylsulfonyl chloride (0.0204 mL) at 0° C. and the mixture was stirred at ambient temperature for 2 days. Water (4.0 mL) was added to the mixture at ambient temperature and the mixture was extracted with ethyl acetate (6.0 mL). The organic layer was washed successively with saturated sodium bicarbonate aqueous solution and brine, dried over magnesium sulfate and concentrated in vacuo. The residue was purified by preparative thin-layer chromatography (4% methanol in chloroform) to afford 2-[(methylsulfonyl)(phenyl)amino]-N-[4-(4-pyridinyl)phenyl]acetamide (31.4 mg) as white crystals.

1H-NMR ($CDCl_3$): δ3.08 (3H, s), 4.52 (2H, s), 7.37-7.53 (7H, m), 7.64 (4H, m), 8.16 (1H, s), 8.64 (2H, d, J=6.0 Hz)

MS (ESI, m/z): 382 (M+H)

Example 32

The following compound was obtained in a similar manner to that of Preparation 7.

2-[methyl(phenyl)amino]-N-[4-(4-pyridinyl)phenyl]acetamide

1H-NMR ($CDCl_3$): δ3.11 (3H, s), 3.99 (2H, s), 6.86 (2H, d, J=7.9 Hz), 6.92 (1H, t, J=7.5 Hz), 7.32 (2H, dd, J=7.5, 7.9 Hz), 7.48 (2H, dd, J=1.7, 4.4 Hz), 7.64 (4H, m), 8.56 (1H, s), 8.63 (2H, dd, J=1.7, 4.4 Hz)

MS (ESI, m/z): 318 (M+H)

Example 33

The following compound was obtained in a similar manner to that of Example 28.

2-[glycoloyl(phenyl)amino]-N-[4-(4-pyridinyl)phenyl]acetamide

1H-NMR ($CDCl_3$): δ3.96 (2H, s), 4.49 (2H, s), 7.33 (2H, m), 7.47 (5H, m), 7.62 (2H, d, J=8.9 Hz), 7.67 (2H, d, J=8.9 Hz), 8.43 (1H, s), 8.64 (2H, dd, J=1.6, 4.6 Hz)

MS (ESI, m/z): 390 (M+H)

Example 34

Ethyl[(2-oxo-2-{[4-(4-pyridinyl)phenyl]amino}ethyl)(phenyl)amino]acetate (50.0 mg) was dissolved in methanol/tetrahydrofuran (1:1, 1.0 mL) and sodium borohydride (14.6 mg) was added portionwise to the mixture cooled with ice bath stirring. The mixture was stirred at 0° C. for 5 hours and water (2.0 mL) was added to the resulting mixture. The mixture was neutralized with 1N hydrochloric acid and extracted with ethyl acetate (3.0 mL). The organic layer was washed with brine and dried over magnesium sulfate. The solvent was evaporated in vacuo and the residue was purified by silica gel column chromatography (2 g, 10% methanol in chloroform) to afford 2-[(2-hydroxyethyl) (phenyl)amino]-N-[4-(4-pyridinyl)phenyl]acetamide (21.4 mg) as white crystals.

1H-NMR ($CDCl_3$): δ3.00 (1H, s), 3.70 (2H, t, J=4.9 Hz), 4.04 (2H, t, J=4.9 Hz), 4.07 (2H, s), 6.79 (2H, d, J=8.6 Hz), 6.85 (1H, t, J=7.1 Hz), 7.28 (2H, dd, J=7.1, 8.6 Hz), 7.43 (2H, dd, J=1.5, 5.0 Hz), 7.54 (2H, d, J=8.6 Hz), 7.68 (2H, d, J=8.6 Hz), 8.57 (2H, dd, J=1.5, 5.0 Hz), 9.82 (1H, s)

MS (ESI, m/z): 348 (M+H)

Example 35

To a suspension of (2S)-2-anilino-3-tert-butoxy-N-[4-(4-pyridinyl)phenyl]propanamide (70 mg) in ethyl acetate (0.42 mL) was added 4N hydrogen chloride-ethyl acetate (1.8 mL) and the mixture was stirred at ambient temperature for 5 hours. The resulting mixture was diluted with n-hexane (2.5 mL) and the solid was collected by filtration and washed with n-hexane (2.5 mL) to give (2S)-2-anilino-3-hydroxy-N-[4-(4-pyridinyl)phenyl]propanamide dihydrochloride (72 mg) as an off-white solid.

1H-NMR (DMSO-d6): δ3.74-3.87 (2H, m), 4.17 (1H, t, J=5.5 Hz), 5.60-5.97 (2H, br), 6.64 (1H, t, J=7.2 Hz), 6.74 (2H, d, J=7.8 Hz), 7.12 (2H, dd, J=7.2, 7.8 Hz), 7.93 (2H, d, J=8.7 Hz), 8.07 (2H, d, J=8.7 Hz), 8.39 (2H, d, J=6.6 Hz), 8.90 (2H, d, J=6.6 Hz), 10.67 (1H, s)

MS (ESI, m/z): 334 (M+H-2HCl)

Example 36

The following compound was obtained in a similar manner to that of Example 29.

(2S)-2-(benzylamino)-N-[4-(4-pyridinyl)phenyl]propanamide Dihydrochloride

1H-NMR (DMSO-d6) δ 1.62 (3H, d, J=7.0 Hz), 4.26-4.12 (3H, m), 7.45-7.43 (4H, m), 7.60-7.58 (2H, m), 7.93 (2H, d, J=8.5 Hz), 8.10 (2H, d, J=8.5 Hz), 8.35 (2H, d, J=6.5 Hz), 8.92 (2H, d, J=6.5 Hz)

Example 37

The following compound was obtained in a similar manner to that of Preparation 7.

(2S)-2-anilino-N-[4-(4-pyridinyl)phenyl]propanamide dihydrochloride

1H-NMR (DMSO-d6): δ1.43 (3H, d, J=7.0 Hz), 4.08-4.03 (1H, m), 6.56 (1H, dd, J=7.5, 7.5 Hz), 6.62 (2H, d, J=8.0 Hz), 7.08 (2H, dd, J=8.0, 8.0 Hz), 7.67 (2H, d, J=6.0 Hz), 7.79 (4H, m), 8.59 (2H, d, J=6.0 Hz)

Example 38

The following compound was obtained in a similar manner to that of Preparation 7.

(2R)-2-anilino-N-[4-(4-pyridinyl)phenyl]propanamide

1H-NMR (DMSO-d6): δ1.43 (3H, d, J=7.0 Hz), 4.08-4.01 (1H, m), 6.56 (2H, dd, J=7.5, 7.5 Hz), 6.62 (2H, d, J=8.0 Hz), 7.08 (2H, dd, J=8.0, 8.0 Hz), 7.68 (2H, d, J=6.0 Hz), 7.78 (4H, m), 8.59 (2H, d, J=6.0 Hz)

MS (ESI, m/z): 318 (M+H)

Example 39

The following compound was obtained in a similar manner to that of Example 35.

(2R)-2-anilino-3-hydroxy-N-[4-(4-pyridinyl)phenyl]propanamide Dihydrochloride

1H-NMR (DMSO-d6) δ3.74-3.87 (2H, m), 4.17 (1H, t, J=5.5 Hz), 5.63-5.99 (2H, br), 6.64 (1H, t, J=7.2 Hz), 6.74 (2H, d, J=7.8 Hz), 7.12 (2H, dd, J=7.2, 7.8 Hz), 7.93 (2H, d, J=8.7 Hz), 8.07 (2H, d, J=8.7 Hz), 8.39 (2H, d, J=6.6 Hz), 8.90 (2H, d, J=6.6 Hz), 10.67 (1H, s)

MS (ESI, m/z): 334 (M+H-2HCl)

Example 40

The following compound was obtained in a similar manner to that of Preparation 7.

(2S)-2-anilino-3-methyl-N-[4-(4-pyridinyl)phenyl]butanamide

1H-NMR ($CDCl_3$): δ1.09 (3H, d, J=7.2 Hz), 1.13 (3H, d, J=7.2 Hz), 2.45-2.58 (1H, m), 3.69 (1H, dd, J=2.9, 3.6 Hz), 3.98 (1H, d, J=2.9 Hz), 6.72 (2H, d, J=7.5 Hz), 6.86 (1H, t,

J=7.3 Hz), 7.24 (2H, dd, J=7.3, 7.5 Hz), 7.47 (2H, d, J=6.0 Hz), 7.60 (2H, d, J=9.0 Hz), 7.67 (2H, d, J=9.0 Hz), 8.63 (2H, d, J=6.0 Hz), 8.82 (1H, s)

MS (ESI, m/z): 346 (M+H)

Example 41

The following compound was obtained in a similar manner to that of Preparation 7.

(2R)-2-anilino-3-methyl-N-[4-(4-pyridinyl)phenyl] butanamide

1H-NMR ($CDCl_3$): δ1.09 (3H, d, J=7.2 Hz), 1.13 (3H, d, J=7.2 Hz), 2.45-2.58 (1H, m), 3.69 (1H, dd, J=2.9, 3.6 Hz), 3.98 (1H, d, J=2.9 Hz), 6.72 (2H, d, J=7.5 Hz), 6.86 (1H, t, J=7.3 Hz), 7.24 (2H, dd, J=7.3, 7.5 Hz), 7.47 (2H, d, J=6.0 Hz), 7.60 (2H, d, J=9.0 Hz), 7.67 (2H, d, J=9.0 Hz), 8.63 (2H, d, J=6.0 Hz), 8.82 (1H, s)

MS (ESI, m/z): 346 (M+H)

Example 42

The following compound was obtained in a similar manner to that of Preparation 7.

tert-butyl((1S,2R)-2-hydroxy-3-oxo-1-phenyl-3-{[4-(4-pyridinyl)phenyl]amino}propyl)carbamate 1H-NMR (DMSO-d6): δ1.31 (9H, s), 4.25-4.33 (1H, m), 5.00-5.07 (1H, m), 5.88 (1H, d, J=7.1 Hz), 7.07 (1H, d, J=9.1 Hz), 7.20-7.40 (5H, m), 7.69 (2H, d, J=6.3 Hz), 7.74-7.83 (4H, m), 8.60 (2H, d, J=6.3 Hz), 10.00 (1H, s)

MS (ESI, m/z): 434 (M+H)

Example 43

The following compound was obtained in a similar manner to that of Preparation 7.

N-[4-(4-pyridinyl)phenyl]-2-quinolinecarboxamide

1H-NMR (DMSO-d6): δ7.77 (3H, m), 7.92 (3H, m), 8.15 (3H, m), 8.29 (2H, m), 8.64 (3H, m), 10.96 (1H, s)

MS (ESI, m/z): 326 (M+H)

Example 44

The following compound was obtained in a similar manner to that of Preparation 7.

2-(1H-indol-1-yl)-N-[4-(4-pyridinyl)phenyl]acetamide

1H-NMR (DMSO-d6): δ5.11 (2H, s), 6.47 (1H, d, J=3.1 Hz), 7.04 (1H, t, J=7.0 Hz), 7.13 (1H, t, J=7.0 Hz), 7.40 (1H, d, J=3.1 Hz), 7.44 (1H, d, J=7.0 Hz), 7.57 (1H, d, J=7.0 Hz), 7.69 (2H, dd, J=1.7, 4.6 Hz), 7.75 (2H, d, J=8.8 Hz), 7.82 (2H, d, J=8.8 Hz), 8.60 (2H, dd, J=1.7, 4.6 Hz), 10.60 (1H, s)

MS (ESI, m/z): 328 (M+H)

Example 45

To a mixture of 1H-pyrrole-2-carboxylic acid (45.0 mg) in dichloromethane (1.8 mL) were added oxalyl chloride (0.053 mL) and one-drop of N,N-dimethylformamide at 0° C. After 15 minutes, [4-(4-pyridinyl)phenyl]amine (68.9 mg) and pyridine (0.131 mL) were added to the mixture at 0° C. and the resulting mixture was stirred at ambient temperature overnight. Water (3 mL) was added to the mixture. The precipitate was collected by filtration and washed with water (2 mL) to afford N-[4-(4-pyridinyl)phenyl]-1H-pyrrole-2-carboxamide (65.2 mg) as white crystals.

1H-NMR (DMSO-d6): δ6.19 (1H, m), 7.00 (1H, m), 7.11 (1H, m), 7.73 (2H, d, J=4.6 Hz), 7.83 (2H, d, J=8.8 Hz), 7.92 (2H, d, J=8.8 Hz), 8.61 (2H, d, J=4.6 Hz), 9.94 (1H, s), 11.74 (1H, s)

MS (ESI, m/z): 264 (M+H)

Example 46

The following compound was obtained in a similar manner to that of Example 45.

1-methyl-N-[4-(4-pyridinyl)phenyl]-1H-pyrrole-2-carboxamide

1H-NMR (DMSO-d6): δ3.90 (3H, s), 6.11 (1H, dd, J=2.6, 3.8 Hz), 7.04 (1H, m), 7.07 (1H, m), 7.71 (2H, d, J=6.0 Hz), 7.81 (2H, d, J=8.6 Hz), 7.89 (2H, d, J=8.6 Hz), 8.60 (2H, d, J=6.0 Hz), 9.93 (1H, s)

MS (ESI, m/z): 278 (M+H)

Example 47

To a solution of 5-bromo-1-(phenylacetyl)indoline (15.98 g) and 4-(4,4,5,5-tetramethyl-1,3,2-dioxaborolan-2-yl)pyridine (12.4 g) in 1,2-dimethoxyethane (500 mL) were added [1,1'-bis-(diphenylphosphino)ferrocene]dichloropalladium (II), complex with dichloromethane (1.24 g) and potassium phosphate (32.2 g) at ambient temperature and the mixture was stirred at 100° C. for 60 hours. The mixture was evaporated in vacuo to remove 1,2-dimethoxyethane and the residue was dissolved in a mixture of ethyl acetate (600 mL) and water (300 mL). The separated organic layer was washed with brine, dried over magnesium sulfate, and evaporated in vacuo. The residue was purified by column chromatography on silica gel eluting with ethyl acetate to give 1-(phenylacetyl)-5-(4-pyridinyl)indoline (8.02 g) as a white powder.

1H-NMR (DMSO-d6): δ3.24 (6.8H, t), 3.88 (2H, s), 4.24 (6.8H, t), 7.2-7.4 (5H, m), 7.6-7.75 (4H, m), 8.16 (1H, d, J=6.9 Hz), 8.55-8.65 (2H, m)

ESI-MS (m/z): 315 (M+H)

Example 48

The following compound was obtained in a similar manner to that of Example 47.

5-(4-pyridinyl)-1-(2-pyridinylacetyl)indoline

1H-NMR (DMSO-d6): δ3.25 (2H, t, J=6.8 Hz), 4.06 (2H, s), 4.76 (2H, t, J=6.8 Hz), 7.25-7.7 (7H, m), 8.15 (1H, d, J=8.1 Hz), 8.51 (1H, d, J=4.7 Hz), 8.57 (2H, d, J=6.0 Hz)

ESI-MS (m/z): 316 (M+H)

Example 49

To a solution of 5-(4-pyridinyl)indoline (80 mg) in acetonitrile (10 mL) was added phenyl isocyanate (53 mg) and the mixture was stirred at 80° C. for 6 hours. The mixture was evaporated to dryness and the residue was purified by column chromatography on silica gel eluting with ethyl acetate/ methanol (10:1) to give N-phenyl-5-(4-pyridinyl)-1-indolinecarboxamide (60 mg) as a light-brown powder.

1H-NMR (DMSO-d6): δ3.37 (2H, t, J=6.8 Hz), 4.20 (2H, t, J=6.8 Hz), 7.0-7.1 (1H, m), 7.25-7.35 (2H, m), 7.55-7.65 (4H, m), 7.68 (2H, d, J=6.0 Hz), 7.98 (1H, d, J=8.1 Hz), 8.56 (2H, d, J=6.0 Hz), 8.61 (1H, s)

ESI-MS (m/z): 316 (M+H)

Example 50

The following compound was obtained in a similar manner to that of Example 4.

N-benzyl-5-(4-pyridinyl)-1-indolinecarboxamide

1H-NMR (DMSO-d6): δ3.22 (2H, t, J=8.6 Hz), 4.02 (2H, t, J=8.6 Hz), 4.36 (2H, d, J=5.8 Hz), 7.19-7.28 (1H, m), 7.29-7.42 (5H, m), 7.59 (1H, dd, J=1.8, 8.6 Hz), 7.63-7.69 (3H, m), 7.93 (1H, d, J=8.6 Hz), 8.55 (2H, d, J=6.3 Hz)

MS (ESI, m/z): 330 (M+H)

Example 51

The following compound was obtained in a similar manner to that of Example 4.

N-[(1S)-2-hydroxy-1-phenylethyl]-5-(4-pyridinyl)-1-indolinecarboxamide

1H-NMR (DMSO-d6): δ3.23 (2H, t, J=8.6 Hz), 3.57-3.74 (2H, m), 4.10 (2H, t, J=8.6 Hz), 4.83-4.95 (1H, m), 4.92 (1H, t, J=5.9 Hz), 6.88 (1H, d, J=7.8 Hz), 7.23 (1H, t, J=7.1 Hz), 7.32 (2H, t, J=7.1 Hz), 7.39 (2H, d, J=7.1 Hz), 7.57 (1H, d, J=8.5 Hz), 7.64 (2H, d, J=5.6 Hz), 7.65 (1H, s), 7.87 (1H, d, J=8.5 Hz), 8.54 (2H, d, J=5.6 Hz)

MS (ESI, m/z): 360 (M+H)

Example 52

The following compound was obtained in a similar manner to that of Example 29.

N-{2-oxo-2-[5-(4-pyridinyl)-2,3-dihydro-1H-indol-1-yl]ethyl}aniline Dihydrochloride 1H-NMR (DMSO-d6): δ3.31 (2H, t, J=8.4 Hz), 4.20 (2H, s), 4.31 (2H, t, J=8.4 Hz), 6.72 (1H, t, J=7.2 Hz), 6.84 (2H, d, J=8.0 Hz), 7.17 (2H, dd, J=7.2, 8.0 Hz), 7.99 (1H, d, J=8.5 Hz), 8.05 (1H, s), 8.22 (1H, d, J=8.5 Hz), 8.39 (2H, d, J=6.9 Hz), 8.90 (2H, d, J=6.9 Hz)

MS (ESI, m/z): 330 (M+H-2HCl)

Example 53

To a solution of tert-butyl[(1S)-1-benzyl-2-oxo-2-{[4-(4-pyridinyl)phenyl]amino}ethyl]carbamate (800 mg) in ethanol (30 mL) was added 4N hydrogen chloride in ethyl acetate (5 mL) and the mixture was stirred at 60° C. for 1 hour. The solvents were removed by evaporation in vacuo and the residue was recrystallized from 2-propanol to afford (2S)-2-amino-3-phenyl-N-[4-(4-pyridinyl)phenyl]propanamide dihydrochloride (625 mg) as a white powder.

1H-NMR (DMSO-d6) δ 3.1-3.3 (2H, m), 4.35-4.5 (1H, m), 7.2-7.4 (5H, m), 7.87 (2H, d, J=8.8 Hz), 8.07 (2H, d, J=8.8 Hz), 8.33 (2H, d, J=6.8 Hz), 8.54 (3H, br), 8.90 (2H, d, J=6.8 Hz)

MS (ESI, m/z) 318 (M+H, free form)

Example 54

The following compound was obtained in a similar manner to that of Example 53.

(2R)-2-amino-3-phenyl-N-[4-(4-pyridinyl)phenyl]propanamide

1H-NMR (DMSO-d6): δ2.75 (1H, dd, J=7.7, 13.4 Hz), 3.02 (1H, dd, J=5.5, 13.4 Hz), 3.60 (1H, dd, J=5.5, 7.7 Hz), 7.13-7.34 (5H, m), 7.63-7.85 (6H, m), 8.55-8.65 (2H, m)

MS (ESI, m/z): 318 (M+H)

Example 55

The following compound was obtained in a similar manner to that of Example 53.

(2S)-2-(methylamino)-3-phenyl-N-[4-(4-pyridinyl)phenyl]propanamide

1H-NMR (DMSO-d6): δ2.24 (3H, s), 2.82 (1H, dd, J=7.4, 13.4 Hz) 2.94 (1H, dd, J=6.4, 13.4 Hz), 3.30-3.41 (1H, m), 7.10-7.33 (6H, m), 7.63-7.84 (7H, m), 8.56-8.64 (2H, m), 9.90-10.15 (1H, br)

MS (ESI, m/z): 332 (M+H)

Example 56

The following compound was obtained in a similar manner to that of Example 53.

(2R,3S)-3-amino-2-hydroxy-3-phenyl-N-[4-(4-pyridinyl)phenyl]propanamide

1H-NMR (DMSO-d6): δ4.11 (1H, s, J=3.8 Hz), 4.23 (1H, s, J=3.8 Hz), 5.64-6.15 (1H, br), 7.15-7.46 (5H, m), 7.65-7.89 (6H, m), 8.55-8.65 (2H, m), 9.40-10.30 (1H, br)

MS (ESI, m/z): 334 (M+H)

Example 57

The following compound was obtained in a similar manner to that of Example 53.

3-amino-2-benzyl-N-[4-(4-pyridinyl)phenyl]propanamide

1H-NMR (DMSO-d6): δ2.63-2.99 (5H, m), 6.91-7.04 (1H, m), 7.10-7.33 (5H, m), 7.61-7.82 (6H, m), 8.54-8.64 (2H, m)

MS (ESI, m/z): 332 (M+H)

Example 58

The following compound was obtained in a similar manner to that of Example 53.

(2S)-1-oxo-3-phenyl-1-[5-(4-pyridinyl)-2,3-dihydro-1H-indol-1-yl]-2-propanamine

1H-NMR (DMSO-d6): δ1.78-1.92 (2H, br), 2.64-2.80 (1H, m), 2.89-3.24 (3H, m), 3.73-3.98 (2H, m), 4.16-4.38 (1H, m), 7.12-7.32 (5H, m), 7.61-7.73 (4H, m), 8.16-8.28 (1H, m), 8.54-8.64 (2H, m)

MS (ESI, m/z): 344 (M+H)

Example 59

The following compound was obtained in a similar manner to that of Example 53.

(3S)-3-amino-3-phenyl-N-[4-(4-pyridinyl)phenyl]propanamide

1H-NMR (DMSO-d6): δ2.62 (2H, d, J=7.0 Hz), 4.32 (1H, t, J=7.0 Hz), 7.16-7.48 (6H, m), 7.63-7.84 (7H, m), 8.55-8.65 (2H, m), 10.21-10.35 (1H, br)

MS (ESI, m/z): 318 (M+H)

Example 60

The following compound was obtained in a similar manner to that of Example 53.

(3R)-3-amino-3-phenyl-N-[4-(4-pyridinyl)phenyl]propanamide

1H-NMR (DMSO-d6): δ2.62 (2H, d, J=7.0 Hz), 4.33 (1H, t, J=7.0 Hz), 7.16-7.48 (6H, m), 7.63-7.84 (7H, m), 8.54-8.65 (2H, m), 10.20-10.36 (1H, br)

MS (ESI, m/z): 318 (M+H)

Example 61

The following compound was obtained in a similar manner to that of Example 4.

1-(2-hydroxybenzyl)-3-[4-(4-pyridinyl)phenyl]urea

1H-NMR (DMSO-d6): δ4.22 (2H, s), 6.60-6.90 (3H, m), 7.00-7.20 (2H, m), 7.50-7.75 (6H, m), 8.50-8.60 (3H, m), 9.13 (1H, br-s)

MS (ESI, m/z): 320 (M+H)

Example 62

To a solution of 4-(4-pyridinyl)aniline (400 mg), O-(7-azabenzotriazol-1-yl)-1,1,3,3-tetramethyluronium hexafluorophosphate (1.34 g), 1-hydroxy-7-azabenzotriazole (480 mg) and (2-nitrophenoxy)acetic acid (695 mg) in N,N-dimethylformamide (10 ml) was added N,N-diisopropylethylamine (1.3 ml), which was stirred overnight at ambient temperature. The reaction mixture was poured into water (30 ml) and stirred for 30 minutes. Insoluble material was collected, washed with water, dried and purified by column chromatography on silica gel (gradient, $CHCl_3$, 10% MeOH in $CHCl_3$). The aliquots of obtained product (100 mg) and 10% palladium on carbon (50% wet, 30 mg) in N,N-dimethylformamide (10 ml) was stirred at ambient temperature for 3 hours under an atmospheric pressure of hydrogen. The catalyst was removed and evaporated under reduced pressure. The resultant was purified by column chromatography on silica gel (gradient, $CHCl_3$, 10% MeOH in $CHCl_3$), which was recrystallized from EtOH to give 2-(2-aminophenoxy)-N-[4-(4-pyridinyl)phenyl]acetamide (30 mg) as an off-white powder.

1H-NMR (DMSO-d6): δ4.67 (2H, s), 5.07 (2H, s), 6.45-6.57 (1H, m), 6.63-6.90 (3H, m), 7.11 (2H, dd, J=1.6, 4.6 Hz), 7.83 (4H, s), 8.61 (2H, dd, J=1.6, 4.6 Hz), 10.17 (1H, s)

MS (ESI, m/z): 342 (M+Na)

Example 63

The following compound was obtained in a similar manner to that of Example 62.

3-(2-aminophenyl)-N-[4-(4-pyridinyl)phenyl]propanamide

1H-NMR (DMSO-d6): δ2.53-2.67 (2H, m), 2.70-2.84 (2H, m), 4.92 (2H, s), 6.48 (1H, dd, J=1.3, 7.2 Hz), 6.61 (1H, dd, J=1.0, 7.9 Hz), 6.84-6.99 (2H, m), 7.68 (2H, dd, J=1.6, 4.6 Hz), 7.70-7.84 (4H, m), 8.59 (2H, dd, J=1.6, 4.6 Hz), 10.12 (1H, s)

MS (ESI, m/z): 318 (M+H)

Example 64

The following compound was obtained in a similar manner to that of Preparation 7.

3-(3-hydroxyphenyl)-N-[4-(4-pyridinyl)phenyl]propanamide

1H-NMR (DMSO-d6): δ2.54-2.70 (2H, m), 2.75-2.91 (2H, m), 6.54-6.71 (3H, m), 7.07 (1H, t, 7.9 Hz), 7.68 (2H, dd, J=1.6, 4.6 Hz), 7.70-7.84 (4H, m), 8.59 (2H, dd, J=1.6, 4.6 Hz), 9.29 (1H, s), 10.11 (1H, s)

MS (ESI, m/z): 319 (M+H)

Example 65

The following compound was obtained in a similar manner to that of following Example 1.

1-[4-(4-pyridinyl)phenyl]-3-(2-thienylmethyl)urea

1H-NMR (DMSO-d6): δ 4.48 (2H, d, J=5.8 Hz), 6.77 (1H, t, J=6.0 Hz), 6.97 (1H, dd, J=3.6, 5.1 Hz), 7.00-7.02 (1H, m), 7.40 (1H, dd, J=1.5, 5.1 Hz), 7.56 (2H, d, J=8.8 Hz), 7.66 (2H, dd, J=1.8, 4.6 Hz), 7.73 (2H, d, J=8.8 Hz), 8.57 (2H, dd, J=1.6, 4.5 Hz), 8.82 (1H, s)

MS (ESI, m/z): 310 (M+H)

Example 66

The following compound was obtained in a similar manner to that of following Example 1.

1-[4-(4-pyridinyl)phenyl]-3-(3-thienylmethyl)urea

1H-NMR (DMSO-d6): δ 4.30 (2H, d, J=5.6 Hz), 6.64 (1H, t, J=5.9 Hz), 7.09 (1H, dd, J=1.1, 5.0 Hz), 7.31-7.34 (1H, m), 7.50 (1H, dd, J=3.0, 5.1 Hz), 7.56 (2H, d, J=8.8 Hz), 7.66 (2H, dd, J=1.6, 4.5 Hz), 7.73 (2H, d, J=8.8 Hz), 8.57 (2H, dd, J=1.7, 4.5 Hz), 8.76 (1H, s)

MS (ESI, m/z): 310 (M+H)

Example 67

The following compound was obtained in a similar manner to that of following Example 1.

1-[(1R)-2-hydroxy-1-(2-thienyl)ethyl]-3-[4-(4-pyridinyl)phenyl]urea

1H-NMR (DMSO-d6): δ 3.64-3.76 (2H, m), 5.01-5.09 (1H, m), 5.19 (1H, t, J=5.3 Hz), 6.76 (1H, d, J=8.3 Hz), 6.99

(1H, dd, J=3.5, 5.0 Hz), 7.02 (1H, d, J=3.5 Hz), 7.38 (1H, dd, J=1.2, 5.0 Hz), 7.54 (2H, d, J=8.8 Hz), 7.66 (2H, dd, J=1.6, 4.6 Hz), 7.73 (2H, d, J=8.8 Hz), 8.57 (2H, dd, J=1.6, 4.6 Hz), 8.89 (1H, s)

MS (ESI, m/z): 340 (M+H)

Example 68

The following compound was obtained in a similar manner to that of following Example 1.

1-[(1S)-2-hydroxy-1-(2-thienyl)ethyl]-3-[4-(4-pyridinyl)phenyl]urea

1H-NMR (DMSO-d6): δ 3.64-3.76 (2H, m), 5.01-5.09 (1H, m), 5.19 (1H, t, J=5.3 Hz), 6.76 (1H, d, J=8.3 Hz), 6.99 (1H, dd, J=3.5, 5.0 Hz), 7.02 (1H, d, J=3.5 Hz), 7.38 (1H, dd, J=1.2, 5.0 Hz), 7.54 (2H, d, J=8.8 Hz), 7.66 (2H, dd, J=1.6, 4.6 Hz), 7.73 (2H, d, J=8.8 Hz), 8.57 (2H, dd, J=1.6, 4.6 Hz), 8.89 (1H, s)

MS (ESI, m/z): 340 (M+H)

Example 69

The following compound was obtained in a similar manner to that of following Example 1.

1-[(1S)-2-hydroxy-1-(3-thienyl)ethyl]-3-[4-(4-pyridinyl)phenyl]urea

1H-NMR (DMSO-d6): 3.61-3.72 (2H, m), 4.84-4.91 (1H, m), 5.00 (1H, t, J=5.2 Hz), 6.67 (1H, d, J=8.4 Hz), 7.12 (1H, dd, J=1.4, 5.1 Hz), 7.31-7.33 (1H, m), 7.48 (1H, dd, J=3.0, 5.0 Hz), 7.53 (2H, d, J=8.7 Hz), 7.66 (2H, dd, J=1.6, 4.5 Hz), 7.72 (2H, d, J=8.7 Hz), 8.57 (2H, dd, J=1.6, 4.5 Hz), 8.82 (1H, s)

MS (ESI, m/z): 340 (M+H)

Example 70

To a solution of 1-[(1R)-2-hydroxy-1-(2-thienyl)ethyl]-3-[4-(4-pyridinyl)phenyl]urea (700 mg) and acetic acid (734 mg) in dichloromethane (10 mL) were added N-chlorosuccinimide (303 mg) and the mixture was refluxed for 3 hours. The mixture was evaporated in vacuo and the residue was purified by column chromatography on silica gel eluting with chloroform/methanol (9:1) and crystallized from ethanol to afford 1-[(1R)-1-(5-chloro-2-thienyl)-2-hydroxyethyl]-3-[4-(4-pyridinyl)phenyl]urea (280 mg) as a crystal.

1H-NMR (DMSO-d6): δ 3.63-3.74 (2H, m), 4.93-5.00 (1H, m), 5.31 (1H, t, J=5.1 Hz), 6.83 (1H, d, J=8.1 Hz), 6.88 (1H, dd, J=0.9, 3.8 Hz), 6.97 (1H, d, J=3.8 Hz), 7.53 (2H, d, J=8.8 Hz), 7.66 (2H, dd, J=1.7, 4.5 Hz), 7.73 (2H, d, J=8.8 Hz), 8.57 (2H, dd, J=1.6, 4.5 Hz), 8.92 (1H, s)

MS (ESI, m/z): 374 (M+H)

Example 71

The following compound was obtained in a similar manner to that of following Example 1.

1-[(1S)-1-(2-chlorophenyl)-2-hydroxyethyl]-3-[4-(4-pyridinyl)phenyl]urea

1H-NMR (DMSO-d6): δ3.51-3.59 (1H, m), 3.68-3.76 (1H, m), 5.12-5.19 (2H, m), 6.98 (1H, d, J=7.6 Hz), 7.28 (1H, td, J=2.0, 7.8 Hz), 7.35 (1H, td, J=1.4, 3.8 Hz), 7.43 (2H, ddd, J=1.6, 3.6, 7.8 Hz), 7.51 (2H, d, J=8.8 Hz), 7.65 (2H, dd, J=1.6, 4.5 Hz), 7.71 (2H, d, J=8.8 Hz), 8.56 (2H, dd, J=1.6, 4.5 Hz), 8.97 (1H, s)

MS (ESI, m/z): 368 (M+H)

Example 72

The following compound was obtained in a similar manner to that of following Example 1.

1-{(1S)-2-hydroxy-1-[2-(trifluoromethyl)phenyl]ethyl}-3-[4-(4-pyridinyl)phenyl]urea 1H-NMR (DMSO-d6): δ 3.43-3.53 (1H, m), 3.67-3.74 (1H, m), 5.10-5.17 (1H, m), 5.22 (1H, t, J=5.3 Hz), 7.05 (1H, d, J=6.9 Hz), 7.44-7.51 (3H, m), 7.62-7.72 (7H, m), 8.56 (2H, d, J=1.6, 4.5 Hz), 8.93 (1H, s)

MS (ESI, m/z): 402 (M+H)

Example 73

The following compound was obtained in a similar manner to that of following Example 1.

1-[(1R)-1-benzyl-2-hydroxyethyl]-3-[4-(4-pyridinyl)phenyl]urea

1H-NMR (DMSO-d6): δ 2.72 (1H, dd, J=7.4, 13.6 Hz), 2.85 (1H, q, J=6.8 Hz), 3.32-3.44 (2H, m), 3.80-3.90 (1H, m), 4.92 (1H, t, J=5.1 Hz), 6.19 (1H, d, J=8.3 Hz), 7.17-7.22 (1H, m), 7.23-7.33 (4H, m), 7.50 (2H, d, J=8.8 Hz), 7.65 (2H, dd, J=1.7, 4.7 Hz), 7.71 (2H, d, J=8.8 Hz), 8.56 (2H, dd, J=1.7, 4.7 Hz), 8.74 (1H, s)

MS (ESI, m/z): 348 (M+H)

Example 74

The following compound was obtained in a similar manner to that of following Example 1.

1-[(1R)-1-(2-fluorobenzyl)-2-hydroxyethyl]-3-[4-(4-pyridinyl)phenyl]urea

1H-NMR (DMSO-d6): δ2.75 (1H, dd, J=8.2, 13.8 Hz), 2.91 (1H, dd, J=6.0, 13.8 Hz), 3.37-3.48 (2H, m), 3.90-4.00 (1H, m), 4.95 (1H, t, J=5.1 Hz), 6.18 (1H, d, J=8.6 Hz), 7.10-7.17 (2H, m), 7.21-7.29 (1H, m), 7.33 (1H, td, J=1.7, 7.6 Hz), 7.48 (2H, d, J=8.7 Hz), 7.64 (2H, dd, J=1.6, 4.6 Hz), 7.69 (2H, d, J=8.7 Hz), 8.56 (2H, dd, J=1.6, 4.6 Hz), 8.72 (1H, s)

MS (ESI, m/z): 366 (M+H)

Example 75

The following compound was obtained in a similar manner to that of following Example 1.

1-[(1R)-1-(3-fluorobenzyl)-2-hydroxyethyl]-3-[4-(4-pyridinyl)phenyl]urea

1H-NMR (DMSO-d6): 2.74 (1H, dd, J=7.7, 13.7 Hz), 2.88 (1H, dd, J=6.4, 13.7 Hz), 3.34-3.45 (2H, m), 3.81-3.95 (1H, m), 4.95 (1H, t, J=5.0 Hz), 6.22 (1H, d, J=8.4 Hz), 6.98-7.12 (3H, m), 7.34 (1H, q, J=11.1 Hz), 7.50 (2H, d, J=8.7 Hz), 7.65 (2H, dd, J=1.6, 4.8 Hz), 7.71 (2H, d, J=8.8 Hz), 8.56 (2H, dd, J=1.5, 4.8 Hz), 8.74 (1H, s)

MS (ESI, m/z): 366 (M+H)

Example 76

The following compound was obtained in a similar manner to that of following Preparation 7.

1-[(1R)-1-(4-fluorobenzyl)-2-hydroxyethyl]-3-[4-(4-pyridinyl)phenyl]urea

1H-NMR (DMSO-d6): δ2.71 (1H, dd, J=7.5, 13.7 Hz), 2.85 (1H, dd, J=6.5, 13.7 Hz), 3.34-3.45 (2H, m), 3.78-3.88 (1H, m), 4.93 (1H, t, J=5.0 Hz), 6.19 (1H, d, J=8.3 Hz), 7.12 (2H, t, J=8.8 Hz), 7.25-7.31 (2H, m), 7.50 (2H, d, J=8.7 Hz), 7.65 (2H, dd, J=1.7, 4.6 Hz), 7.71 (2H, d, J=8.8 Hz), 8.56 (2H, dd, J=1.7, 4.6 Hz), 8.73 (1H, s)

MS (ESI, m/z): 366 (M+H)

Example 77

The following compound was obtained in a similar manner to that of following Example 1.

1-[(1R)-1-(4-chlorobenzyl)-2-hydroxyethyl]-3-[4-(4-pyridinyl)phenyl]urea

1H-NMR (DMSO-d6): δ 2.71 (1H, dd, J=7.6, 13.6 Hz), 2.85 (1H, dd, J=6.3, 13.6 Hz), 3.34-3.44 (2H, m), 3.79-3.90 (1H, m), 4.94 (1H, t, J=5.3 Hz), 6.19 (1H, d, J=8.4 Hz), 7.27 (2H, d, J=8.3 Hz), 7.35 (2H, d, J=8.3 Hz), 7.49 (2H, d, J=8.8 Hz), 7.65 (2H, dd, J=1.8, 4.6 Hz), 7.70 (2H, d, J=8.6 Hz), 8.56 (2H, dd, J=1.8, 4.7 Hz), 8.71 (1H, s)

MS (ESI, m/z): 382 (M+H)

Example 78

The following compound was obtained in a similar manner to that of Example 1.

1-[(1R)-2-hydroxy-1-(2-thienylmethyl)ethyl]-3-[4-(4-pyridinyl)phenyl]urea

1H-NMR (DMSO-d6): δ 2.93 (1H, dd, J=7.4, 14.8 Hz), 3.11 (1H, dd, J=6.2, 14.8 Hz), 3.35-3.49 (2H, m), 3.81-3.91 (1H, m), 4.96 (1H, t, J=5.2 Hz), 6.23 (1H, d, J=8.3 Hz), 6.91 (1H, br), 6.96 (1H, dd, J=3.4, 4.9 Hz), 7.34 (1H, dd, J=1.1, 5.0 Hz), 7.53 (2H, d, J=8.8 Hz), 7.66 (2H, dd, J=1.4, 4.4 Hz), 7.71 (2H, d, J=8.8 Hz), 8.57 (2H, dd, J=1.6, 4.5 Hz), 8.79 (1H, s)

MS (ESI, m/z): 354 (M+H)

Example 79

The following compound was obtained in a similar manner to that of Example 1.

1-[(1R)-2-hydroxy-1-(3-thienylmethyl)ethyl]-3-[4-(4-pyridinyl)phenyl]urea

1H-NMR (DMSO-d6) δ 2.75 (1H, dd, J=7.3, 14.3 Hz), 2.88 (1H, dd, J=6.5, 14.3 Hz), 3.34-3.46 (2H, m), 3.82-3.93 (1H, m), 4.90 (1H, t, J=5.2 Hz), 6.18 (1H, d, J=8.3 Hz), 7.03 (1H, dd, J=1.2, 4.9 Hz), 7.19-7.23 (1H, m), 7.46 (1H, dd, J=2.9, 4.9 Hz), 7.52 (2H, d, J=8.8 Hz), 7.65 (2H, dd, J=1.6, 4.6 Hz), 7.71 (2H, d, J=8.8 Hz), 8.57 (2H, dd, J=1.6, 4.6 Hz), 8.76 (1H, s)

MS (ESI, m/z): 354 (M+H)

Example 80

The following compound was obtained in a similar manner to that of Example 1.

1-[(1S,2S)-2-hydroxy-1-(hydroxymethyl)-2-phenylethyl]-3-[4-(4-pyridinyl)phenyl]urea 1H-NMR (DMSO-d6) δ 3.37-3.45 (1H, m), 3.48-3.56 (1H, m), 3.73-3.83 (1H, m), 4.90 (1H, dd, J=4.5, 6.1 Hz), 4.98 (1H, br), 5.70 (1H, d, J=3.9 Hz), 6.22 (1H, d, J=8.7 Hz), 7.21 (1H, t, J=7.2 Hz), 7.31 (2H, t, J=7.4 Hz), 7.39 (2H, d, J=7.4 Hz), 7.44 (2H, d, J=8.8 Hz), 7.63 (2H, dd, J=1.5, 4.4 Hz), 7.68 (2H, d, J=8.7 Hz), 8.56 (2H, dd, J=1.5, 4.4 Hz), 8.91 (1H, s)

MS (ESI, m/z): 364 (M+H)

Example 81

The following compound was obtained in a similar manner to that of Example 1.

1-[(2S)-2-hydroxy-2-phenylethyl]-3-[4-(4-pyridinyl)phenyl]urea

1H-NMR (DMSO-d6): δ 3.10-3.20 (1H, m), 3.36-3.46 (1H, m) 4.61-4.69 (1H, m), 5.60 (1H, d, J=4.3 Hz), 6.31 (1H, dd, J=4.9, 6.1 Hz), 7.24-7.29 (1H, m), 7.32-7.42 (4H, m), 7.53 (2H, d, J=8.8 Hz), 7.65 (2H, dd, J=1.6, 4.5 Hz), 7.71 (2H, d, J=8.8 Hz), 8.57 (2H, dd, J=1.6, 4.5 Hz), 8.89 (1H, s)

MS (ESI, m/z): 334 (M+H)

Example 82

The following compound was obtained in a similar manner to that of Example 1.

1-[(1R)-3-hydroxy-1-phenylpropyl]-3-[4-(4-pyridinyl)phenyl]urea

1H-NMR (DMSO-d6): δ 1.79-1.93 (2H, m), 3.36-3.48 (2H, m), 4.61 (1H, t, J=4.9 Hz), 4.86 (1H, q, J=7.4 Hz), 6.80 (1H, d, J=8.1 Hz), 7.20-7.26 (1H, m), 7.30-7.37 (4H, m), 7.51 (2H, d, J=8.8 Hz), 7.64 (2H, dd, J=1.6, 4.5 Hz), 7.70 (2H, d, J=8.8 Hz), 8.56 (2H, dd, J=1.6, 4.5 Hz), 8.71 (1H, s)

MS (ESI, m/z): 370 (M+Na)

Example 83

The following compound was obtained in a similar manner to that of Example 1.

1-[(1S)-3-hydroxy-1-phenylpropyl]-3-[4-(4-pyridinyl)phenyl]urea

1H-NMR (DMSO-d6): δ 1.79-1.93 (2H, m), 3.36-3.48 (2H, m), 4.61 (1H, t, J=4.9 Hz), 4.86 (1H, q, J=7.4 Hz), 6.80 (1H, d, J=8.1 Hz), 7.20-7.26 (1H, m), 7.30-7.37 (4H, m), 7.51 (2H, d, J=8.8 Hz), 7.64 (2H, dd, J=1.6, 4.5 Hz), 7.70 (2H, d, J=8.8 Hz), 8.56 (2H, dd, J=1.5, 4.5 Hz), 8.71 (1H, s)

MS (ESI, m/z): 348 (M+H)

Example 84

The following compound was obtained in a similar manner to that of Example 1.

1-(2,4'-bipyridin-5-yl)-3-[(1S)-2-hydroxy-1-phenylethyl]urea

1H-NMR (DMSO-d6): δ 3.51-3.76 (2H, m), 4.71-4.86 (1H, m), 5.04 (1H, t, J=5.1 Hz), 6.97 (1H, d, J=7.8 Hz), 7.19-7.31 (1H, m), 7.34 (4H, d, J=4.4 Hz), 7.94-8.10 (4H, m), 8.63 (3H, d, J=6.0 Hz), 9.11 (1H, s)

MS (ESI, m/z): 335 (M+H)

Example 85

The following compound was obtained in a similar manner to that of Example 53.

2-fluoro-N-[4-(4-pyridinyl)phenyl]-D-phenylalaninamide

1H-NMR (DMSO-d6): δ2.75-2.85 (1H, m), 2.95-3.05 (1H, m), 3.6-3.65 (1H, m), 7.1-7.4 (4H, m), 7.65-7.8 (6H, m), 8.55-8.6 (2H, m)

MS (ESI, m/z): 336 (M+H)

Example 86

The following compound was obtained in a similar manner to that of Example 53.

3-fluoro-N-[4-(4-pyridinyl)phenyl]-D-phenylalaninamide

1H-NMR (DMSO-d6): δ2.75-2.85 (1H, m), 2.95-3.05 (1H, m), 3.55-3.65 (1H, m), 6.95-7.1 (3H, m), 7.25-7.35 (1H, m), 7.65-7.8 (6H, m), 8.55-8.6 (2H, m)

MS (ESI, m/z): 336 (M+H)

Example 87

The following compound was obtained in a similar manner to that of Example 53.

4-fluoro-N-[4-(4-pyridinyl)phenyl]-D-phenylalaninamide

1H-NMR (DMSO-d6): δ 1.50-2.26 (1H, br), 2.75 (1H, dd, J=7.8, 13.4 Hz), 2.99 (1H, dd, J=5.5, 13.4 Hz), 3.57 (1H, dd, J=5.5, 7.8 Hz), 7.06-7.14 (2H, m), 7.24-7.32 (2H, m), 7.69 (2H, dd, J=1.6, 4.4 Hz), 7.73-7.82 (4H, m), 8.60 (2H, dd, J=1.6, 4.4 Hz), 9.20-10.80 (1H, br)

MS (ESI, m/z): 336 (M+H)

Example 88

The following compound was obtained in a similar manner to that of Example 53.

4-fluoro-N-[4-(4-pyridinyl)phenyl]-L-phenylalaninamide

1H-NMR (DMSO-d6): δ 1.60-2.28 (1H, br), 2.75 (1H, dd, J=7.8, 13.4 Hz), 2.99 (1H, dd, J=5.5, 13.4 Hz), 3.57 (1H, dd, J=5.5, 7.8 Hz), 7.06-7.14 (2H, m), 7.25-7.32 (2H, m), 7.69 (2H, dd, J=1.5, 4.4 Hz), 7.74-7.82 (4H, m), 8.60 (2H, dd, J=1.5, 4.4 Hz), 9.20-10.80 (1H, br)

MS (ESI, m/z): 336 (M+H)

Example 89

The following compound was obtained in a similar manner to that of Example 53.

2-chloro-N-[4-(4-pyridinyl)phenyl]-L-phenylalaninamide

1H-NMR (DMSO-d6): δ 1.62-2.30 (1H, br), 2.89 (1H, dd, J=7.9, 13.6 Hz), 3.15 (1H, dd, J=6.1, 13.6 Hz), 3.66 (1H, dd, J=6.1, 7.9 Hz), 7.21-7.29 (2H, m), 7.35-7.45 (2H, m), 7.69 (2H, dd, J=1.6, 4.5 Hz), 7.74-7.83 (4H, m), 8.60 (2H, dd, J=1.6, 4.6 Hz), 9.20-10.80 (1H, br)

MS (ESI, m/z): 352 (M+H)

Example 90

The following compound was obtained in a similar manner to that of Example 53.

4-chloro-N-[4-(4-pyridinyl)phenyl]-D-phenylalaninamide

1H-NMR (DMSO-d6): δ2.7-2.8 (1H, m), 2.95-3.05 (1H, m), 3.55-3.6, 1H, m), 7.28 (2H, d, J=8.4 Hz), 7.33 (2H, d, J=8.4 Hz), 7.65-7.7 (2H, m), 7.76 (2H, d, J=9.0 Hz), 7.80 (2H, d, J=9.0 Hz)

MS (ESI, m/z): 352 (M+H)

Example 91

The following compound was obtained in a similar manner to that of Preparation 36 and successively Example 53.

3,4-dichloro-N-[4-(4-pyridinyl)phenyl]-D-phenylalaninamide 1H-NMR (DMSO-d6): δ2.7-2.8 (1H, m), 2.95-3.05 (1H, m), 3.55-3.6, 1H, m), 7.2-7.25 (1H, m), 7.55-7.6 (1H, m), 7.65-7.7 (2H, m), 7.76 (2H, d, J=8.8 Hz), 7.80 (2H, d, J=8.8 Hz), 8.55-8.65 (2H, m)

MS (ESI, m/z): 386 (M+H)

Example 92

The following compound was obtained in a similar manner to that of Example 53.

4-trifluoromethyl-N-[4-(4-pyridinyl)phenyl]-D-phenylalaninamide

1H-NMR (DMSO-d6): δ1.72-2.28 (1H, br), 2.84 (1H, dd, J=8.2, 13.3 Hz), 3.11 (1H, dd, J=5.4, 13.3 Hz), 3.63 (1H, dd, J=5.4, 8.2 Hz), 7.49 (2H, d, J=8.0 Hz), 7.65 (2H, d, J=8.0 Hz), 7.69 (2H, dd, J=1.5, 4.4 Hz), 7.74-7.83 (4H, m), 8.60 (2H, dd, J=1.5, 4.4 Hz), 9.30-10.80 (1H, br)

MS (ESI, m/z): 386 (M+H)

Example 93

The following compound was obtained in a similar manner to that of Example 53.

4-methoxy-N-[4-(4-pyridinyl)phenyl]-D-phenylalaninamide

1H-NMR (DMSO-d6): δ 2.65-2.75 (1H, m), 2.9-3.0 (1H, m), 3.5-3.6 (1H, m), 3.71 (3H, s), 6.84 (2H, d, J=8.6 Hz), 7.17 (2H, d, J=8.6 Hz), 7.65-7.7 (2H, m), 7.75-7.85 (4H, m), 8.55-8.65 (2H, m)

MS (ESI, m/z): 348 (M+H)

Example 94

The following compound was obtained in a similar manner to that of Example 53.

N-[4-(4-pyridinyl)phenyl]-3-(2-thienyl)-D-alaninamide

1H-NMR (DMSO-d6): δ3.0-3.08 (1H, m), 3.17-3.25 (1H, m), 3.56-3.63 (1H, m), 6.86-6.96 (2H, m), 7.33 (1H, d, J=4.8 Hz), 7.69 (2H, d, J=4.4 Hz), 7.76-7.82 (4H, m), 8.60 (2H, d, J=6.1 Hz)

MS (ESI, m/z): 324 (M+H)

Example 95

The following compound was obtained in a similar manner to that of Example 53.

N-[4-(4-pyridinyl)phenyl]-3-(2-thienyl)-L-alaninamide

1H-NMR (DMSO-d6): δ3.0-3.08 (1H, m), 3.17-3.25 (1H, m), 3.56-3.63 (1H, m), 6.86-6.96 (2H, m), 7.33 (1H, d, J=4.8 Hz), 7.69 (2H, d, J=4.4 Hz), 7.76-7.82 (4H, m), 8.60 (2H, d, J=6.1 Hz)

MS (ESI, m/z): 324 (M+H)

Example 96

The following compound was obtained in a similar manner to that of Example 53.

N-[4-(4-pyridinyl)phenyl]-3-(thiazol-4-yl)-L-alaninamide

1H-NMR (DMSO-d6): δ 2.92-2.99 (1H, m), 3.17-3.24 (1H, m), 3.73-3.78 (1H, m), 7.42 (1H, d, J=2.0 Hz), 7.66-7.7 (2H, m), 7.75-7.5 (4H, m), 8.58-8.63 (2H, m)

MS (ESI, m/z): 323 (M+H)

Example 97

The following compound was obtained in a similar manner to that of Example 53.

N-[4-(4-pyridinyl)phenyl]-3-(thiazol-4-yl)-D-alaninamide

1H-NMR (DMSO-d6): δ 2.92-2.99 (1H, m), 3.17-3.24 (1H, m), 3.73-3.78 (1H, m), 7.42 (1H, d, J=2.0 Hz), 7.66-7.7 (2H, m), 7.75-7.5 (4H, m), 8.58-8.63 (2H, m)

MS (ESI, m/z): 323 (M+H)

Example 98

The following compound was obtained in a similar manner to that of Example 53.

N-alpha-methyl-N-[4-(4-pyridinyl)phenyl]-D-phenylalaninamide

1H-NMR (DMSO-d6): δ 1.94-2.13 (1H, br), 2.24 (3H, s), 2.83 (1H, dd, J=7.3, 13.4 Hz), 2.94 (1H, dd, J=6.5, 13.4 Hz), 3.29-3.41 (1H, m), 7.15-7.29 (5H, m), 7.68 (2H, dd, J=1.6, 4.4 Hz), 7.72-7.80 (4H, m), 8.60 (2H, dd, J=1.6, 4.4 Hz), 9.94-10.10 (1H, br)

MS (ESI, m/z): 332 (M+H)

Example 99

The following compound was obtained in a similar manner to that of Preparation 36.

N-alpha,N-alpha-dimethyl-N-[4-(4-pyridinyl)phenyl]-L-phenylalaninamide

1H-NMR (DMSO-d6): δ 2.33 (6H, s), 2.83-2.89 (1H, m), 3.03-3.11 (1H, m), 3.43-3.48 (1H, m), 7.13-7.18 (1H, m), 7.22-7.28 (4H, m), 7.65-7.68 (2H, m), 7.71 (2H, d, J=9.1 Hz), 7.76 (2H, d, J=9.1 Hz), 8.55-8.6 (2H, m), 9.98 (1H, brs)

MS (ESI, m/z): 346 (M+H)

Example 100

To a solution of N-[4-(4-pyridinyl)phenyl]-D-phenylalaninamide (280 mg) in methanol (10 mL) were added formaldehyde solution (37 wt %) (0.36 mL) and 10% palladium on charcoal (200 mg) and the mixture was hydrogenated at ambient temperature for 5 hours. The catalysts were removed by filtration on celite pad, and the filtrate was evaporated in vacuo. The residue was triturated with diisopropyl ether to afford N-alpha,N-alpha-dimethyl-N-[4-(4-pyridinyl)phenyl]-D-phenylalaninamide (95 mg) as a white powder.

1H-NMR (DMSO-d6): δ 2.39 (6H, s), 2.86-2.97 (1H, m), 3.02-3.12 (1H, m), 3.47-3.57 (1H, m), 7.13-7.29 (5H, m), 7.64-7.73 (4H, m), 7.73-7.79 (2H, m), 8.56-8.64 (2H, m), 9.96-10.08 (1H, br)

MS (ESI, m/z): 346 (M+H)

Example 101

The following compound was obtained in a similar manner to that of Example 53.

(3R)—N-[4-(4-pyridinyl)phenyl]-1,2,3,4-tetrahydro isoquinoline-3-carboxamide

1H-NMR (DMSO-d6): δ 2.88 (1H, dd, J=10.0, 16.2 Hz), 3.00 (1H, dd, J=4.7, 16.2 Hz), 3.66 (1H, dd, J=4.7, 10.0 Hz), 3.97 (2H, dd, J=16.6, 20.3 Hz), 7.05-7.10 (1H, m), 7.11-7.18 (3H, m), 7.70 (2H, dd, J=1.6, 4.6 Hz), 7.81 (2H, d, J=8.8 Hz), 7.85 (2H, d, J=8.9 Hz), 8.60 (2H, dd, J=1.6, 4.6

MS (ESI, m/z): 330 (M+H)

Example 102

The following compound was obtained in a similar manner to that of Example 53.

(3S)—N-[4-(4-pyridinyl)phenyl]-1,2,3,4-tetrahydro isoquinoline-3-carboxamide

1H-NMR (DMSO-d6): δ 2.88 (1H, dd, J=10.0, 16.2 Hz), 3.00 (1H, dd, J=4.7, 16.2 Hz), 3.66 (1H, dd, J=4.7, 10.0 Hz), 3.97 (2H, dd, J=16.6, 20.3 Hz), 7.05-7.10 (1H, m), 7.11-7.18 (3H, m), 7.70 (2H, dd, J=1.6, 4.6 Hz), 7.81 (2H, d, J=8.8 Hz), 7.85 (2H, d, J=8.9 Hz), 8.60 (2H, dd, J=1.6, 4.6 Hz), 10.12 (1H, s)

MS (ESI, m/z): 330 (M+H)

Example 103

To a solution of N-[4-(4-pyridinyl)phenyl]-D-phenylalaninamide (400 mg) in dichloromethane (24 mL) was added dropwise trichloroacetyl isocyanate (261 mg) at 5° C. and the mixture was stirred at the same temperature for 1 hour. The mixture was evaporated in vacuo and the residue was triturated with hexane to afford crude N-[4-(4-pyridinyl)phenyl]-N-alpha-[(trichloroacetyl)carbamoyl]-D-phenylalaninamide. The crude product was dissolved in methanol (20 mL) and silica gel (10 g) was added. The mixture was stirred at ambient temperature for 20 hours and evaporated in vacuo. The residue was purified by column chromatography on silica gel and recrystallized from ethanol to afford N-alpha-carbamoyl-N-[4-(4-pyridinyl)phenyl]-D-phenylalaninamide (287 mg) as a white crystal.

1H-NMR (DMSO-d6): δ2.8-2.87 (1H, m), 2.92-3.04 (1H, m), 4.52-4.60 (1H, m), 5.63 (2H, brs), 6.35 (1H, d, J=8.4 Hz), 7.17-7.3 (4H, m), 7.67-7.89 (6H, m), 8.56-8.63 (2H, m), 10.28 (1H, brs)

MS (ESI, m/z): 360 (M+H)

Example 104

The following compound was obtained in a similar manner to that of Example 53.

N-[4-(4-pyridinyl)phenyl]-D-tryptophanamide

1H-NMR (DMSO-d6): δ 2.87-2.94 (1H, m), 3.13-3.19 (1H, m), 3.63-3.69 (1H, m), 6.94-6.99 (1H, m), 7.03-7.08 (1H, m), 7.18 (1H, d, J=2.3 Hz), 7.33 (1H, d, J=8.2 Hz), 7.60 (1H, d, J=7.9 Hz), 7.67-7.71 (2H, m), 7.76-7.82 (4H, m), 8.57-8.62 (2H, m), 10.85 (1H, brs)

MS (ESI, m/z): 357 (M+H)

Example 105

The following compound was obtained in a similar manner to that of Example 53.

3-(1-benzothien-3-yl)-N-[4-(4-pyridinyl)phenyl]-D-alaninamide

1H-NMR (DMSO-d6): δ 2.98-3.05 (1H, m), 3.28-3.35 (1H, m), 3.72-3.77 (1H, m), 7.33-7.44 (2H, m), 7.52 (1H, s), 7.67-7.71 (2H, m), 7.76-7.82 (4H, m), 8.58-8.62 (2H, m)

MS (ESI, m/z): 374 (M+H)

Example 106

The following compound was obtained in a similar manner to that of Preparation 36 and successively Example 53.

(2R)-2-amino-4-phenyl-N-[4-(4-pyridinyl)phenyl]butanamide

1H-NMR (DMSO-d6): δ 1.68-1.8 (1H, m), 1.92-2.02 (1H, m), 2.6-2.8 (2H, m), 7.14-7.31 (3H, m), 7.67-7.72 (2H, m), 7.9-8.02 (4H, m), 8.58-8.62 (2H, m)

MS (ESI, m/z): 332 (M+H)

Example 107

The following compound was obtained in a similar manner to that of Preparation 36 and successively Example 53.

(3R)-3-amino-4-phenyl-N-[4-(4-pyridinyl)phenyl]butanamide

1H-NMR (DMSO-d6): δ 2.23-2.31 (1H, m), 2.38-2.43 (1H, m), 2.6-2.75 (2H, m), 7.19-7.34 (2H, m), 7.64-7.68 (2H, m), 7.73 (2H, d, J=8.9 Hz), 7.78 (2H, s, J=8.9 Hz), 8.57-8.62 (2H, m), 10.32 (1H, brs)

MS (ESI, m/z): 332 (M+H)

Example 108

The following compound was obtained in a similar manner to that of Example 53.

(2R)-2-amino-2-phenyl-N-[4-(4-pyridinyl)phenyl]acetamide

1H-NMR (DMSO-d6): δ 4.57 (1H, s), 7.24-7.29 (1H, m), 7.34 (2H, t, J=7.3 Hz), 7.49 (2H, d, J=7.3 Hz), 7.68 (2H, dd, J=1.6, 4.6 Hz), 7.79 (4H, t, J=9.5 Hz), 8.59 (2H, dd, J=1.6, 4.6 Hz)

MS (ESI, m/z): 304 (M+H)

Example 109

The following compound was obtained in a similar manner to that of Example 53.

(2S)-2-amino-2-phenyl-N-[4-(4-pyridinyl)phenyl]acetamide

1H-NMR (DMSO-d6): δ 4.57 (1H, s), 7.24-7.29 (1H, m), 7.34 (2H, t, J=7.3 Hz), 7.49 (2H, d, J=7.3 Hz), 7.68 (2H, dd, J=1.6, 4.6 Hz), 7.79 (4H, t, J=9.5 Hz), 8.59 (2H, dd, J=1.6, 4.6 Hz)

MS (ESI, m/z): 304 (M+H)

Example 110

The following compound was obtained in a similar manner to that of Example 53.

(2S)-2-amino-2-(2-chlorophenyl)-N-[4-(4-pyridinyl)phenyl]acetamide

1H-NMR (DMSO-d6): δ 4.89 (1H, s), 7.28-7.38 (2H, m), 7.44 (1H, dd, J=1.7, 7.6 Hz), 7.56 (1H, dd, J=1.9, 7.5 Hz), 7.69 (2H, dd, J=1.6, 4.6 Hz), 7.82 (4H, td, J=2.5, 9.2 Hz), 8.60 (2H, dd, J=1.6, 4.6 Hz)

MS (ESI, m/z): 338 (M+H)

Example 111

The following compound was obtained in a similar manner to that of Example 53.

2-amino-2-(2-fluorophenyl)-N-[4-(4-pyridinyl)phenyl]acetamide

1H-NMR (DMSO-d6): δ 4.79 (1H, s), 7.14-7.23 (2H, m), 7.29-7.37 (1H, m), 7.53 (1H, td, J=1.7, 7.6 Hz), 7.69 (2H, dd, J=1.6, 4.5 Hz), 7.81 (4H, t, J=9.8 Hz), 8.60 (2H, dd, J=1.6, 4.5 Hz)

MS (ESI, m/z): 322 (M+H)

Example 112

The following compound was obtained in a similar manner to that of Example 53.

(2S)-2-amino-N-[4-(4-pyridinyl)phenyl]-2-[2-(trifluoro methyl)phenyl]acetamide

1H-NMR (DMSO-d6): δ 4.87 (1H, s), 7.50 (1H, t, J=7.5 Hz), 7.66-7.73 (4H, m), 7.76-7.86 (5H, m), 8.60 (2H, dd, J=1.6, 4.6 Hz)

MS (ESI, m/z): 372 (M+H)

Example 113

The following compound was obtained in a similar manner to that of Example 53.

2-amino-2-(2-methoxyphenyl)-N-[4-(4-pyridinyl)phenyl]acetamide

1H-NMR (DMSO-d6): δ 3.79 (3H, s), 4.74 (1H, s), 6.93 (1H, td, J=0.9, 7.4 Hz), 7.00 (1H, d, J=7.5 Hz), 7.26 (1H, td, J=1.7, 7.8 Hz), 7.34 (1H, dd, J=1.7, 7.5 Hz), 7.69 (2H, dd, J=1.6, 4.6 Hz), 7.81 (4H, dd, J=9.0, 14.2 Hz), 8.59 (2H, dd, J=1.6, 4.6 Hz)

MS (ESI, m/z): 334 (M+H)

Example 114

The following compound was obtained in a similar manner to that of Example 53.

(2S)-2-amino-2-(4-fluorophenyl)-N-[4-(4-pyridinyl)phenyl]acetamide

1H-NMR (DMSO-d6): δ 4.58 (1H, s), 7.17 (2H, t, J=8.8 Hz), 7.53 (2H, dd, J=5.6, 8.8 Hz), 7.68 (2H, dd, J=1.6, 4.6 Hz), 7.93 (4H, s), 8.59 (2H, dd, J=1.6, 4.6 Hz)

MS (ESI, m/z): 322 (M+H)

Example 115

The following compound was obtained in a similar manner to that of Example 53.

2-amino-2-(2-furyl)-N-[4-(4-pyridinyl)phenyl]acetamide

1H-NMR (DMSO-d6): δ 8.60 (2H, d, J=6.1 Hz), 7.80 (4H, s), 7.69 (2H, d, J=6.1 Hz), 7.59 (1H, s), 6.41 (1H, dd, J=1.8, 3.2 Hz), 6.34 (1H, d, J=3.2 Hz), 4.61 (1H, s)

MS (ESI, m/z): 316 (M+Na)

Example 116

The following compound was obtained in a similar manner to that of Example 53.

(2S)-2-amino-N-[4-(4-pyridinyl)phenyl]-2-(2-thienyl)acetamide

1H-NMR (DMSO-d6): δ 4.79 (1H, s), 6.97 (1H, dd, J=5.0, 3.4 Hz), 7.07 (1H, d, J=3.4 Hz), 7.41 (1H, dd, J=5.0, 1.0 Hz), 7.67-7.7 (2H, m), 7.78-7.83 (4H, m), 8.58-8.62 (2H, m)

MS (ESI, m/z): 310 (M+H)

Example 117

The following compound was obtained in a similar manner to that of Preparation 37.

(2R)-2-morpholin-4-yl-3-phenyl-N-[4-(4-pyridinyl)phenyl]propanamide

1H-NMR (DMSO-d6): δ 2.58-2.72 (4H, m), 2.89 (1H, dd, J=4.9, 13.0 Hz), 3.10 (1H, dd, J=9.8, 13.0 Hz), 3.50 (1H, q, J=4.9 Hz), 3.58 (4H, br), 7.13-7.19 (1H, m), 7.22-7.27 (4H, m), 7.67 (2H, dd, J=1.7, 4.5 Hz), 7.70 (2H, d, J=8.9 Hz), 7.76 (2H, d, J=8.9 Hz), 8.59 (2H, dd, J=1.7, 4.5 Hz), 10.00 (1H, s)

MS (ESI, m/z): 388 (M+H)

Example 118

The following compound was obtained in a similar manner to that of Preparation 37.

(2S)-2-morpholin-4-yl-3-phenyl-N-[4-(4-pyridinyl)phenyl]propanamide

1H-NMR (DMSO-d6): δ 2.58-2.72 (4H, m), 2.89 (1H, dd, J=4.9, 13.0 Hz), 3.10 (1H, dd, J=9.8, 13.0 Hz), 3.50 (1H, q, J=4.9 Hz), 3.58 (4H, br), 7.13-7.19 (1H; m), 7.22-7.27 (4H, m), 7.67 (2H, dd, J=1.7, 4.5 Hz), 7.70 (2H, d, J=8.9 Hz), 7.76 (2H, d, J=8.9 Hz), 8.59 (2H, dd, J=1.7, 4.5 Hz), 10.00 (1H, s)

MS (ESI, m/z): 388 (M+H)

Example 119

The following compound was obtained in a similar manner to that of Preparation 36.

2-morpholin-4-yl-2-phenyl-N-[4-(4-pyridinyl)phenyl]acetamide

1H-NMR (DMSO-d6): δ 2.35-2.47 (4H, m), 3.58-3.77 (4H, m), 4.03 (1H, s), 7.29-7.34 (1H, m), 7.35-7.40 (2H, m), 7.54 (1H, d, J=7.0 Hz), 7.66-7.69 (2H, m), 7.76-7.8 (4H, m), 8.58-8.62 (2H, m), 10.32 (1H, s)

MS (ESI, m/z): 374 (M+H)

Example 120

The following compound was obtained in a similar manner to that of Preparation 37.

2-(4-hydroxypiperidin-1-yl)-3-phenyl-N-[4-(4-pyridinyl)phenyl]propanamide

1H-NMR (DMSO-d6): δ 1.33-1.42 (2H, m), 1.66-1.78 (2H, m), 2.3-2.42 (2H, m), 2.8-2.96 (3H, m), 3.06-3.16 (1H, m), 3.37-3.44 (1H, m), 3.45-3.55 (1H, m), 4.53 (1H, d, J=4.1 Hz), 7.12-7.18 (1H, m), 7.21-7.26 (4H, m), 7.64-7.66 (2H, m), 7.71 (2H, d, J=8.9 Hz), 7.76 (2H, d, J=8.9 Hz), 8.58-8.62 (2H, m), 9.94 (1H, brs)

MS (ESI, m/z): 402 (M+H)

Example 121

The following compound was obtained in a similar manner to that of Preparation 36.

2-(4-hydroxypiperidin-1-yl)-2-phenyl-N-([4-(4-pyridinyl)phenyl]acetamide

1H-NMR (DMSO-d6): δ 1.4-1.52 (2H, m), 1.66-1.78 (2H, m), 1.98-2.08 (1H, m), 2.15-2.22 (1H, m), 2.55-2.63 (1H, m), 2.7-2.78 (1H, m), 3.42-3.52 (1H, m), 4.02-4.06 (1H, m), 4.58 (1H, dd, J=4.0 Hz), 7.26-7.39 (4H, m), 7.45-7.52 (2H, m), 7.64-7.68 (2H, m), 7.76-7.81 (3H, m), 8.58-8.62 (2H, m), 10.24 (1H, brs)

MS (ESI, m/z): 388 (M+H)

Example 122

The following compound was obtained in a similar manner to that of Preparation 36.

2-(1,1-dioxidothiomorpholin-4-yl)-2-phenyl-N-[4-(4-pyridinyl)phenyl]acetamide

1H-NMR (DMSO-d6): δ 2.84-2.94 (2H, m), 2.96-3.06 (2H, m), 3.11-3.27 (4H, m), 4.55 (1H, s), 7.32-7.57 (5H, m), 7.69 (2H, d, J=6.2 Hz), 7.78-7.84 (4H, m), 8.60 (2H, d, J=6.1 Hz), 10.33 (1H, br s)

MS (ESI, m/z): 422 (M+H)

Example 123

The following compound was obtained in a similar manner to that of Preparation 37.

N-[4-(4-pyridinyl)phenyl]-N-alpha-(tetrahydro-2H-pyran-4-yl)-D-phenylalaninamide 1H-NMR (DMSO-d6): δ 1.1-1.32 (2H, m), 1.6-1.75 (2H, m), 2.1-2.22 (1H, m), 2.5-2.6 (1H, m), 2.79-2.98 (2H, m), 3.15-3.28 (2H, m), 3.56-3.63 (1H, m), 3.7-3.78 (2H, m), 7.15-7.22 (1H, m), 7.24-7.28 (4H, m), 7.66-7.69 (2H, m), 7.72 (2H, d, J=8.8 Hz), 7.78 (2H, D, J=8.8 Hz), 8.58-8.62 (2H, m), 10.03 (1H, brs)

MS (ESI, m/z): 402 (M+H)

Example 124

The following compound was obtained in a similar manner to that of Preparation 36 and successively Example 53.

3-cyclohexyl-N-[4-(4-pyridinyl)phenyl]-D-alaninamide

1H-NMR (DMSO-d6): δ 0.79-1.00 (2H, m), 1.06-1.38 (4H, m) 1.39-1.84 (7H, m), 3.35-3.42 (1H, m), 7.66-7.71 (2H, m), 7.76-7.81 (4H, m), 8.56-8.62 (2H, m)

MS (ESI, m/z): 324 (M+H)

Example 125

The following compound was obtained in a similar manner to that of Preparation 36 and successively Example 53.

(2R)-2-amino-2-cyclohexyl-N-[4-(4-pyridinyl)phenyl]acetamide

1H-NMR (DMSO-d6): δ 0.96-1.28 (5H, m), 1.49-1.64 (3H, m), 1.65-1.78 (3H, m), 3.13 (1H, d, J=5.6 Hz), 7.68 (2H, dd, J=1.6, 4.6 Hz), 7.75-7.83 (4H, m), 8.59 (2H, dd, J=1.6, 4.6 Hz)

MS (ESI, m/z): 310 (M+H)

Example 126

The following compound was obtained in a similar manner to that of Preparation 36 and successively Example 53.

(2S)-2-amino-2-cyclohexyl-N-[4-(4-pyridinyl)phenyl]acetamide

1H-NMR (DMSO-d6): δ 0.95-1.29 (5H, m), 1.49-1.64 (3H, m), 1.65-1.80 (3H, m), 3.13 (1H, d, J=5.6 Hz), 7.68 (2H, dd, J=1.6, 4.6 Hz), 7.74-7.84 (4H, m), 8.59 (2H, dd, J=1.6, 4.6 Hz)

MS (ESI, m/z): 310 (M+H)

Example 127

The following compound was obtained in a similar manner to that of Preparation 36.

(2R)-2-hydroxy-3-phenyl-N-[4-(4-pyridinyl)phenyl]propanamide

1H-NMR (DMSO-d6): δ 2.86 (1H, dd, J=8.2, 13.6 Hz), 3.08 (1H, dd, J=4.2, 13.6 Hz), 4.28 (1H, br), 5.90 (1H, s), 7.14-7.31 (5H, m), 7.69 (2H, d, J=6.1 Hz), 7.78 (2H, d, J=8.9 Hz), 7.86 (2H, d, J=8.8 Hz), 8.60 (2H, d, J=6.2 Hz), 9.91 (1H, s)

MS (ESI, m/z): 319 (M+H)

Example 128

The following compound was obtained in a similar manner to that of Preparation 36.

(2S)-2-hydroxy-3-phenyl-N-[4-(4-pyridinyl)phenyl]propanamide

1H-NMR (DMSO-d6): δ 2.86 (1H, dd, J=8.2, 13.6 Hz), 3.08 (1H, dd, J=4.2, 13.6 Hz), 4.28 (1H, br), 5.90 (1H, s), 7.14-7.31 (5H, m), 7.69 (2H, d, J=6.1 Hz), 7.78 (2H, d, J=8.9 Hz), 7.86 (2H, d, J=8.8 Hz), 8.60 (2H, d, J=6.2 Hz), 9.91 (1H, s)

MS (ESI, m/z): 319 (M+H)

Example 129

The following compound was obtained in a similar manner to that of Preparation 36.

(2R)-2-hydroxy-2-phenyl-N-[4-(4-pyridinyl)phenyl]acetamide

1H-NMR (DMSO-d6): δ 5.14 (1H, s), 6.51 (1H, s), 7.28-7.33 (1H, m), 7.34-7.40 (2H, m), 7.52-7.56 (2H, m), 7.69 (2H, dd, J=1.6, 4.5 Hz), 7.79 (2H, d, J=8.8 Hz), 7.89 (2H, d, J=8.8 Hz), 8.60 (2H, dd, J=1.6, 4.5 Hz), 10.15 (1H, s)

MS (ESI, m/z): 327 (M+Na)

Example 130

The following compound was obtained in a similar manner to that of Preparation 36.

(2S)-2-hydroxy-2-phenyl-N-[4-(4-pyridinyl)phenyl]acetamide

1H-NMR (DMSO-d6): δ 5.14 (1H, s), 6.51 (1H, s), 7.28-7.33 (1H, m), 7.34-7.40 (2H, m), 7.52-7.56 (2H, m), 7.69 (2H, dd, J=1.6, 4.5 Hz), 7.79 (2H, d, J=8.8 Hz), 7.89 (2H, d, J=8.8 Hz), 8.60 (2H, dd, J=1.6, 4.5 Hz), 10.15 (1H, s)

MS (ESI, m/z): 327 (M+Na)

Example 131

The following compound was obtained in a similar manner to that of Example 53.

N-3,4'-bipyridin-6-yl-L-phenylalaninamide

1H-NMR (DMSO-d6): δ 2.6-2.8 (1H, m), 3.0-3.15 (1H, m), 4.65-4.75 (1H, m), 7.1-7.3 (5H, m), 7.75-7.85 (2H, m), 8.25-8.35 (2H, m), 8.6-8.7 (2H, m), 8.81 (1H, s)

MS (ESI, m/z): no data

Example 132

The following compound was obtained in a similar manner to that of Example 53.

N-3,4'-bipyridin-6-yl-D-phenylalaninamide

1H-NMR (DMSO-d6): δ 2.76 (1H, dd, J=8.3, 13.4 Hz), 3.06 (1H, dd, J=5.2, 13.4 Hz), 3.76 (1H, dd, J=5.2, 8.3 Hz), 7.15-7.23 (1H, m), 7.23-7.31 (4H, m), 7.76 (2H, dd, J=1.6, 4.5 Hz), 8.19-8.31 (2H, m), 8.63 (2H, dd, J=1.6, 4.5 Hz), 8.76-8.72 (1H, m)

MS (ESI, m/z): 319 (M+H)

Example 133

The following compound was obtained in a similar manner to that of Example 53.

N-2,4'-bipyridin-5-yl-L-phenylalaninamide

1H-NMR (DMSO-d6): δ 2.76 (1H, dd, J=7.9, 13.4 Hz), 3.03 (1H, dd, J=5.6, 13.4 Hz), 3.64 (1H, dd, J=5.6, 7.9 Hz), 7.12-7.38 (5H, m), 8.01 (2H, dd, J=1.6, 4.6 Hz), 8.10 (1H, d, J=8.6 Hz), 8.26 (1H, dd, J=2.5, 8.6 Hz), 8.66 (2H, dd, J=1.6, 4.6 Hz), 8.91 (1H, d, J=2.5 Hz)

MS (ESI, m/z): 319 (M+H)

Example 134

The following compound was obtained in a similar manner to that of Example 53.

N-2,4'-bipyridin-5-yl-D-phenylalaninamide

1H-NMR (DMSO-d6): δ 2.78 (1H, dd, J=7.9, 13.4 Hz), 3.03 (1H, dd, J=5.6, 13.4 Hz), 3.64 (1H, dd, J=5.6, 7.9 Hz), 7.17-7.23 (1H, m), 7.23-7.33 (4H, m), 8.01 (2H, dd, J=1.6, 4.6 Hz), 8.08-8.13 (1H, m), 8.25 (1H, dd, J=2.6, 8.8 Hz), 8.66 (2H, dd, J=1.6, 4.6 Hz), 8.88-8.93 (1H, m)

MS (ESI, m/z) 319 (M+H)

Example 135

The following compound was obtained in a similar manner to that of Example 53.

N-[4-(3-fluoropyridin-4-yl)phenyl]-D-phenylalaninamide dihydrochloride

1H-NMR (DMSO-d6): δ 3.1-3.27 (2H, m), 4.3-4.4 (1H, m), 7.23-7.36 (4H, m), 7.69-7.81 (4H, m), 8.45-8.52 (2H, m), 8.55 (1H, d, J=5.1 Hz), 8.75 (1H, d, 3.0 Hz)

MS (ESI, m/z): 335 (M+H)

Example 136

The following compound was obtained in a similar manner to that of Preparation 36 and successively Example 53.

N-(2-methyl-4-pyridin-4-ylphenyl)-D-phenylalaninamide

1H-NMR (DMSO-d6): δ 3.1-3.27 (2H, m), 4.3-4.4 (1H, m), 7.23-7.36 (4H, m), 7.69-7.81 (4H, m), 8.45-8.52 (2H, m), 8.55 (1H, d, J=5.1 Hz), 8.75 (1H, d, 3.0 Hz)

MS (ESI, m/z): 335 (M+H)

Example 137

The following compound was obtained in a similar manner to that of Example 53.

N-[4-(2-aminopyrimidin-4-yl)phenyl]-D-phenylalaninamide

1H-NMR (DMSO-d6): δ 2.74 (1H, dd, J=13.5, 8.0 Hz), 3.02 (1H, dd, J=13.5, 5.5 Hz), 3.60 (1H, dd, J=7.8, 5.5 Hz), 6.59 (2H, s), 7.08 (1H, d, J=5.1 Hz), 7.17-7.30 (5H, m), 7.73 (2H, d, J=8.8 Hz), 8.03 (2H, dd, J=8.8 Hz), 8.23 (1H, d, J=5.0 Hz)

MS (ESI, m/z): 334 (M+H)

Example 138

The following compound was obtained in a similar manner to that of Example 53.

N-[4-(2-aminopyrimidin-4-yl)phenyl]-4-fluoro-D-phenylalaninamide

1H-NMR (DMSO-d6): δ 2.73 (1H, dd, J=8.0, 13.5 Hz), 2.99 (1H, dd, J=5.5, 13.5 Hz), 3.56 (1H, dd, J=5.5, 8.0 Hz), 6.59 (2H, s), 7.07-7.11 (3H, m), 7.26-7.30 (2H, m), 7.73 (2H, d, J=8.8 Hz), 8.03 (2H, d, J=8.8 Hz), 8.26 (1H, d, J=5.4 Hz)

MS (ESI, m/z): 352 (M+H)

Example 139

The following compound was obtained in a similar manner to that of Preparation 36 and successively Example 53.

N-[4-(2-aminopyrimidin-4-yl)phenyl]-3-fluoro-D-phenylalaninamide

1H-NMR (DMSO-d6): δ 2.76 (1H, dd, J=8.2, 13.5 Hz), 3.03 (1H, dd, J=5.3, 13.5 Hz), 3.60 (1H, dd, J=5.3, 8.2 Hz), 6.59 (2H, s), 6.99-7.04 (1H, m), 7.07-7.13 (3H, m), 7.28-7.34 (1H, m), 7.73 (2H, d, J=8.8 Hz), 8.04 (2H, d, J=8.8 Hz), 8.27 (1H, d, J=5.0 Hz)

MS (ESI, m/z): 352 (M+H)

Example 140

The following compound was obtained in a similar manner to that of Preparation 36 and successively Example 53.

N-[4-(2-aminopyrimidin-4-yl)phenyl]-2-fluoro-D-phenylalaninamide

1H-NMR (DMSO-d6): δ 2.80 (1H, dd, J=8.0, 13.6 Hz), 3.03 (1H, dd, J=6.0, 13.6 Hz), 3.61 (1H, dd, J=6.0, 8.0 Hz), 6.59 (2H, s), 7.07-7.15 (1H, m), 7.22-7.28 (1H, m), 7.31-7.35 (1H, m), 7.72 (2H, d, J=8.8 Hz), 8.03 (2H, d, J=8.8 Hz), 8.26 (1H, d, J=5.3 Hz)

MS (ESI, m/z): 352 (M+H)

Example 141

The following compound was obtained in a similar manner to that of Example 53.

N-[4-(2-aminopyrimidin-4-yl)phenyl]-4-chloro-D-phenylalaninamide

1H-NMR (DMSO-d6): δ 2.73 (1H, dd, J=8.2, 13.5 Hz), 2.99 (1H, dd, J=5.5, 13.5 Hz), 3.55-3.59 (1H, m), 6.59 (2H, s), 7.08 (1H, d, J=5.4 Hz), 7.26-7.34 (4H, m), 7.72 (2H, d, J=8.8 Hz), 8.03 (2H, d, J=8.8 Hz), 8.26 (1H, d, J=5.3 Hz)

MS (ESI, m/z): 368 (M+H)

Example 142

The following compound was obtained in a similar manner to that of Example 53.

N-[4-(2-aminopyrimidin-4-yl)phenyl]-O-methyl-D-tyrosinamide

1H-NMR (DMSO-d6): δ 2.68 (1H, dd, J=7.8, 13.5 Hz), 2.95 (1H, dd, J=5.6, 13.5 Hz), 3.54 (1H, dd, J=5.6, 7.8 Hz), 3.71 (3H, s), 6.59 (2H, s), 6.84 (2H, d, J=8.7 Hz), 7.08 (1H, d, J=5.3 Hz), 7.16 (2H, d, J=8.6 Hz), 7.74 (2H, d, J=8.8 Hz), 8.03 (2H, d, J=8.8 Hz), 8.26 (1H, d, J=5.3 Hz)

MS (ESI, m/z): 364 (M+H)

Example 143

The following compound was obtained in a similar manner to that of Example 53.

(2R)—N-[4-(2-aminopyrimidin-4-yl)phenyl]-2-morpholin-4-yl-3-phenylpropanamide

1H-NMR (DMSO-d6): δ 2.68 (1H, dd, J=7.8, 13.5 Hz), 2.95 (1H, dd, J=5.6, 13.5 Hz), 3.54 (1H, dd, J=5.6, 7.8 Hz), 3.71 (3H, s), 6.59 (2H, s), 6.84 (2H, d, J=8.7 Hz), 7.08 (1H, d, J=5.3 Hz), 7.16 (2H, d, J=8.6 Hz), 7.74 (2H, d, J=8.8 Hz), 8.03 (2H, d, J=8.8 Hz), 8.26 (1H, d, J=5.3 Hz)

MS (ESI, m/z): 364 (M+H)

Example 144

The following compound was obtained in a similar manner to that of Preparation 36' and successively Example 53.

N-[4-(2-aminopyrimidin-4-yl)phenyl]-2-(4-hydroxypiperidin-1-yl)-2-phenylacetamide 1H-NMR (DMSO-d6): δ 2.63-2.67 (4H, m), 2.89 (1H, dd, J=5.0, 13.2 Hz), 3.10 (1H, dd, J=9.7, 13.2 Hz), 3.51 (1H, dd, J=5.0, 9.7 Hz), 3.56-3.59 (4H, m), 6.60 (2H, s), 7.06 (1H, d, J=5.3 Hz), 7.13-7.19 (1H, m), 7.24-7.25 (4H, m), 7.67 (2H, d, J=8.9 Hz), 8.01 (2H, d, J=8.8 Hz), 8.26 (1H, d, J=5.2 Hz), 10.02 (1H, br)

MS (ESI, m/z): 404 (M+H)

Example 145

The following compound was obtained in a similar manner to that of Preparation 36 and successively Example 53.

N-[4-(4-pyridinyl)phenyl]-D-valinamide

1H-NMR (DMSO-d6): δ 0.87 (3H, d, J=6.8 Hz), 0.94 (3H, d, J=6.8 Hz), 1.95 (1H, septet, J=6.8 Hz), 3.14 (1H, d, J=5.5 Hz), 7.69 (2H, dd, J=4.5, 1.6 Hz), 7.76-7.83 (4H, m), 8.60 (2H, dd, J=4.5, 1.6 Hz)

MS (ESI, m/z): 270 (M+H)

Example 146

The following compound was obtained in a similar manner to that of Preparation 36 and successively Example 53.

N-[4-(4-pyridinyl)phenyl]-D-leucinamide

1H-NMR (DMSO-d6): δ 0.89 (3H, d, J=6.6 Hz), 0.92 (3H, d, J=6.6 Hz), 1.3-1.38 (1H, m), 1.45-1.53 (1H, m), 1.76 (1H, septet, J=6.6 Hz), 3.32-3.38 (1H, m), 7.69 (2H dd, J=4.6, 1.6 Hz), 7.77-7.83 (4H, m), 8.60 (2H, dd, J=4.6, 1.6 Hz)

MS (ESI, m/z): 284 (M+H)

Example 147

The following compound was obtained in a similar manner to that of Example 53.

4-cyano-N-[4-(4-pyridinyl)phenyl]-D-phenylalaninamide

1H-NMR (DMSO-d6): δ 2.84 (1H, dd, J=13.4, 8.2 Hz), 3.09 (1H, dd, J=13.4, 5.3 Hz), 3.64 (1H, dd, J=8.2, 5.3 Hz), 7.47 (2H, d, J=8.2 Hz), 7.66-7.71 (2H, m), 7.72-7.82 (6H, m), 8.57-8.63 (2H, m)

MS (ESI, m/z): 343 (M+H)

Example 148

The following compound was obtained in a similar manner to that of Example 53.

N-[4-(4-pyridinyl)phenyl]-D-tyrosinamide

1H-NMR (DMSO-d6): δ 2.64 (1H, dd, J=13.5, 7.8 Hz), 2.89 (1H, dd, J=13.5, 5.6 Hz), 3.52 (1H, dd, J=7.6, 5.7 Hz), 6.66 (2H, d, J=8.4 Hz), 7.03 (2H, d, J=8.4 Hz), 7.67-7.70 (2H, m), 7.74-7.81 (4H, m), 8.57-8.62 (2H, m), 9.15 (1H, s)

MS (ESI, m/z): 334 (M+H)

Example 149

The following compound was obtained in a similar manner to that of Example 53.

4-nitro-N-[4-(4-pyridinyl)phenyl]-D-phenylalaninamide dihydrochloride

1H-NMR (DMSO-d6): δ 3.25-3.33 (1H, m), 3.42-3.50 (1H, m), 4.48-4.56 (1H, m), 7.70 (2H, d, J=8.7 Hz), 7.89 (2H, d, J=8.8 Hz), 8.07 (2H, d, J=8.7 Hz), 8.21 (2H, d, J=8.7 Hz), 8.31 (2H, d, J=6.7 Hz), 8.55 (3H, br s), 8.89 (2H, d, J=6.7 Hz), 11.72 (1H, br s)

MS (ESI, m/z): 334 (M+H)

Example 150

The following compound was obtained in a similar manner to that of Example 53.

(2R)-1-oxo-3-phenyl-1-(5-pyridin-4-yl-2,3-dihydro-1H-indol-1-yl)propan-2-amine dihydrochloride 1H-NMR (DMSO-d6): δ 2.86-2.97 (1H, m), 3.10-3.30 (3H, m), 3.45-3.55 (1H, m), 4.23-4.33 (1H, m), 4.44-4.56 (1H, br), 7.23-7.35 (5H, m), 7.93-7.99 (2H, m), 8.20-8.26 (1H, m), 8.28-8.34 (2H, m), 8.57-8.80 (3H, br), 8.87-8.92 (2H, m)

MS (ESI, m/z): 344 (M+H)

Example 151

The following compound was obtained in a similar manner to that of Example 53.

4-{1-[(2S)-2-amino-3-phenylpropanoyl]-2,3-dihydro-1H-indol-5-yl}pyrimidin-2-amine 1H-NMR (DMSO-d6): δ 2.65-2.76 (1H, m), 2.93-2.99 (1H, m), 3.01-3.21 (2H, m), 3.76-3.84 (1H, m), 3.85-3.95 (1H, m), 4.22-4.34 (1H, m), 6.58 (2H, br s), 7.07 (1H, d, J=5.3 Hz), 7.14-7.30 (5H, m), 7.89-7.97 (2H, m), 8.15-8.21 (1H, m), 8.25 (1H, d, J=5.3 Hz)

MS (ESI, m/z): 360 (M+H)

Example 152

The following compound was obtained in a similar manner to that of Example 53.

4-{1-[(2R)-2-amino-3-phenylpropanoyl]-2,3-dihydro-1H-indol-5-yl}pyrimidin-2-amine 1H-NMR (DMSO-d6): δ 2.65-2.76 (1H, m), 2.93-2.99 (1H, m), 3.01-3.21 (2H, m), 3.76-3.84 (1H, m), 3.85-3.95 (1H, m), 4.22-4.34 (1H, m), 6.58 (2H, br s), 7.07 (1H, d, J=5.3 Hz), 7.14-7.30 (5H, m), 7.89-7.97 (2H, m), 8.15-8.21 (1H, m), 8.25 (1H, d, J=5.3 Hz)

MS (ESI, m/z): 360 (M+H)

Example 153

The following compound was obtained in a similar manner to that of Example 53.

(2S)-2-amino-N-[4-(2-aminopyrimidin-4-yl)phenyl]-2-phenylacetamide

1H-NMR (DMSO-d6): δ 4.56 (1H, s), 6.60 (2H, s), 7.07 (1H, d, J=5.3 Hz), 7.24-7.28 (1H, m), 7.324-7.36 (2H, m), 7.47-7.50 (2H, m), 7.76 (2H, d, J=8.7 Hz), 8.03 (2H, d, J=8.8 Hz), 8.26 (1H, d, J=5.1 Hz)

MS (ESI, m/z): 320 (M+H)

Example 154

The following compound was obtained in a similar manner to that of Example 53.

(2R)-2-amino-N-[4-(2-aminopyrimidin-4-yl)phenyl]-2-phenylacetamide

1H-NMR (DMSO-d6): δ 4.56 (1H, s), 6.58 (2H, s), 7.07 (1H, d, J=5.3 Hz), 7.24-7.28 (1H, m), 7.32-7.36 (2H, m), 7.47-7.50 (2H, m), 7.76 (2H, d, J=8.8 Hz), 8.03 (2H, d, J=8.8 Hz), 8.26 (1H, d, J=5.2 Hz)

MS (ESI, m/z): 320, (M+H)

Example 155

The following compound was obtained in a similar manner to that of Example 53.

(2S)-2-amino-N-[4-(2-aminopyrimidin-4-yl)phenyl]-2-(2-thienyl)acetamide

1H-NMR (DMSO-d6): δ 4.79 (1H, br), 6.60 (2H, s), 6.97 (1H, dd, J=3.4, 4.9 Hz), 7.06-7.09 (2H, m), 7.41 (1H, dd, 1.3, 5.0 Hz), 7.76 (2H, d, J=8.8 Hz), 8.05 (2H, d, J=8.8 Hz), 8.27 (1H, d, J=5.1 Hz)

MS (ESI, m/z): 326 (M+H)

Example 156

The following compound was obtained in a similar manner to that of Example 53.

(2S)-2-amino-N-[4-(2-aminopyrimidin-4-yl)phenyl]-2-(2-thienyl)acetamide

1H-NMR (DMSO-d6): δ 2.97 (1H, dd, J=8.8, 13.6 Hz), 3.10 (1H, dd, J=5.5, 13.6 Hz), 4.74-4.78 (1H, m), 7.01-7.06 (1H, m), 7.09-7.11 (2H, m), 7.32 (1H, dd, J=7.7, 14.4 Hz), 7.68-7.73 (4H, m), 7.80-7.82 (2H, m), 8.59-8.61 (2H, m), 10.34 (1H, br)

MS (ESI, m/z): 340 (M+H)

Example 157

The following compound was obtained in a similar manner to that of Example 53.

1-[4-(2-aminopyrimidin-4-yl)phenyl]-3-[(1S)-2-hydroxy-1-phenylethyl]urea

1H-NMR (DMSO-d6): δ 3.56-3.69 (2H, m), 4.73-4.78 (1H, m), 5.01 (1H, t, J=5.1 Hz), 6.54 (2H, s), 6.83 (1H, d, J=7.7 Hz), 7.03 (1H, d, J=5.3 Hz), 7.21-7.27 (1H, m), 7.32-7.34 (4H, m), 7.48 (2H, d, J=8.8 Hz), 7.96 (2H, d, J=8.9 Hz), 8.22 (1H, d, J=5.3 Hz), 8.93 (1H, br)

MS (ESI, m/z): 350 (M+H)

Example 158

The following compound was obtained in a similar manner to that of Example 53.

4-{1-[(2S)-2-amino-2-phenylacetyl]-2,3-dihydro-1H-indol-5-yl}pyrimidin-2-amine

1H-NMR (DMSO-d6): δ 2.24 (2H, s), 3.05-3.24 (2H, m), 3.73-3.82 (1H, m), 4.36-4.44 (1H, m), 4.80 (1H, s), 6.58 (2H, s), 7.06 (1H, d, J=5.3 Hz), 7.25-7.30 (1H, m), 7.33-7.43 (4H, m), 7.91-7.95 (2H, m), 8.22 (1H, d, J=8.8 Hz), 8.25 (1H, d, J=5.2 Hz)

MS (ESI, m/z): 346 (M+H)

Example 159

The following compound was obtained in a similar manner to that of Example 53.

4-{1-[(2R)-2-amino-2-phenylacetyl]-2,3-dihydro-1H-indol-5-yl}pyrimidin-2-amine

1H-NMR (DMSO-d6): δ 2.24 (2H, s), 3.05-3.24 (2H, m), 3.73-3.82 (1H, m), 4.36-4.44 (1H, m), 4.80 (1H, s), 6.58 (2H, s), 7.06 (1H, d, J=5.3 Hz), 7.25-7.30 (1H, m), 7.33-7.43 (4H, m), 7.91-7.95 (2H, m), 8.22 (1H, d, J=8.8 Hz), 8.25 (1H, d, J=5.2 Hz)

MS (ESI, m/z): 346 (M+H)

Example 160

The following compound was obtained in a similar manner to that of Example 53.

4'-{1-[(2S)-2-amino-3-(4-fluorophenyl)propanoyl]-2,3-dihydro-1H-indol-5-yl}pyrimidin-2-amine 1H-NMR (DMSO-d6): δ 2.64-2.74 (1H, m), 2.91-3.00 (1H, m), 3.06-3.25 (2H, m), 3.73-3.83 (1H, m), 3.92-4.03 (1H, m), 4.24-4.37 (1H, m), 6.58 (2H, br s), 7.03-7.13 (3H, m), 7.26-7.35 (2H, m), 7.88-7.99 (2H, m), 8.13-8.21 (1H, m), 8.25 (1H, d, J=5.2 Hz)

MS (ESI, m/z): 378 (M+H)

Example 161

The following compound was obtained in a similar manner to that of Preparation 36 and successively Example 53.

4-{(2S)-2-amino-3-[5-(2-aminopyrimidin-4-yl)-2,3-dihydro-1H-indol-1-yl]-3-oxopropyl}phenol 1H-NMR (DMSO-d6): δ2.70-2.78 (1H, m), 2.86-2.95 (1H, m), 2.96-3.07 (1H, m), 3.09-3.20 (1H, m), 3.70-3.79 (1H, m), 3.91-3.99 (1H, m), 4.18-4.29 (1H, m), 6.59 (2H, br s), 6.64 (2H, d, J=8.5 Hz), 7.04 (2H, d, J=8.4 Hz), 7.07 (1H, d, J=5.3 Hz), 7.89-7.99 (2H, m), 8.17 (1H, d, J=8.4 Hz), 8.26 (1H, d, J=5.2 Hz), 9.23 (1H, br s)

MS (ESI, m/z): 376 (M+H)

Example 162

The following compound was obtained in a similar manner to that of Preparation 37 and successively Example 53.

(2R)-1-oxo-3-phenyl-1-(6-pyridin-4-yl-3,4-dihydroquinolin-1 (2H)-yl)propan-2-amine Dihydrochloride 1H-NMR (DMSO-d6): δ 1.35-1.85 (3H, m), 3.0-3.3 (2H, m), 3.85-4.0 (1H, m), 4.7-4.9 (1H, m), 6.75-6.95 (1H, m), 7.1-7.4 (4H, m), 7.75-7.95 (3H, m), 8.36 (2H, d, J=6.2 Hz), 8.6-8.8 (1H, m), 8.93 (2H, d, J=6.2 Hz), 8.9-9.0 (2H, m)

MS (ESI, m/z): 358 (M+H)

TABLE 1 example number and its chemical compound
Ex: example number; Str.: chemical structure;

| Ex | Str. |
|---|---|
| 1 | 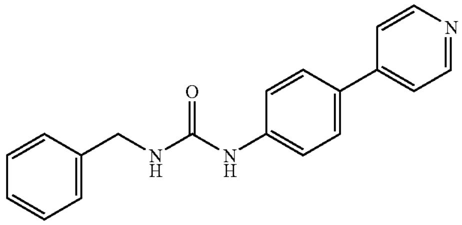 |

TABLE 1-continued example number and its chemical compound
Ex: example number; Str.: chemical structure;

| Ex | Str. |
|---|---|
| 2 | 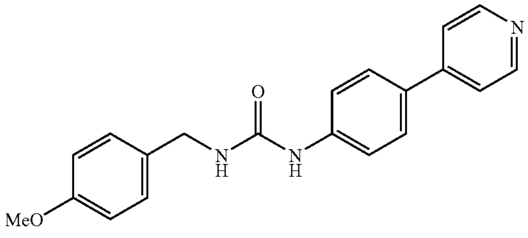 |
| 3 | 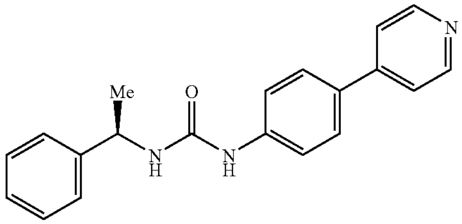 |
| 4 | 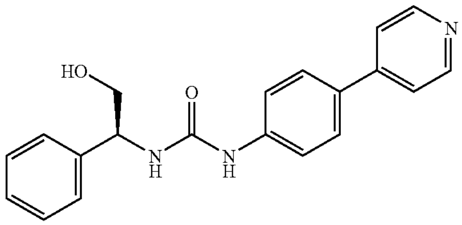 |
| 5 | 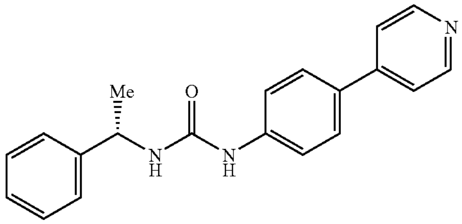 |
| 6 | 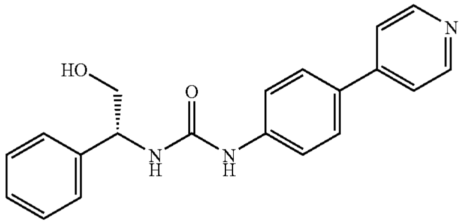 |
| 7 | 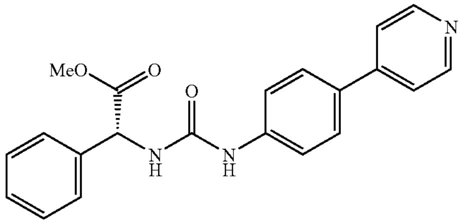 |

TABLE 1-continued
example number and its chemical compound
Ex: example number; Str.: chemical structure;
| Ex | Str. |
|---|---|
| 8 | 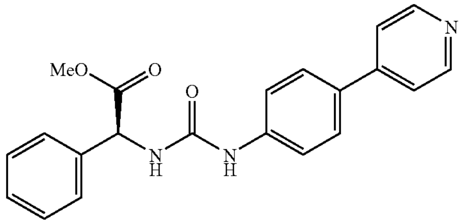 |
| 9 | 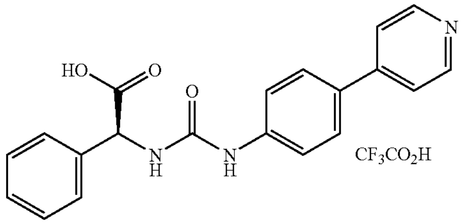 |
| 10 | 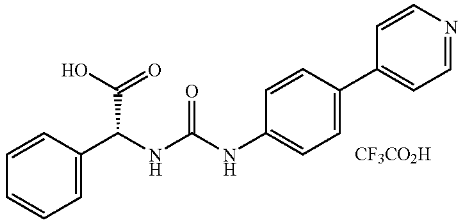 |
| 11 | 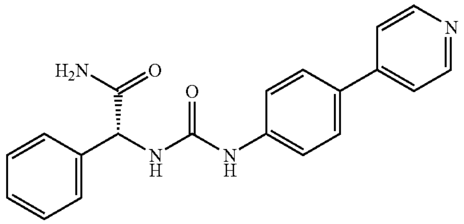 |
| 12 | 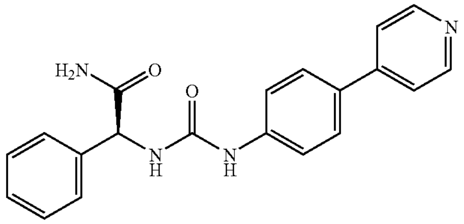 |
| 13 | 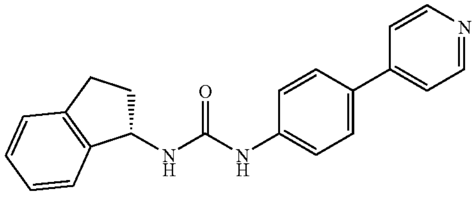 |
| 14 | 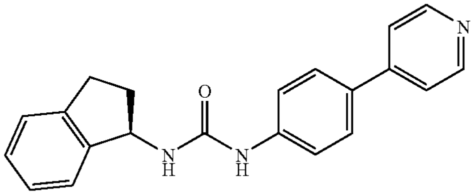 |
| 15 | 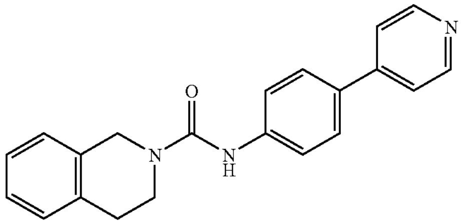 |
| 16 | 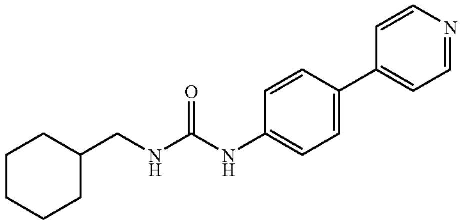 |
| 17 | 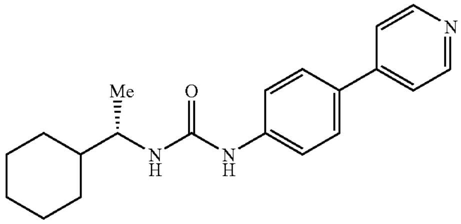 |
| 18 | 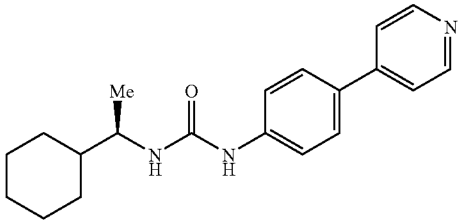 |
| 19 | 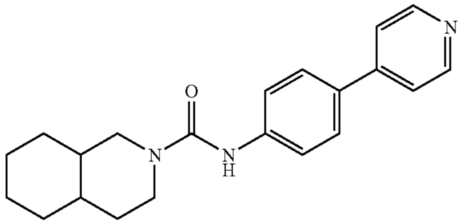 |

TABLE 1-continued
| example number and its chemical compound Ex: example number; Str.: chemical structure; | |
|---|---|
| Ex | Str. |
| 20 | 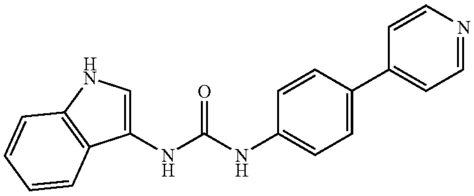 |
| 21 | 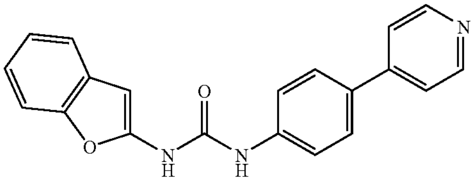 |
| 22 | 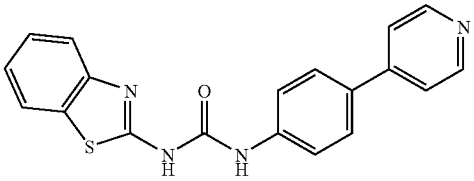 |
| 23 | 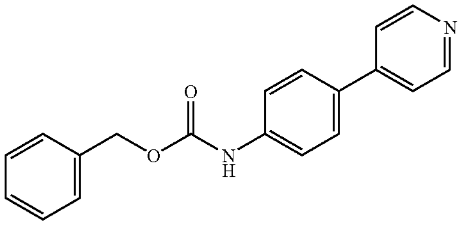 |
| 24 | 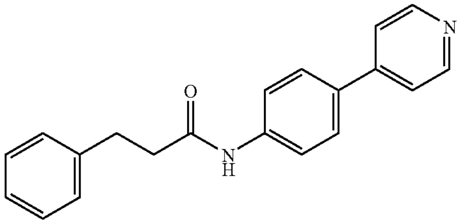 |
| 25 | 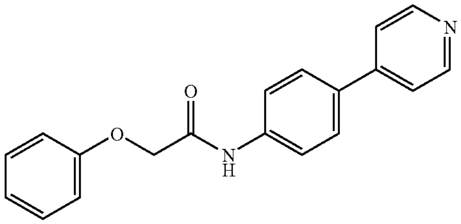 |
| 26 | 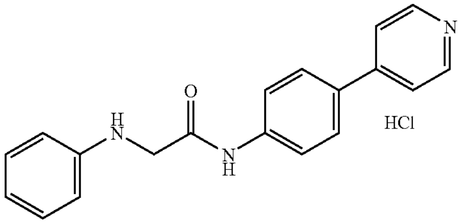 HCl |
TABLE 1-continued
| example number and its chemical compound Ex: example number; Str.: chemical structure; | |
|---|---|
| Ex | Str. |
| 27 | 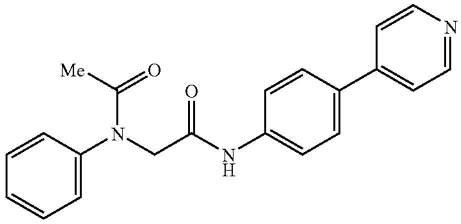 |
| 28 | 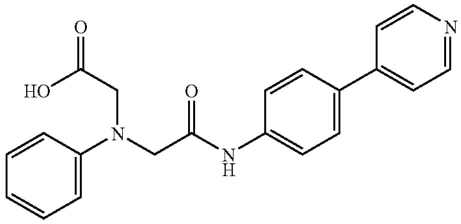 |
| 29 | 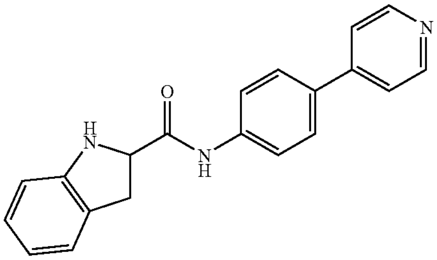 |
| 30 | 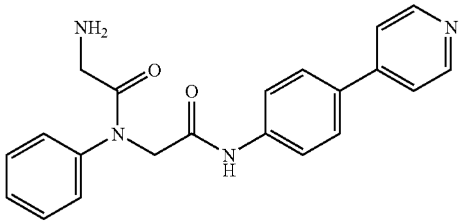 |
| 31 | 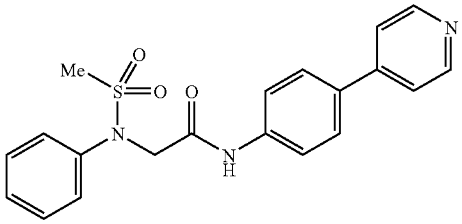 |
| 32 | 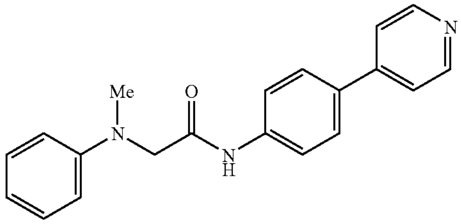 |

TABLE 1-continued
| example number and its chemical compound Ex: example number; Str.: chemical structure; | |
|---|---|
| Ex | Str. |
| 33 | 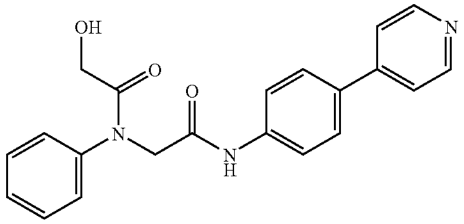 |
| 34 | 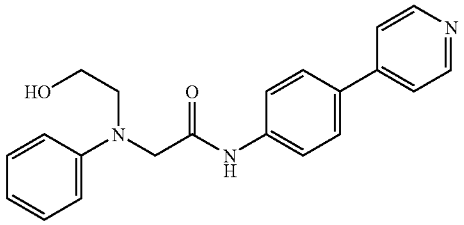 |
| 35 | 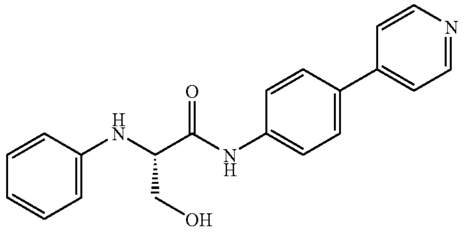 |
| 36 | 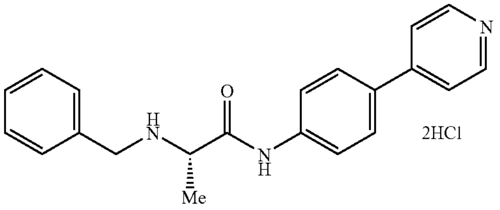 2HCl |
| 37 | 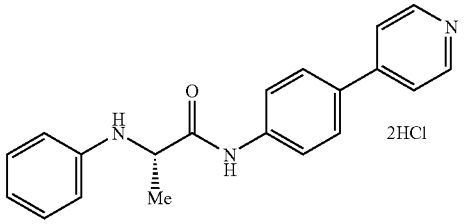 2HCl |
| 38 | 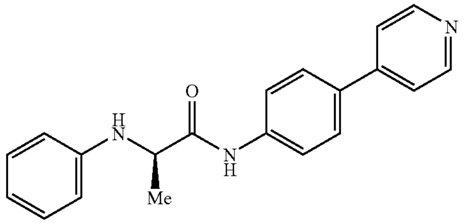 |
| 39 | 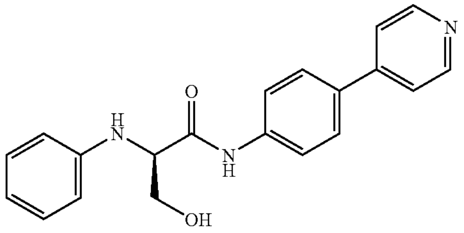 |
| 40 | 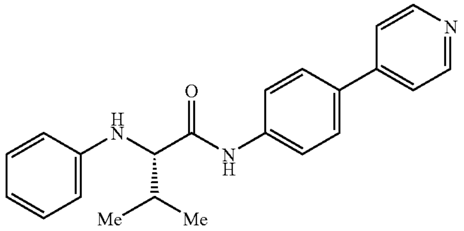 |
| 41 | 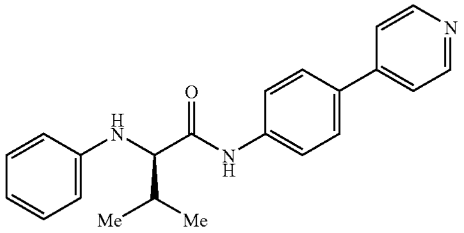 |
| 42 | 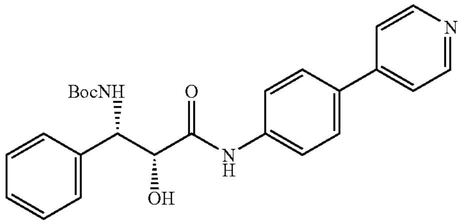 |
| 43 | 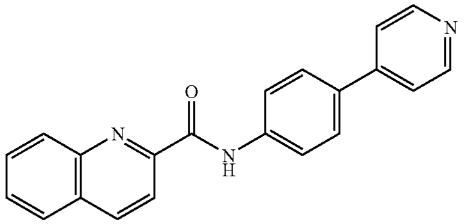 |
| 44 | 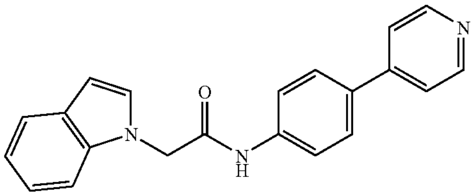 |

TABLE 1-continued
example number and its chemical compound
Ex: example number; Str.: chemical structure;
| Ex | Str. |
|---|---|
| 45 | 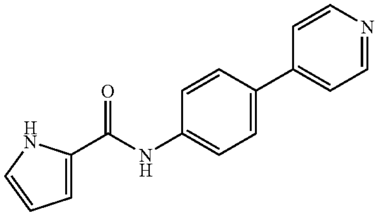 |
| 46 | 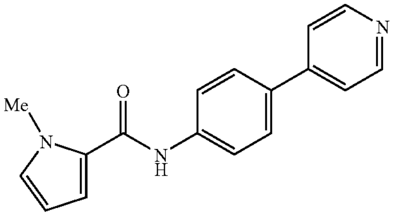 |
| 47 | 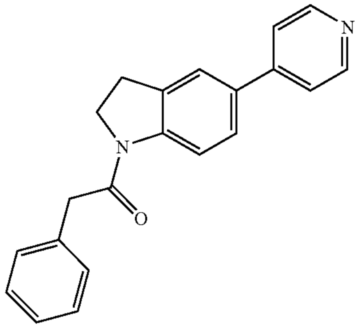 |
| 48 | 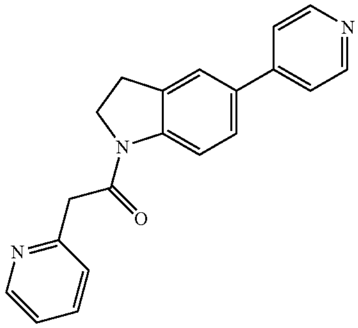 |
| 49 | 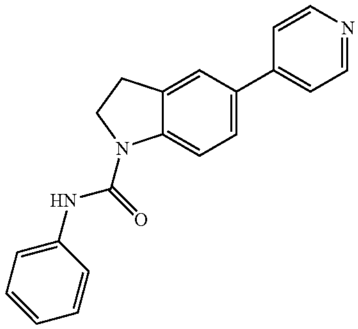 |
| 50 | 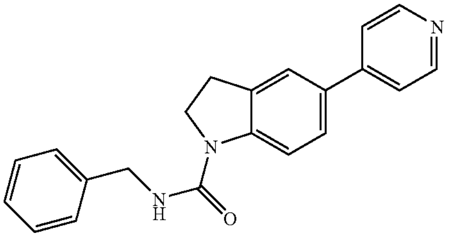 |
| 51 | 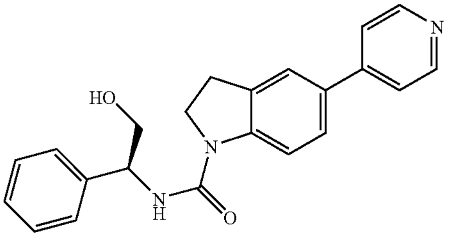 |
| 52 | 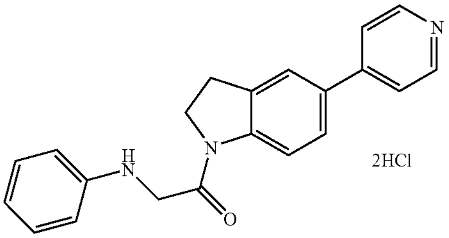 2HCl |
| 53 | 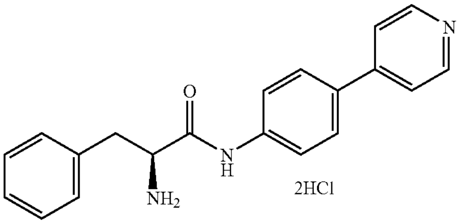 2HCl |
| 54 | 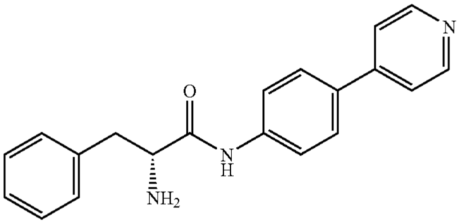 |
| 55 | 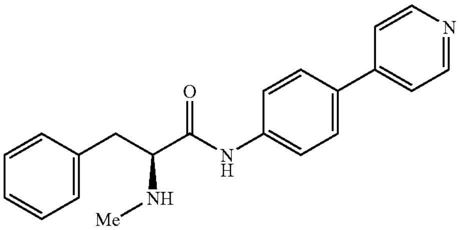 |

TABLE 1-continued
example number and its chemical compound
Ex: example number; Str.: chemical structure;
| Ex | Str. |
|---|---|
| 56 | 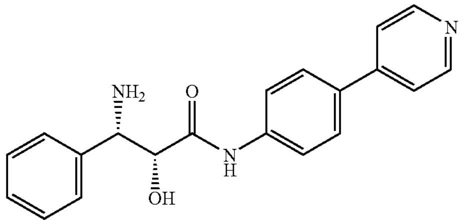 |
| 57 | 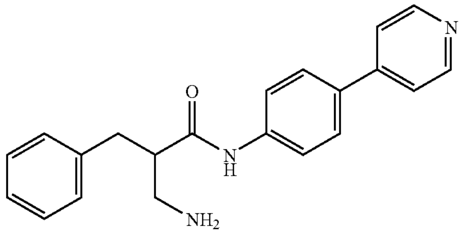 |
| 58 | 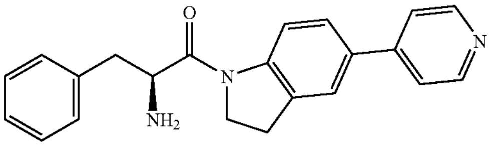 |
| 59 | 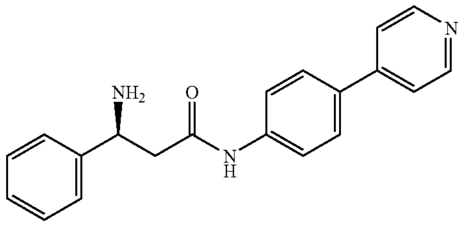 |
| 60 | 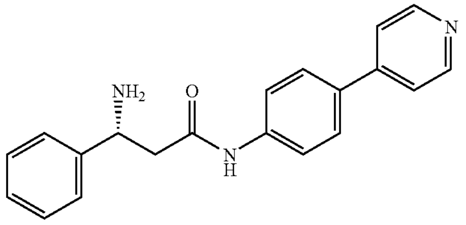 |
| 61 | 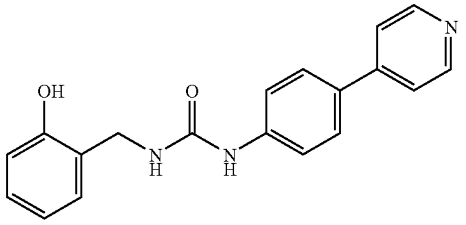 |
TABLE 1-continued
example number and its chemical compound
Ex: example number; Str.: chemical structure;
| Ex | Str. |
|---|---|
| 62 | 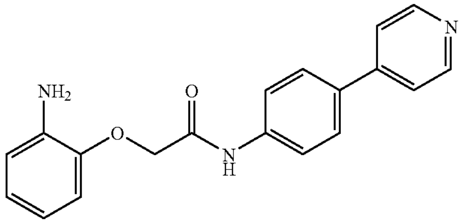 |
| 63 | 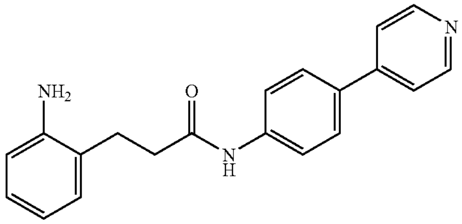 |
| 64 | 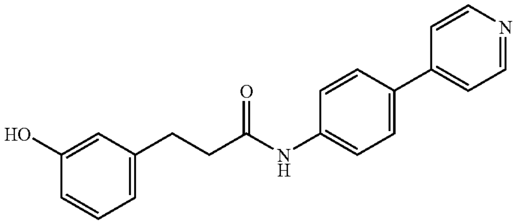 |
| 65 | 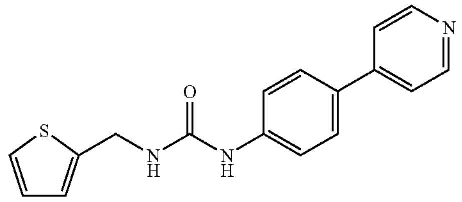 |
| 66 | 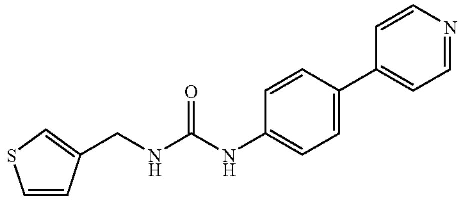 |
| 67 | 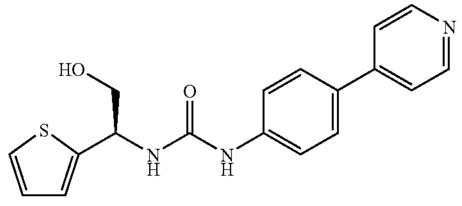 |
| 68 | 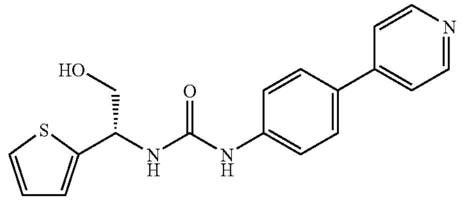 |

TABLE 1-continued
example number and its chemical compound
Ex: example number; Str.: chemical structure;
| Ex | Str. |
|---|---|
| 69 | 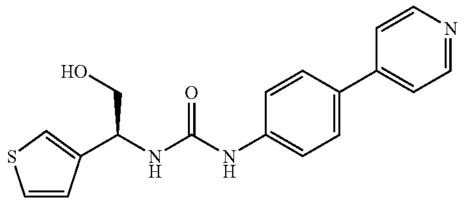 |
| 70 | 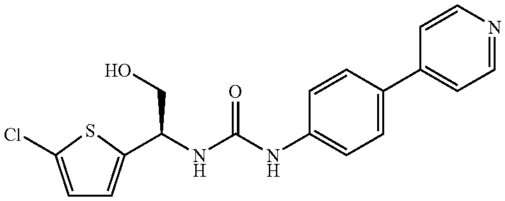 |
| 71 | 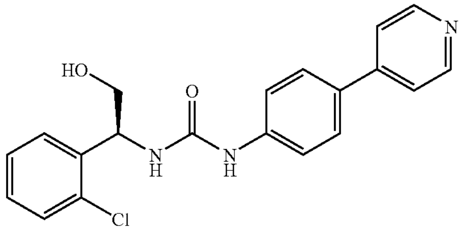 |
| 72 | 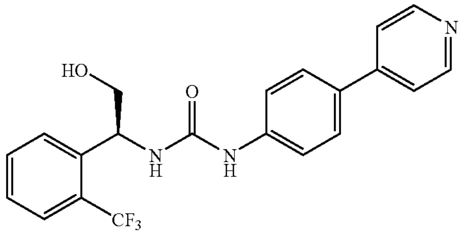 |
| 73 | 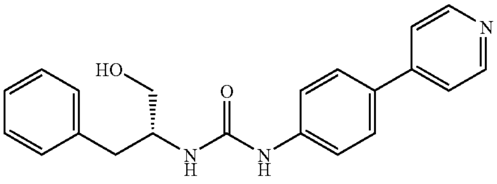 |
| 74 | 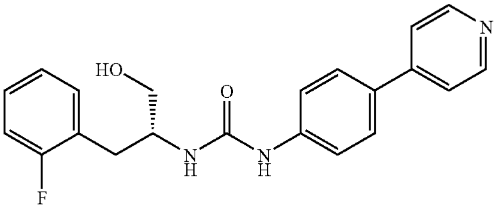 |
| 75 | 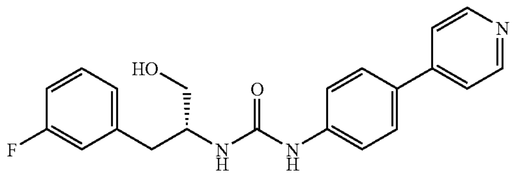 |
TABLE 1-continued
example number and its chemical compound
Ex: example number; Str.: chemical structure;
| Ex | Str. |
|---|---|
| 76 | 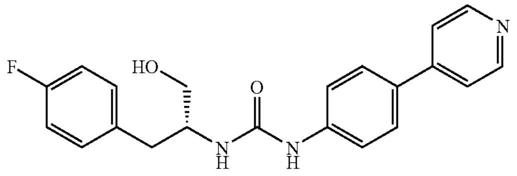 |
| 77 | 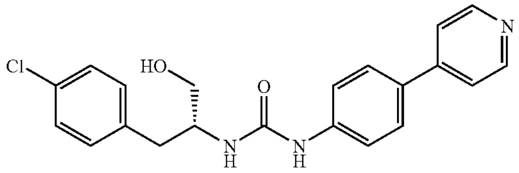 |
| 78 | 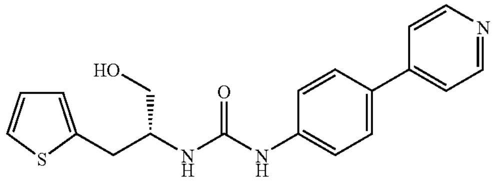 |
| 79 | 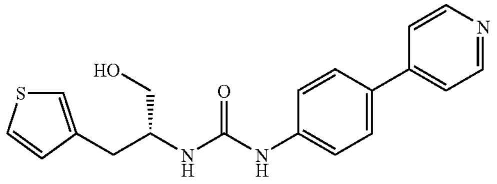 |
| 80 | 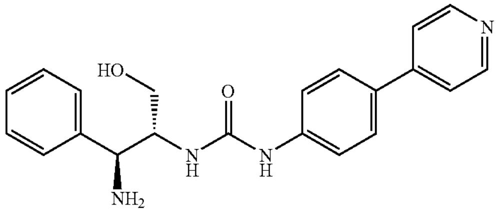 |
| 81 | 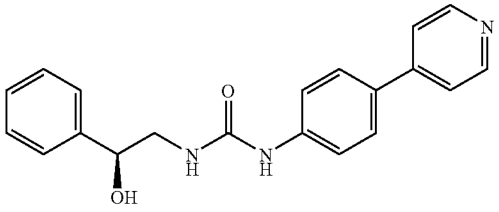 |
| 82 | 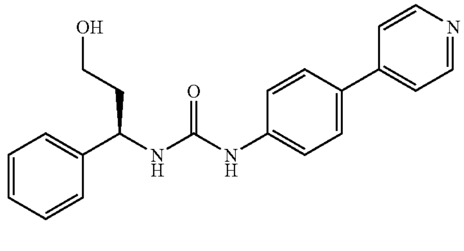 |

TABLE 1-continued
| example number and its chemical compound Ex: example number; Str.: chemical structure; | |
| --- | --- |
| Ex | Str. |
| 83 | 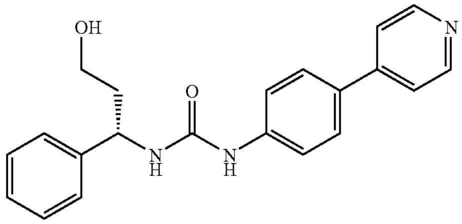 |
| 84 | 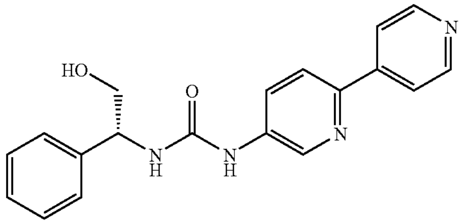 |
| 85 | 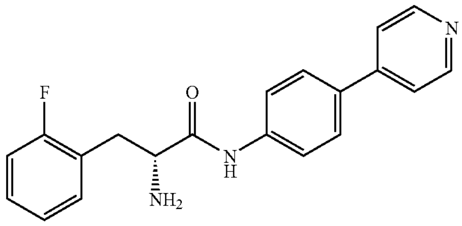 |
| 86 | 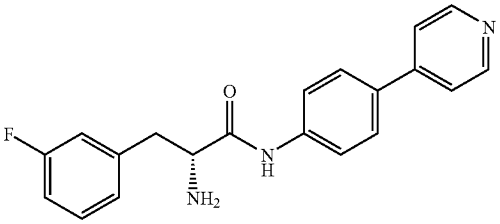 |
| 87 | 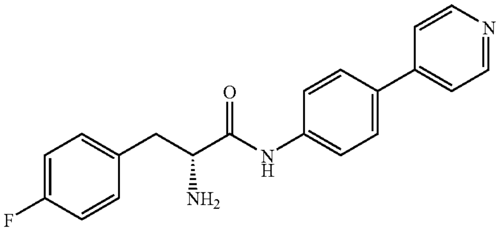 |
| 88 | 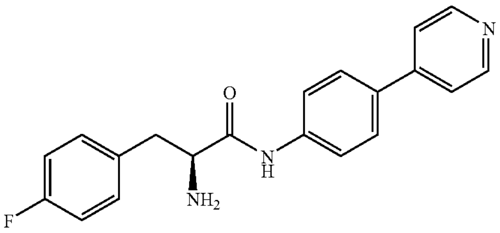 |
TABLE 1-continued
| example number and its chemical compound Ex: example number; Str.: chemical structure; | |
| --- | --- |
| Ex | Str. |
| 89 | 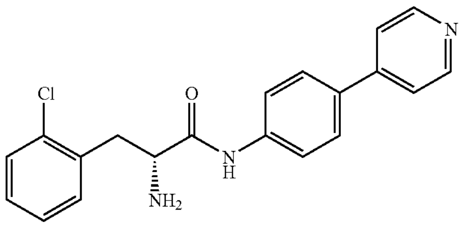 |
| 90 | 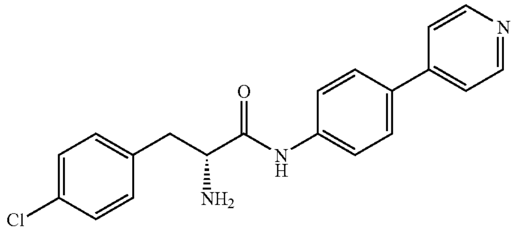 |
| 91 | 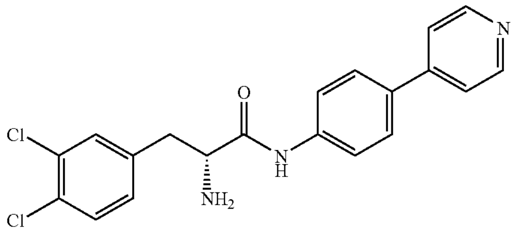 |
| 92 | 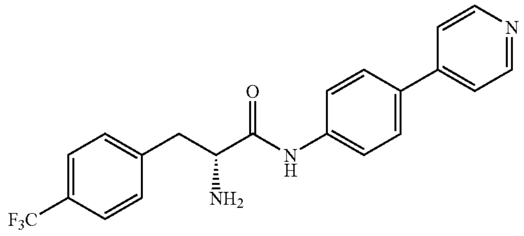 |
| 93 | 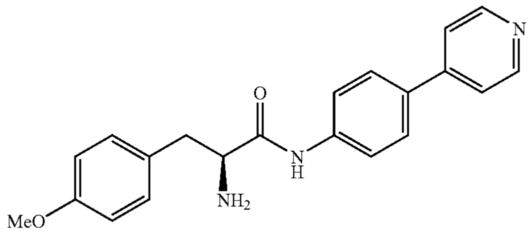 |
| 94 | 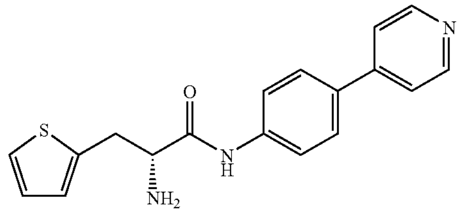 |

TABLE 1-continued
| example number and its chemical compound<br>Ex: example number; Str.: chemical structure; | |
|---|---|
| Ex | Str. |
| 95 | 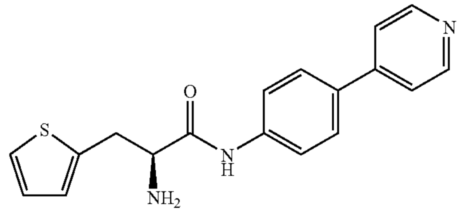 |
| 96 | 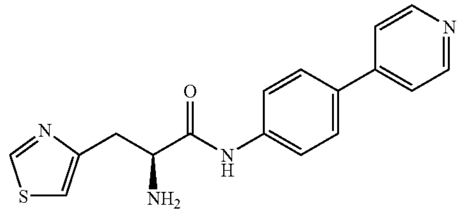 |
| 97 | 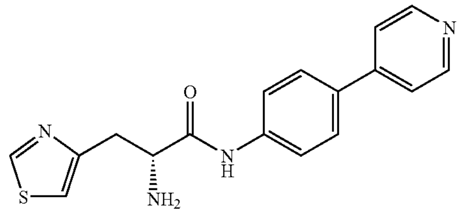 |
| 98 | 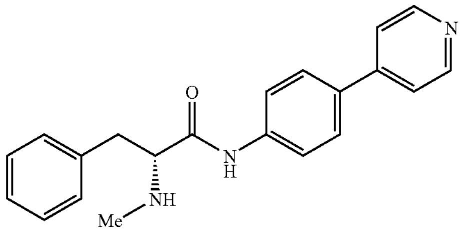 |
| 99 | 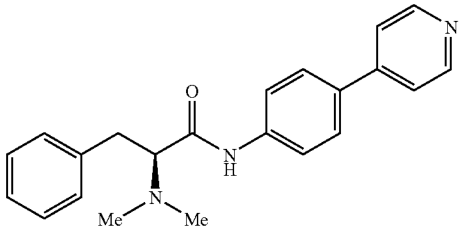 |
| 100 | 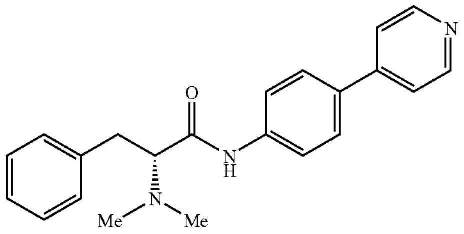 |
TABLE 1-continued
| example number and its chemical compound<br>Ex: example number; Str.: chemical structure; | |
|---|---|
| Ex | Str. |
| 101 | 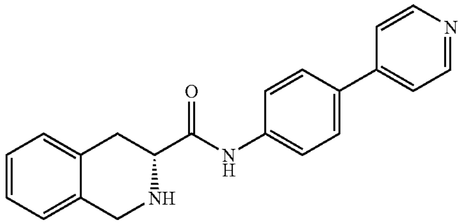 |
| 102 | 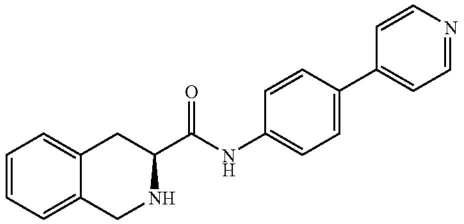 |
| 103 | 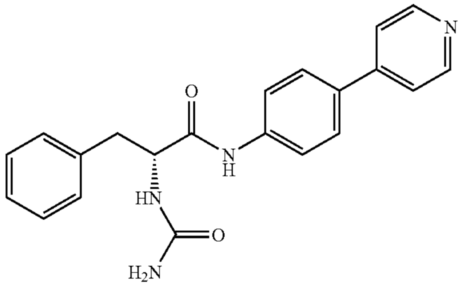 |
| 104 | 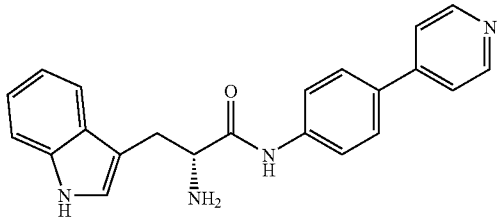 |
| 105 | 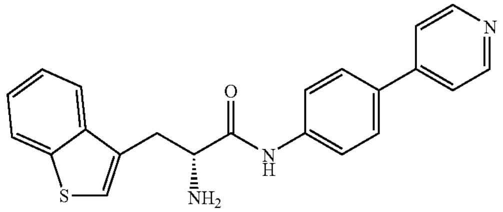 |
| 106 | 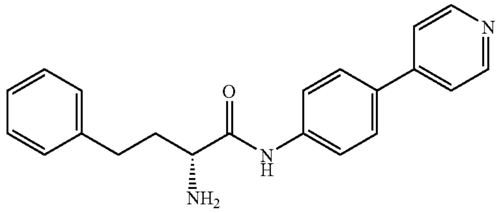 |

TABLE 1-continued
| example number and its chemical compound<br>Ex: example number; Str.: chemical structure; | |
|---|---|
| Ex | Str. |
| 107 | 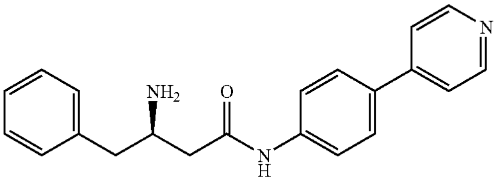 |
| 108 | 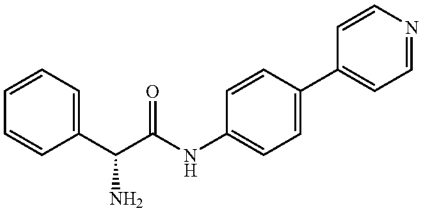 |
| 109 | 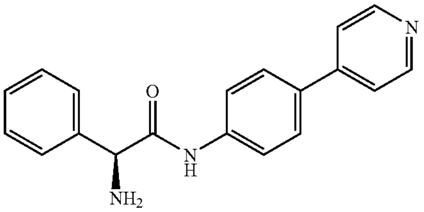 |
| 110 | 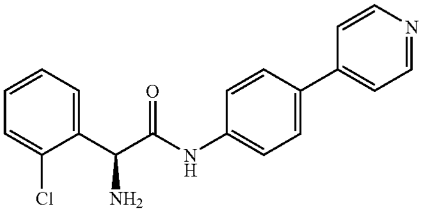 |
| 111 | 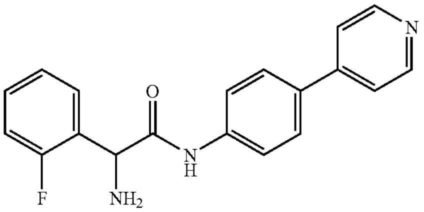 |
| 112 | 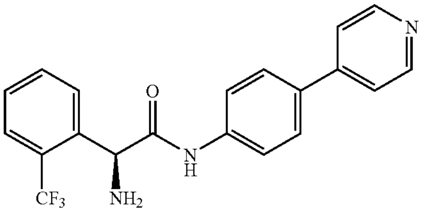 |
| 113 | 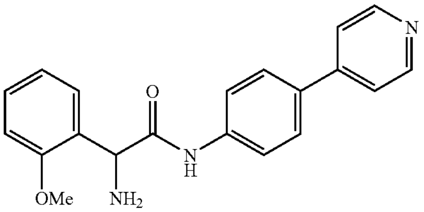 |
TABLE 1-continued
| example number and its chemical compound<br>Ex: example number; Str.: chemical structure; | |
|---|---|
| Ex | Str. |
| 114 | 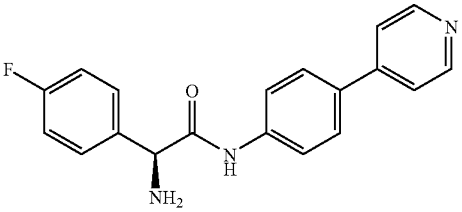 |
| 115 | 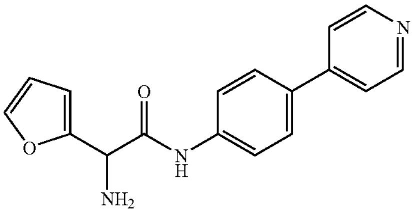 |
| 116 | 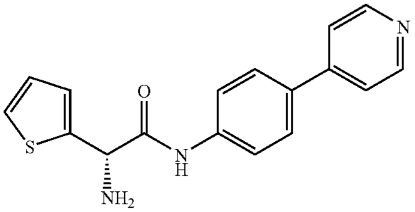 |
| 117 | 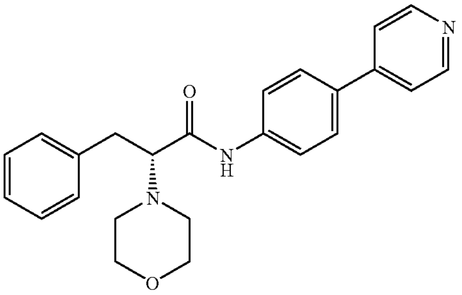 |
| 118 | 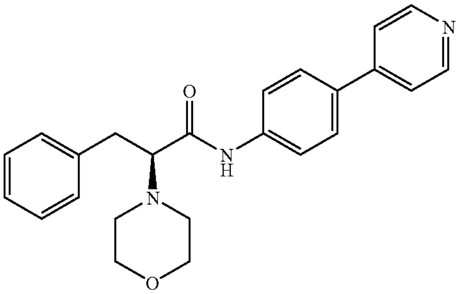 |

TABLE 1-continued
| example number and its chemical compound Ex: example number; Str.: chemical structure; | |
|---|---|
| Ex | Str. |
| 119 | 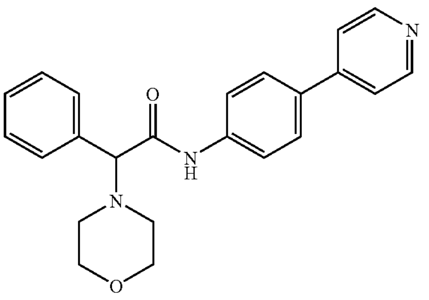 |
| 120 | 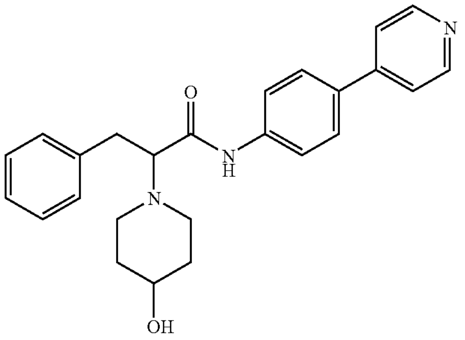 |
| 121 | 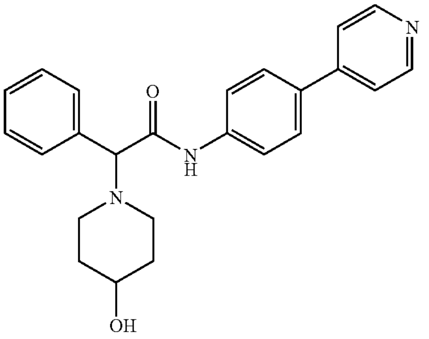 |
| 122 | 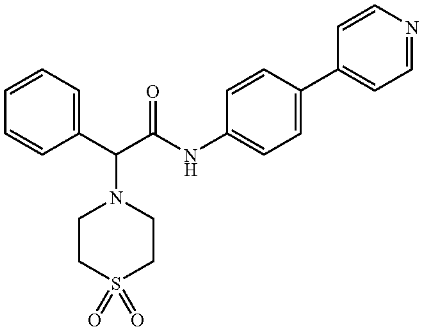 |
TABLE 1-continued
| example number and its chemical compound Ex: example number; Str.: chemical structure; | |
|---|---|
| Ex | Str. |
| 123 | 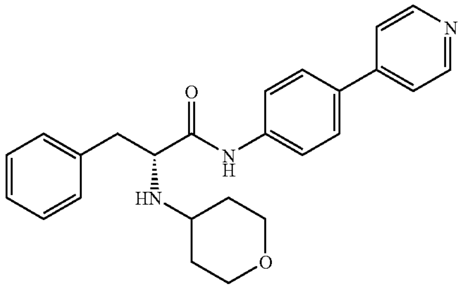 |
| 124 | 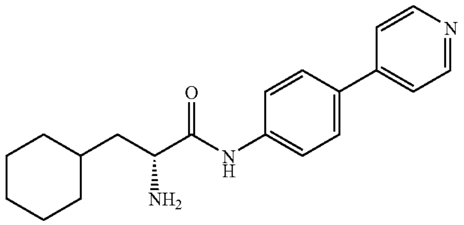 |
| 125 | 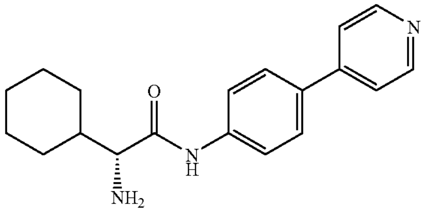 |
| 126 | 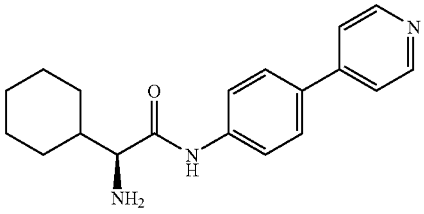 |
| 127 | 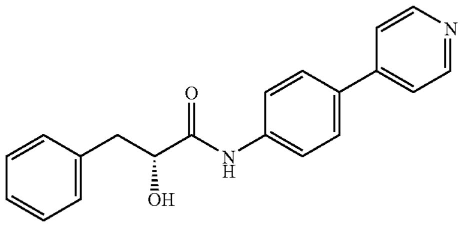 |
| 128 | 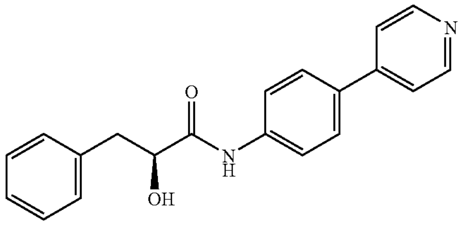 |

TABLE 1-continued
example number and its chemical compound
Ex: example number; Str.: chemical structure;
| Ex | Str. |
|---|---|
| 129 | 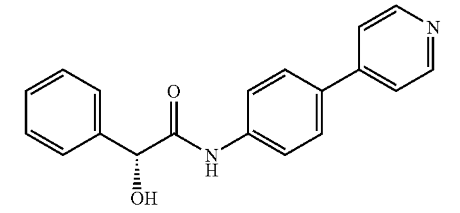 |
| 130 | 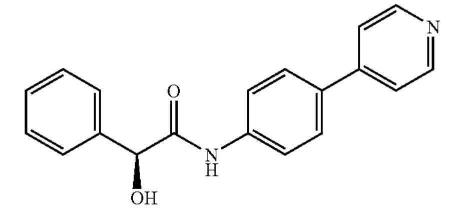 |
| 131 | 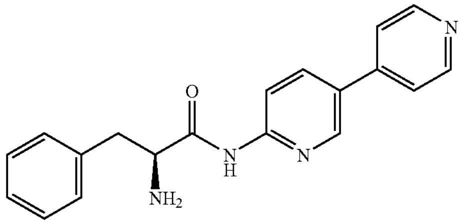 |
| 132 | 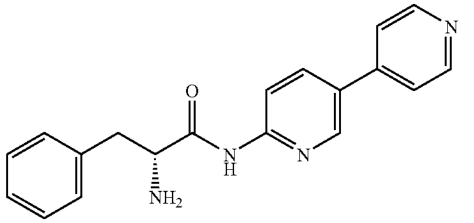 |
| 133 | 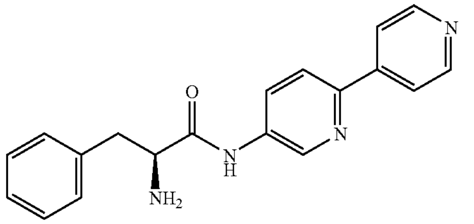 |
| 134 | 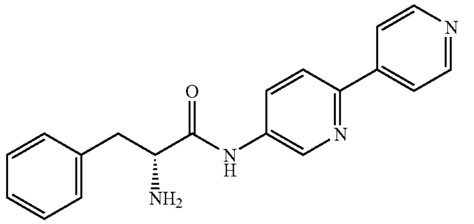 |
TABLE 1-continued
example number and its chemical compound
Ex: example number; Str.: chemical structure;
| Ex | Str. |
|---|---|
| 135 | 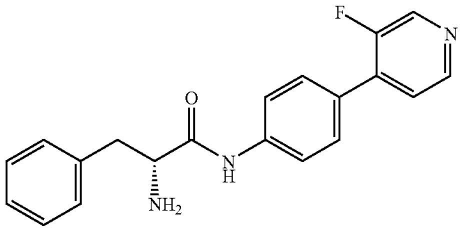 |
| 136 | 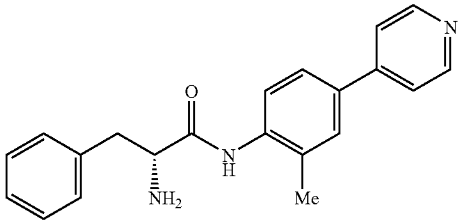 |
| 137 | 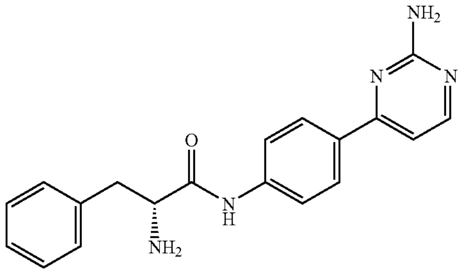 |
| 138 | 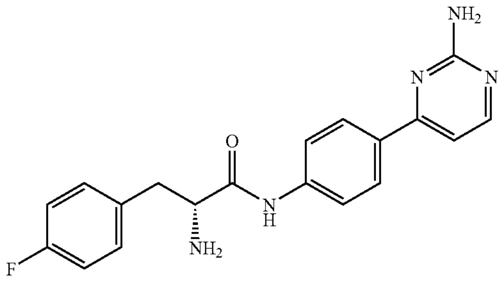 |
| 139 | 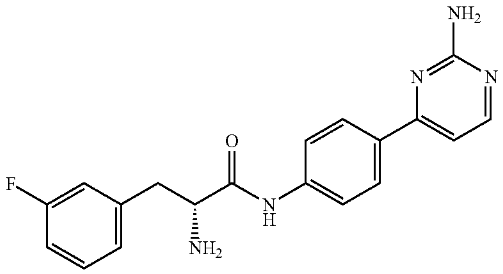 |

TABLE 1-continued
| example number and its chemical compound Ex: example number; Str.: chemical structure; | |
|---|---|
| Ex | Str. |
| 140 | 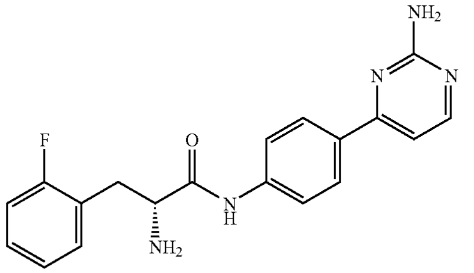 |
| 141 | 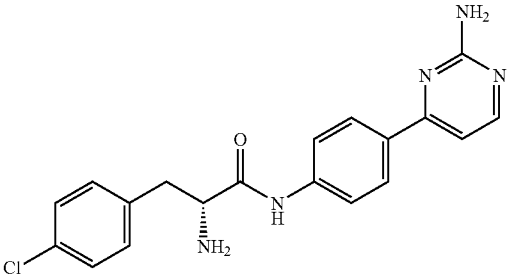 |
| 142 | 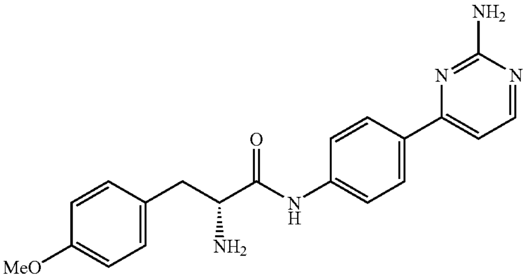 |
| 143 | 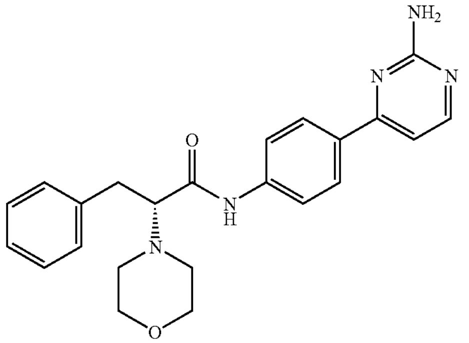 |
| 144 | 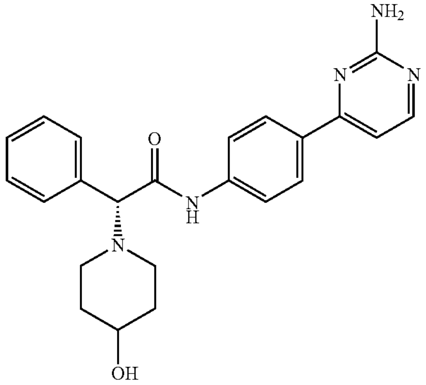 |
TABLE 1-continued
| example number and its chemical compound Ex: example number; Str.: chemical structure; | |
|---|---|
| Ex | Str. |
| 145 | 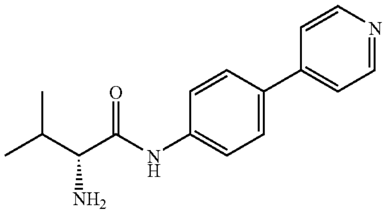 |
| 146 | 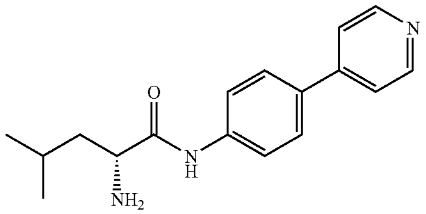 |
| 147 | 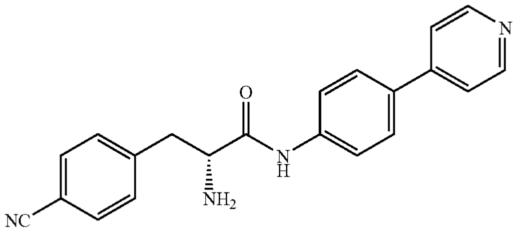 |
| 148 | 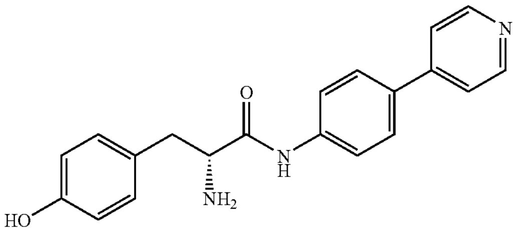 |
| 149 | 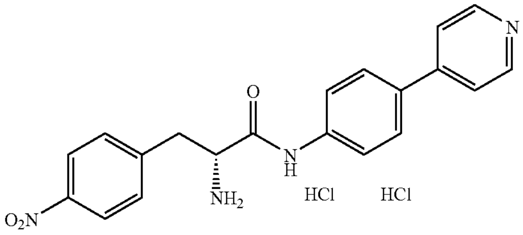 HCl HCl |
| 150 | 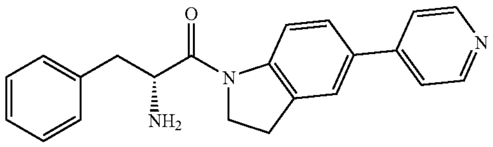 HCl HCl |

TABLE 1-continued

| example number and its chemical compound Ex: example number; Str.: chemical structure; | |
|---|---|
| Ex | Str. |
| 151 | 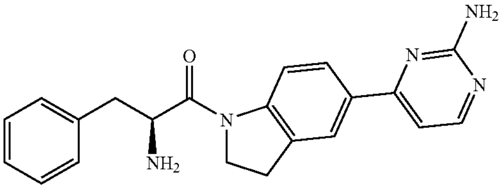 |
| 152 | 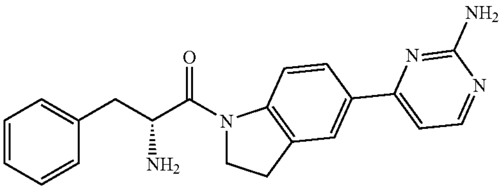 |
| 153 | 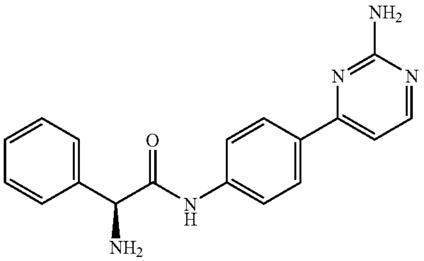 |
| 154 | 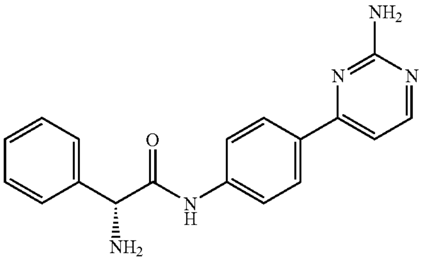 |
| 155 | 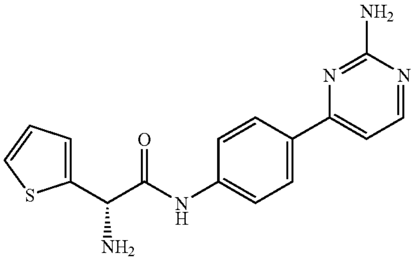 |
| 156 | 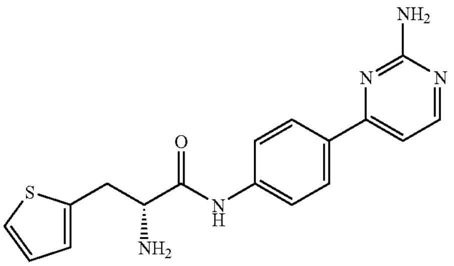 |
| 157 | 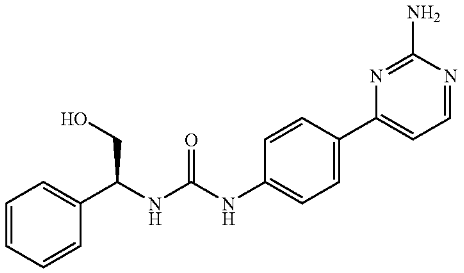 |
| 158 | 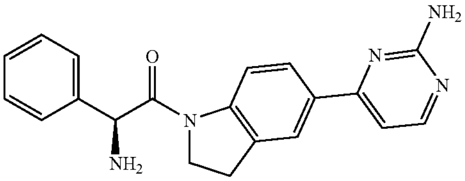 |
| 159 | 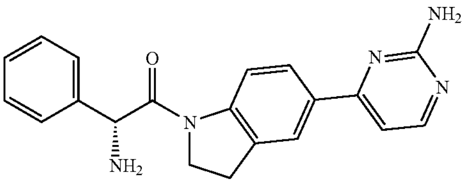 |
| 160 | 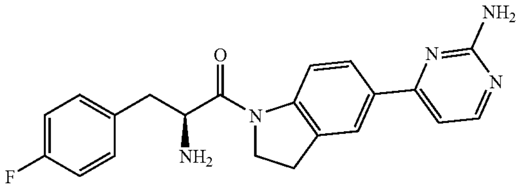 |
| 161 | 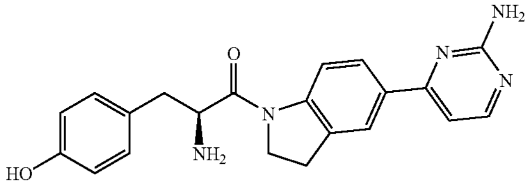 |
| 162 | 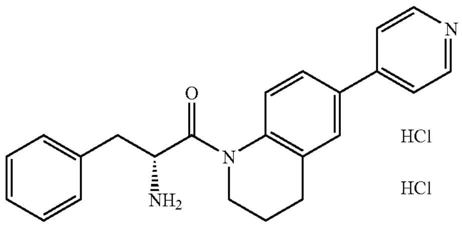 |

In this table, "Me" is meaning of methyl group and "Boc" is meaning of tert-butoxycarbonyl group.

Pharmacological Assay

In order to show the usefulness of the compound [I] for the prophylactic and therapeutic treatment of above-mentioned disease in human being or animals, some representative compounds in the compounds [I] of the present invention as shown in the above examples were tested on the ROCK-inhibiting activity as follows.

1. ROCK Enzyme Inhibition Assay

ROCK enzyme inhibitory activity of the compounds of the present invention has been assayed as follow. A aqueous solution of Rho kinase substrate MYTP was added to 96-well plate. Following incubation for overnight at 4° C., the plate was blocked by using blocking buffer containing BSA. To the plate was added reaction buffer containing each concentration of compound, suitable concentration of human ROCK I (Caruna Biosciences), ATP, β-glycerol phosphate, EGTA, sodium orthovanadate and DTT, and then the plate was incubated for 1 hour. After washing the plate by washing buffer, anti-phosphothreonin antibody was added to the plate, and then the plate was incubated for 1 hour. After washing the plate by washing buffer again, HRP-conjugated anti-phosphorylated protein antibody was added to the plate, and then the plate was incubated for 1 hour. After washing the plate by washing buffer again, calorimetric substrate TMB microwell peroxidase substrate was added to the plate, and then the plate was incubated for appropriate time. After incubation, $H_2SO_4$ was added to the plate to stop the reaction, and then absorbance (450 nm) was measured by using spectromether. Based on the absorbance for each compound, the data is fit using Prism software to obtain a $IC_{50}$ value.

TABLE 2 example number and its human ROCK I $IC_{50}$

| Compound | human ROCK I $IC_{50}$(nM) |
|---|---|
| Example 1 | 342 |
| Example 3 | 240 |
| Example 4 | 122 |
| Example 26 | 77 |
| Example 53 | 18 |
| Example 54 | 10 |
| Example 58 | 53 |
| Example 67 | 112 |
| Example 72 | 25 |
| Example 73 | 84 |
| Example 86 | 5 |
| Example 98 | 21 |
| Example 108 | 14 |
| Example 109 | 12 |
| Example 119 | 212 |
| Example 151 | 86 |
| Example 154 | 42 |
| Example 155 | 72 |

2. Assessment of Changes in Hindlimb Weight Distribution by ROCK Inhibitor

As intra-articular injection of monosodium iodoacetate (MIA) induced human osteoarthritis-like histopathological changes in knee joint, this model would be very useful for the study of human osteoarthritis. Recently, it is reported the clinical scores of the joint pain were closely correrated to the grade of histological findings (J Vet Med Sci 65, 1195, 2003) and this model may be useful for estimation of therapeutic effects of pain with osteoarthritis.

Male SD rats were anesthetized with halothane (Takeda, Japan) and given single intra-articular injection of 1 mg of monosodium iodoacetate (MIA; Sigma, St. Louis, USA) through the infrapatellar ligament of the right knee. MIA was dissolved with physiologic saline and administered in a volume of 50 ul using a 27-gauge, 0.5-inch needle. Three weeks after the injection, hindlimb weight distribution was determined using an incapacitance tester (Linton Instrumentation, Norfork, UK). Rats were allowed to acclimate to the testing apparatus and when stationary, readings were taken over a 5 s period. Oral administration of chemical compounds restored the difference in the amount of weight between the left and right limbs. Each group in each experiment were performed in about 8 animals.

TABLE 3 example number and its weight distribution $ED_{50}$

| Compound | Weight distribution $ED_{50}$ (mg/kg) |
|---|---|
| Example 4 | <3 |
| Example 54 | <3 |
| Example 58 | <3 |
| Example 67 | <3 |
| Example 98 | <3 |
| Example 108 | <3 |
| Example 119 | <3 |
| Example 154 | <3 |

3. Pain Alleviation Effect of ROCK Inhibitor on Bradykinin Induced Joint Pain Model Bradykinin is known to be one of the important pain-related mediators in various pain and especially, sodium hyaluronate which is useful for pain in osteoarthritis is reported to be effective in bradykinin-induced joint pain model. Therefore, we examined effects of compounds in the model.

The making of the joint pain model and evaluation of a level of pain was conducted essentially based on the method described in Folia pharmacol. japon., 92, 17-27 (1988). Female SD rats (6-7 weeks old, Charles River Japan, Inc.) were anesthetized with halothane (Wako). Compound of the above Example were administrated orally to the rat by using oral sonde for rat. 60 min after administration of the compound, saline solution of bradykinin was injected into knee joint cavity of hind limb of rat (3 uM/site/50 ul), and then the response to pain of the rat after administration of bradykinin was observed. Level of pain was scored as five grade point (0-4) as follow: 0: no lameness to lameness for 10 seconds; 1: lameness for 10 to 30 seconds; 2: lift of the limb within 10 seconds or lameness for 31 or more seconds; 3: three-legged gait within 10 seconds followed by lameness; 4: three-legged gait for 10 or more seconds followed by lameness. About 10 rat models were used in each experimental group. It was confirmed that administration of bradykinin leads to response to pain scored as about 3. Administration of the compound of the present invention at 32 mg/kg significantly improved the response to pain of the rat models. The compound of Example 26 dose dependently improved bradykinin-induced pain responses, especially, the pain score significantly reduced from 2.7 in vehicle to 1.4 at the dose of 32 mg/kg.

4. Assessment of Changes in Cartilage Surface Lesion by ROCK Inhibitor

As intra-articular injection of monosodium iodoacetate (MIA) induced human osteoarthritis-like histopathological changes in knee joint, this model would be very useful for the study of human osteoarthritis. To evaluate the usefulness of the compounds to joint cartilage damage in osteoarthritis, we examined effects of the compounds on cartilage damage in the model.

Male SD rats were anesthetized with halothane (Takeda, Japan) and given single intra-articular injection of 1 mg of monosodium iodoacetate (MIA; Sigma, St. Louis, USA) through the infrapatellar ligament of the right knee. MIA was dissolved with physiologic saline and administered in a volume of 50 ul using a 27-gauge, 0.5-inch needle. Three weeks after the injection, a right tibia was isolated and the lesion of the tibial surface were assessed on a scale of 0-4. Each group in each experiment were performed in about 8 animals. The severity of macroscopic cartilage lesion was observed with score of about 3 three weeks after injection of MIA. Articular injection of the compounds twice a week inhibited cartilage damage.

5. Assessment of Effects on Hindlimb Blood Flow by ROCK Inhibitor

As one of the study to clarify the usefulness of the compounds of the present invention for peripheral arterial disease, we conducted a study to evaluate the effects of the compounds on hindlimb blood flow in rats.

Male Wistar rats were anesthetized by intraperitoneal pentobarbital injection (Kanto chemical, Japan) after oral administration of compounds. Rats were placed on a heating plate for subsequent hindlimb blood flow analysis. We measured hindlimb blood flow using a laser Doppler blood flow meter (PeriScan System, Stockholm, Sweden). After the laser Doppler images were recorded, the average perfusion values of both limbs were calculated, and evaluated the effects of compounds on hindlimb blood flow. Each experiment was performed in about 4 animals.

TABLE 4 example number and its % of increase of blood flow

| Compound | % of increase of blood flow (10 mg/kg p.o.) |
|---|---|
| Example 4 | >130% |
| Example 54 | >130% |
| Example 67 | >130% |
| Example 86 | >130% |
| Example 98 | >130% |
| Example 108 | >130% |
| Example 154 | >130% |

6. Assessment of the Inhibitory Effects on Phenylephrine-induced Elevation of Urethral Pressure by ROCK Inhibitor To evaluate the usefulness of the compounds of the present invention for urinary dysfunction associated with benign prostatic hyperplasia, we investigated the inhibitory effects of the intravenous administration of the compounds on phenylephrine-induced elevation of the urethral pressure in rats.

Male Wistar rats were anesthetized with urethane (SIGMA, USA). After midline abdominal incision, catheter to measure the urethral pressure (3.5 Fr, Millar, USA) was inserted into the urethra from top of the bladder. After confirming the Phenylephrine (30 ug/kg i.v.)-induced elevation of the urethral pressure, compounds were administered intravenously in increasing doses. Every 5 min after administration of compounds, Phenylephrine (30 ug/kg i.v.) was injected, and the inhibitory effects of compounds on phenylephrine-induced elevation of urethral pressure were evaluated. Each experiment was performed in about 4 animals.

TABLE 5 example number and its Inhibition of elevation in urethral pressure $ED_{30}$

| Compound | Inhibition of elevation in urethral pressure $ED_{30}$ (mg/kg i.v.) |
|---|---|
| Example 109 | <1 |
| Example 151 | <1 |
| Example 154 | <1 |

The invention claimed is:

1. A compound of formula (I):

(I)

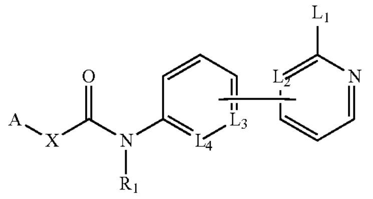

wherein

A is phenyl, cyclohexyl, or thienyl;

$L_1$ is —H;

$L_2$ is CH;

$L_3$ is CH;

$L_4$ is $CR_2$;

$R_1$ and $R_2$ are each independently —H or taken together to form ethylene;

X is —$CHR_5$—$X_1$—;

$X_1$ is —NH— or —$CHR_7$—;

$R_5$ is lower alkyl which may be substituted with —OH or carboxy, —OH, —$NH_2$, —C(O)$NH_2$, —C(O)$OR_8$, or —NHC(O)$OR_9$;

$R_7$ is —H, morpholyl, —OH or —$NR_{10}R_{16}$;

$R_8$, $R_9$, $R_{10}$, and $R_{16}$ are each independently —H or lower alkyl;

or a pharmaceutically acceptable salt thereof.

2. A process for preparing a compound of according to claim 1, which comprises (1) reacting a compound of the formula [II]:

[II]

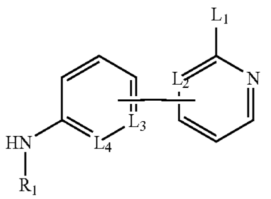

wherein $R_1$, $L_1$, $L_2$, $L_3$ and $L_4$ are each as defined above, or its reactive derivative at the amino group, or a salt thereof, with a compound of the formula [III]:

[III]

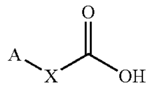

wherein A and X are each as defined above, or its reactive derivative at the carboxy group, or a salt thereof, to give a compound of the formula [I]:

[I]

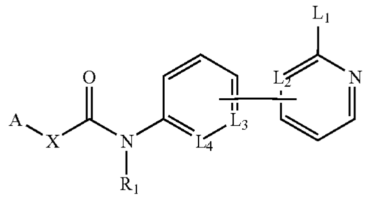

wherein $R_1$, $L_1$, $L_2$, $L_3$, $L_4$, X and A are each as defined above, or a salt thereof, or (2) reacting a compound of the formula [II]:

[II]

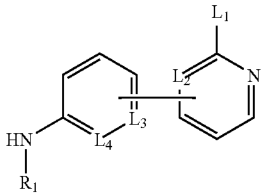

wherein $R_1$, $L_1$, $L_2$, $L_3$ and $L_4$ are each as defined above, or a salt thereof, with a compound of the formula [IV]:

[IV]

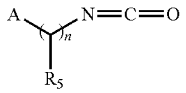

wherein A and $R_5$ are each as defined above, and n is 0 or 1, to give a compound of the formula [Ib]:

[Ib]

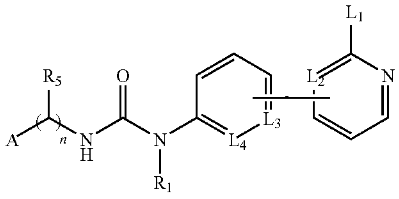

wherein $R_1$, $R_5$, $L_1$, $L_2$, $L_3$, $L_4$, A and n are each as defined above, or a salt thereof, or (3) reacting a compound of the formula [II]:

[II]

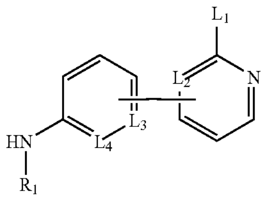

wherein $R_1$, $L_1$, $L_2$, $L_3$ and $L_4$ are each as defined above, or a salt thereof, with a compound of the formula [V]:

[V]

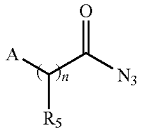

wherein A, $R_5$ and n are each as defined above, to give a compound of the formula [Ib]:

[Ib]

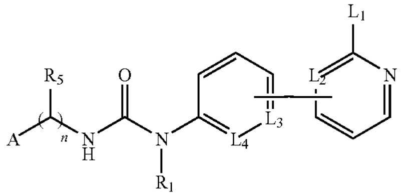

wherein $R_1$, $R_5$, $L_1$, $L_2$, $L_3$, $L_4$, A and n are each as defined above, or a salt thereof, or (4) reacting a compound of the formula [VI]:

[VI]

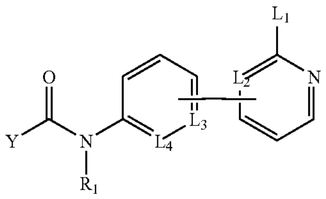

wherein $R_1$, $L_1$, $L_2$, $L_3$ and $L_4$ are each as defined above, and Y is any leaving group, with a compound of the formula [VII]:

[VII]

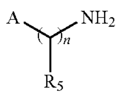

wherein A, $R_5$ and n are each as defined above, to give a compound of the formula [Ib]:

[Ib]

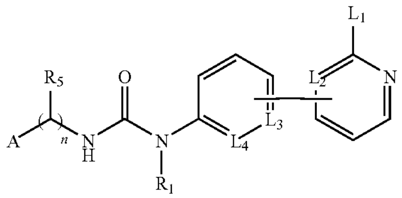

wherein $R_1$, $R_5$, $L_1$, $L_2$, $L_3$, $L_4$, A and n are each as defined above, or a salt thereof, or (5) reacting a compound of the formula [II]:

[II]

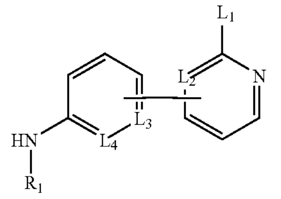

wherein $R_1$, $L_1$, $L_2$, $L_3$ and $L_4$ are each as defined above, or a salt thereof, with a compound of the formula [VIII]:

[VIII]

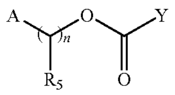

wherein A, $R_5$ and n are each as defined above, Y is any leaving group, to give a compound of the formula [Ic]:

[Ic]

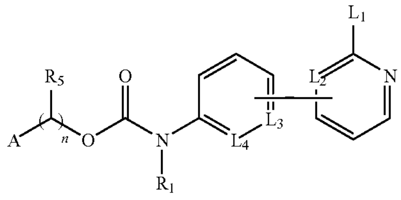

wherein $R_1$, $R_5$, $L_1$, $L_2$, $L_3$, $L_4$, A and n are each as defined above, or a salt thereof, or (6) reacting a compound of the formula [IX]:

[IX]

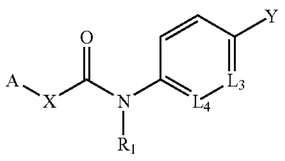

wherein $R_1$, $L_3$, $L_4$, X, Y and A are each as defined above, or a salt thereof, with a compound of the formula [X]:

[X]

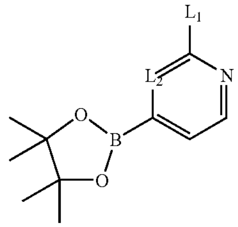

wherein $L_1$ and $L_2$ are each as defined above, or a salt thereof, to give a compound of the formula [Id]:

[Id]

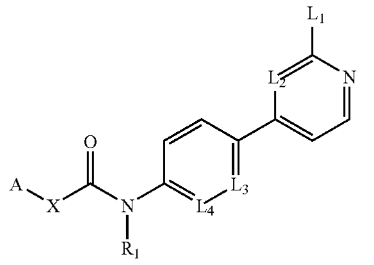

wherein $R_1$, $L_1$, $L_2$, $L_3$, $L_4$, X and A are each as defined above, or a salt thereof, or (7) reacting a compound of the formula [XI]:

[XI]

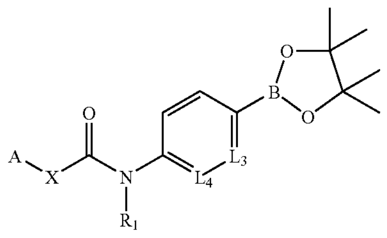

wherein $R_1$, $L_3$, $L_4$, X and A are each as defined above, or a salt thereof, with a compound of the formula [XII]:

[XII]

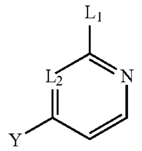

wherein $L_1$, $L_2$, and Y are each as defined above, or a salt thereof, to give a compound of the formula [Ie]:

[Ie]

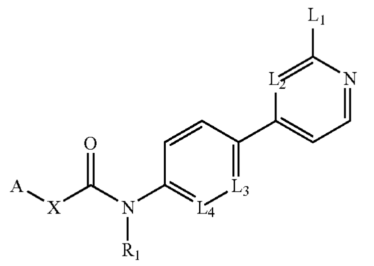

wherein $R_1$, $L_1$, $L_2$, $L_3$, $L_4$, X and A are each as defined above, or a salt thereof.

3. A pharmaceutical composition which comprises, a compound according to claim 1, or a pharmaceutically acceptable salt thereof, and a pharmaceutically acceptable carrier or excipient.

4. A method for treating osteoarthritis, peripheral arterial disease or urinary dysfunction associated with benign prostatic hypertrophy, comprising administering a compound of claim 1, or a pharmaceutically acceptable salt thereof, to a patient in need of such treatment.

5. A compound according to claim 1 which is 1-[(1S)-2-hydroxy-1-phenylethyl]-3-[4-(4-pyridinyl)phenyl]urea or a pharmaceutically acceptable salt thereof.

6. A pharmaceutical composition comprising a compound according to claim 5, or a pharmaceutically acceptable salt thereof, and a pharmaceutically acceptable carrier or excipient.

7. A method for treating osteoarthritis, peripheral arterial disease or urinary dysfunction associated with benign prostatic hypertrophy, comprising administering a compound of claim 5, or a pharmaceutically acceptable salt thereof, to a patient in need of such treatment.

* * * * *